(12) United States Patent
Wolczanski et al.

(10) Patent No.: US 8,846,919 B2
(45) Date of Patent: Sep. 30, 2014

(54) AZAALLYL-CONTAINING MOIETIES AS CHELATE FOR METALS

(75) Inventors: Peter T. Wolczanski, Ithaca, NY (US); Brenda A. Frazier, Ithaca, NY (US)

(73) Assignee: Cornell University, Ithaca, NY (US)

( * ) Notice: Subject to any disclaimer, the term of this patent is extended or adjusted under 35 U.S.C. 154(b) by 325 days.

(21) Appl. No.: 12/704,170

(22) Filed: Feb. 11, 2010

(65) Prior Publication Data

US 2010/0204473 A1 Aug. 12, 2010

Related U.S. Application Data

(60) Provisional application No. 61/151,719, filed on Feb. 11, 2009.

(51) Int. Cl.
| | |
|---|---|
| *C07F 1/02* | (2006.01) |
| *C07F 1/04* | (2006.01) |
| *C07F 3/02* | (2006.01) |
| *C07F 15/02* | (2006.01) |
| *C07F 15/04* | (2006.01) |
| *C07F 15/06* | (2006.01) |
| *C07F 15/00* | (2006.01) |
| *C07D 401/12* | (2006.01) |

(52) U.S. Cl.
CPC ............... *C07D 401/12* (2013.01); *C07F 1/02* (2013.01); *C07F 15/025* (2013.01); *C07F 15/02* (2013.01); *C07F 15/065* (2013.01); *C07F 15/045* (2013.01); *C07F 3/02* (2013.01); *C07F 1/04* (2013.01); *C07F 15/0053* (2013.01)
USPC ................................... 546/2; 546/4; 546/264

(58) Field of Classification Search
CPC .............. C07F 1/02; C07F 1/04; C07F 3/02; C07F 15/0053; C07F 15/065; C07F 15/045; C07F 15/025; C07F 15/02
USPC ................................ 546/2, 4, 264
See application file for complete search history.

(56) References Cited

U.S. PATENT DOCUMENTS

2008/0269491 A1* 10/2008 Jabbour et al. ............. 546/4

OTHER PUBLICATIONS

Geldard et al. Inorganic Chemistry 1963, 2, 270-282.*
Frazier et al. J. Am. Chem. Soc. 2009, 131, 3428-3429.*
Haiduc et al. Basic Organometallic Chemistry, Walter de Gruyter, 1985, 29-33.*
Volpe et al. Organometallics 2010, 29, 364-377.*
Bradamante et al. J. Chem. Soc. Perkin Trans 1, 1987, 515-518.*
Westerhausen M. et al., Unexpected formation of zinc bis[1,3-di(2-pyridyl)-2-azapropenide] during the thermolysis of methylzinc bis(2-pyridylmemyl)amide, Inorganic Chemistry Communications (2004), 7, 763-766.
Geldard JF, et al., Tridentate Chelate Compounds, III, Inorganic Chemistry (1963), 2, 270-82.
Frazier BA et al. "Aryl-Containing Chelates and Amine Debenzylation to Afford 1,3-Di-2-pyridyl-2-azaallyl(smif): Structures of {K-C,N,Npy2-(2-pyridylmethyl)2N(CH2(4-tBu-phenyl-2-yl))}FeBr and (smif)CrN(TMS)2", Inorg. Chem. 2009, 48, 11576-11585.
Bradamante et al. "The reaction of sodium 1,3-diphenyl-2-azapropenide with 1,2-epoxycyclohexane", J. Chem. Soc., Perkin Trans. 1, 1987, 515-518.
Brown SN. "Insertion of a Metal Nitride into Carbon-Carbon Double Bonds", J. Am. Chem. Soc., 1999, 121, 9752-9753.

* cited by examiner

*Primary Examiner* — Joseph Kosack
*Assistant Examiner* — Matthew Coughlin
(74) *Attorney, Agent, or Firm* — Heslin Rothenberg Farley & Mesiti P.C.

(57) ABSTRACT

The invention relates to di-aryl, di-heteroaryl or aryl-heteroaryl azaallyl compounds that are useful as chelates for metals.

22 Claims, 4 Drawing Sheets

AZAALLYL-CONTAINING MOIETIES AS CHELATE FOR METALS

CROSS REFERENCE TO RELATED APPLICATIONS

This application claims priority of U.S. provisional application 61/151,719, filed Feb. 11, 2009, the entire disclosure of which is incorporated herein by reference.

FEDERALLY SPONSORED RESEARCH

This invention was made with Government support under Grant Number CHE-0718030 awarded by the National Science Foundation. The United States Government has certain rights in the invention.

FIELD OF THE INVENTION

The invention relates to di-aryl, di-heteroaryl or aryl-heteroaryl azaallyl compounds that are useful as chelates for metals.

BACKGROUND OF THE INVENTION

Metal and metalloids are bound to ligands in virtually all circumstances. A ligand is an atom, ion, or molecule that bonds to a central metal, generally involving formal donation of one or more of its electrons. Ligands in a complex dictate the reactivity of the central atom, including ligand substitution rates, the reactivity of the ligands themselves, and redox. Ligand selection is a critical consideration in many practical areas.

A metal ion in solution does not exist in isolation, but in combination with ligands or chelating groups, giving rise to complex ions or coordination compounds. The term "chelating ligands" refer to more stable ligands that are attached to a central metal ion by bonds from two or more donor atoms such that they can form a ring including the metal atom. Many of the practical properties of metal complexes (such as color, magnetism, reactivity) are dictated by their electronic structures. Metal complexes often have spectacular colors due to electronic transitions by the absorption of light. The color of a complex depends on the nature of the metal ion as well as the strength and the arrangement of the ligands around the metal ion. Metal complexation is of widespread interest for various applications in areas such as light emitting or light absorbing materials, sensors and catalysts.

SUMMARY OF THE INVENTION

Non-limiting embodiments of the invention are directed to di-aryl, di-heteroaryl or aryl-heteroaryl azaallyl compounds and structural variations thereof. These compounds may be used as chelates for any metal. The optical density of these compounds is useful in various photochemical applications. These compounds have absorption properties that enable applications in various materials requiring high absorptivities, including but not limiting to organic photovoltaics and OLEDs.

In one aspect, the invention relates to a compound comprising at least one azaallyl moeity, wherein the azaallyl moeity is of formula Ia or Ib:

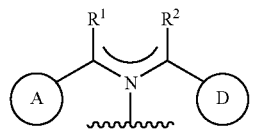

Ia

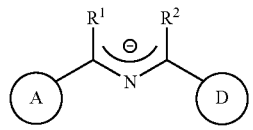

Ib wherein
A is optionally substituted aryl or heteroaryl;
D is optionally substituted aryl or heteroaryl;

⌣ is a delocalized bond;
$R^1$ and $R^2$ are each independently selected from hydrogen, halogen, an optionally substituted ($C_1$-$C_{20}$) hydrocarbon, —C(=O)—$R^{10}$, —C(=O)N$R^{10}R^{11}$, —C(=O)O$R^{10}$, —C(=S)N$R^{10}R^{11}$, —C(=S)—$R^{10}$ and —C(=S)O$R^{10}$; or
$R^1$ and $R^2$, together with the carbons to which they are attached, may be an optionally substituted non-aromatic ring;
$R^{10}$ and $R^{11}$ are each selected independently from hydrogen, an optionally substituted ($C_1$-$C_{20}$) hydrocarbon and a polar, neutral moeity; and ↯ represents a coordinate covalent bond to a metal.

In certain compounds of formula Ia (e.g., when A or D carries a positive charge), the delocalized azaallyl moiety may carry a net negative charge even when bonded to a metal. It is intended that these compounds are to be claimed as well.

In one aspect, the invention relates to a photovoltaic cell comprising at least one of the compounds above.

In one aspect, the invention relates to an organic light emitting diode comprising at least one of the compounds above.

In one aspect, the invention relates to a compound having an extinction coefficient of at least 10,000 ($M^{-1}cm^{-1}$) at a wavelength between 400 and 700 nm and containing the element of structure: (aryl or heteroaryl)-C=N—C-(aryl or heteroaryl).

DETAILED DESCRIPTION OF THE INVENTION

A new ligand type centered around an azaallyl linkage can be used to prepare coordination complexes that possess optical densities approaching those of porphyrins and phthalocyanines. Addition of donor or acceptor substituents on the aryl or heteroaryl ring and directly on the azaallyl backbone and/or changes in metal should enable total coverage of the visible spectrum in many cases.

Ligands of this type, and related scaffolds, can be used to generate complexes for a variety of uses. "smif" and the other azaallyl ligands described herein, with or without metals, are versatile, redox-active ligands with absorption and optical density properties that make them candidates for use in organic photovoltaics (OPV), OLEDs, optical filters, other materials requiring high absorptivities, and various photochemical applications, in addition to being useful as coatings or reflective materials. Their demonstrated ability to accommodate free electrons provides an opportunity to view a successive series of metal complexes derived from smif and other azaallyl ligands.

Figure 4:
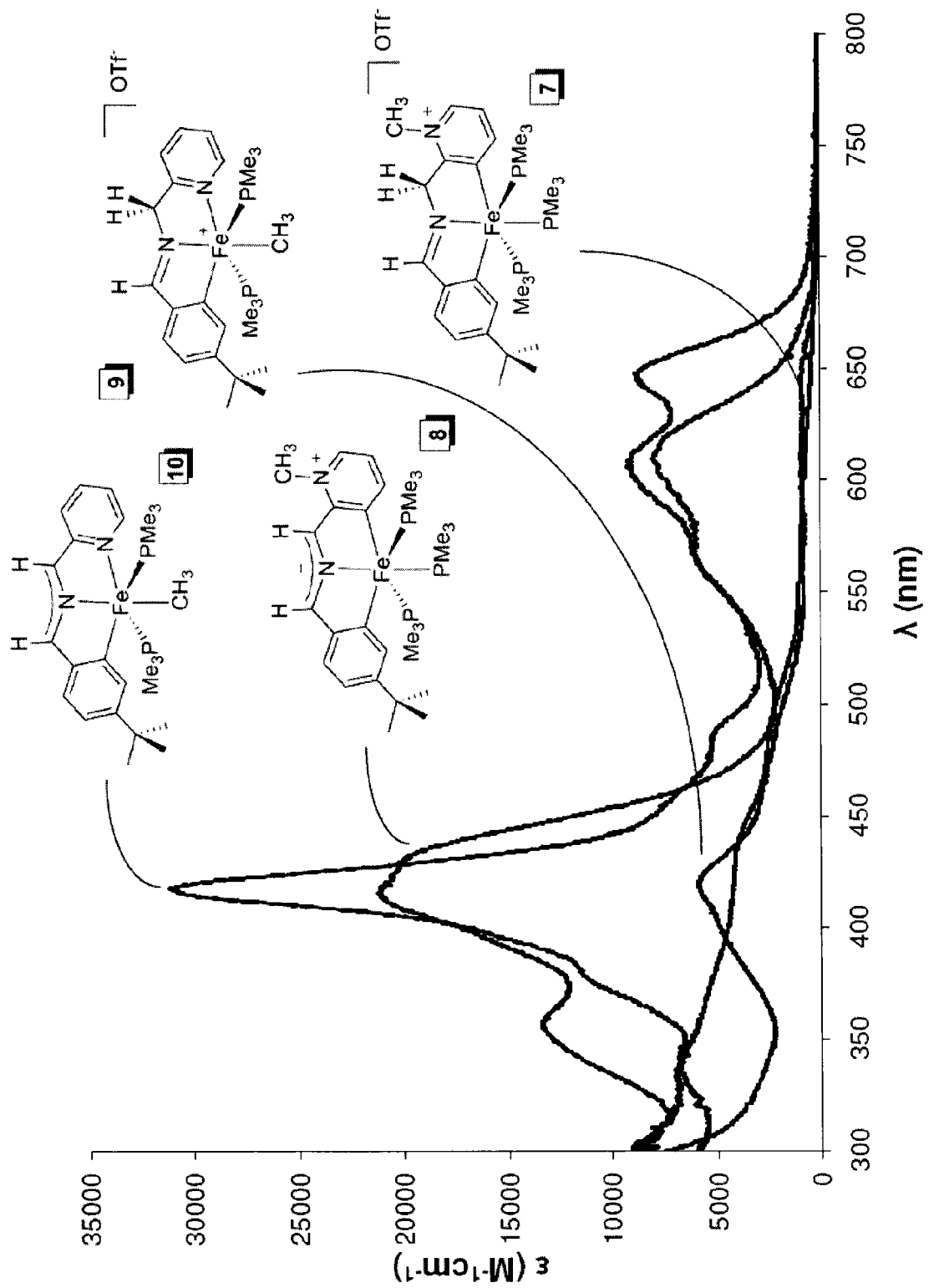
FIG. 4 shows UV-vis spectra for two azaallyl compounds.

The azaallyl ligands of the invention have an A-CR$^1$—N—CR$^2$-A arrangement, which results in a formal negative charge. This is to be distinguished from imine compounds, which have an A-CRR$^1$—N=CR$^2$-A arrangement, resulting in no charge. The two carbons contained in the azaallyl backbone of the invention both demonstrate sp$^2$ hybridization. In an imine, however, one of the carbons is sp$^3$ hybridized. FIG. 4 (described in more detail later) illustrates this distinction quite clearly.

In one aspect, the invention relates to a compound comprising at least one azaallyl moeity, wherein the azaallyl moeity is of formula Ia or Ib:

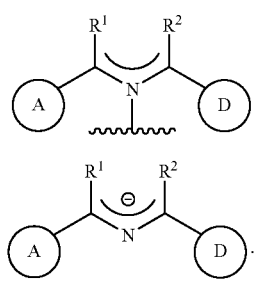

wherein
A is optionally substituted aryl or heteroaryl;
D is optionally substituted aryl or heteroaryl;
⌣ is a delocalized bond;
R$^1$ and R$^2$ are each independently selected from hydrogen, halogen, an optionally substituted (C$_1$-C$_{20}$) hydrocarbon, —C(=O)—R$^{10}$, —C(=O)NR$^{10}$R$^{11}$, —C(=O)OR$^{10}$, —C(=S)NR$^{10}$R$^{11}$, —C(=S)—R$^{10}$ and —C(=S)OR$^{10}$; or
R$^1$ and R$^2$, together with the carbons to which they are attached, may be an optionally substituted non-aromatic ring;
R$^{10}$ and R$^{11}$ are each selected independently from hydrogen, an optionally substituted (C$_1$-C$_{20}$) hydrocarbon and a polar, neutral moeity; and
⤳ represents a coordinate covalent bond to a metal.

In one aspect of the invention, A is an optionally substituted aryl. In some aspects, A is an optionally substituted monocyclic aryl. In some of these aspects, A is optionally substituted phenyl. In another aspect, A is an optionally substituted heteroaryl. In other aspects, A is an optionally substituted monocyclic heteroaryl group. In some of these aspects, A is optionally substituted pyridinyl. In one aspect of the invention, D is an optionally substituted aryl. In some aspects, D is an optionally substituted monocyclic aryl. In some of these aspects, D is optionally substituted phenyl. In another aspect, D is an optionally substituted heteroaryl. In other aspects, D is an optionally substituted monocyclic heteroaryl group. In some of these aspects, D is optionally substituted pyridinyl. In further aspects of the invention, A is optionally substituted with one or more substituents selected from hydrogen, (C$_1$-C$_6$)alkyl, halogen, alkoxy, nitro, nitroso, haloalkyl, haloalkoxy, oxaalkyl, acyl and cyano. In other aspects of the invention, D is optionally substituted with one or more substituents selected from hydrogen, (C$_1$-C$_6$)alkyl, halogen, alkoxy, nitro, nitroso, haloalkyl, haloalkoxy, oxaalkyl, acyl and cyano.

In some aspects of the invention, R$^1$ is hydrogen. In some aspects of the invention, R$^1$ is halogen. In other aspects of the invention, R$^1$ is an optionally substituted (C$_1$-C$_{20}$) hydrocarbon. In some of these aspects, R$^1$ is (C$_1$-C$_6$)alkyl. In still other aspects of the invention, R$^1$ is fluoro(C$_1$-C$_6$)alkyl. In some aspects of the invention, R$^1$ is —C(=O)—R$^{10}$. In other aspects of the invention, R$^1$ is —C(=O)NR$^{10}$R$^{11}$. In other aspects of the invention, R$^1$ is —C(=O)OR$^{10}$. In other aspects of the invention, R$^1$ is —C(=S)NR$^{10}$R$^{11}$. In some aspects of the invention, R$^1$ is —C(=S)—R$^{10}$. In other aspects of the invention, R$^1$ is C(=S)OR$^{10}$.

In some aspects of the invention, R$^2$ is hydrogen. In some aspects of the invention, R$^2$ is halogen. In other aspects of the invention, R$^2$ is an optionally substituted (C$_1$-C$_{20}$) hydrocarbon. In some of these aspects, R$^2$ is (C$_1$-C$_6$)alkyl. In still other aspects of the invention, R$^2$ is fluoro(C$_1$-C$_6$)alkyl. In some aspects of the invention, R$^2$ is —C(=O)—R$^{10}$. In other aspects of the invention, R$^2$ is —C(=O)NR$^{10}$R$^{11}$. In other aspects of the invention, R$^2$ is —C(=O)OR$^{10}$. In other aspects of the invention, R$^2$ is —C(=S)NR$^{10}$R$^{11}$. In some aspects of the invention, R$^2$ is —C(=S)—R$^{10}$. In other aspects of the invention, R$^2$ is C(=S)OR$^{10}$.

In still other aspects of the invention, R$^1$ and R$^2$, together with the carbons to which they are attached, may be an optionally substituted non-aromatic ring.

In some aspects of the invention, R$^{10}$ is hydrogen. In other aspects, R$^{10}$ is an optionally substituted (C$_1$-C$_{20}$) hydrocarbon. In still other aspects, R$^{10}$ is a polar, neutral moeity. In some aspects of the invention, R$^{11}$ is hydrogen. In other aspects, R$^{11}$ is an optionally substituted (C$_1$-C$_{20}$) hydrocarbon. In some aspects, R$^{11}$ is (C$_1$-C$_{20}$) hydrocarbon optionally substituted with fluorine. In still other aspects, R$^{11}$ is a polar, neutral moeity.

When R$^{10}$ and R$^{11}$ are selected from polar, neutral moieties, they can be selected from the group including, but not limited to, alkyls substituted by polar neutral moieties (for example, R$^{10}$ and R$^{11}$ can be —CH$_2$Z, where Z is a polar, neutral moiety such as CH$_2$OR$_a$ or CH$_2$NR$_b$R$_c$); —NR$_b$SO$_2$R$_c$; —CN; —C(=W)R$_a$; —NR$_a$COR$_b$; —NR$_a$CSR$_b$; —SO$_2$NR$_b$R$_c$; —NR$_b$Q$_a$R$_c$; (C=W)NR$_b$R$_c$; C(O)OR$_a$; heterocycle; substituted heterocycle; heteroaryl; and substituted heteroaryl, such as

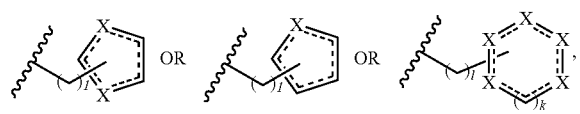

wherein l is 0, 1, 2, 3, 4 or 5; k is 0, 1 or 2; X is C, N, S or O and ═══ represents a single or double bond; R$_a$, R$_b$, R$_c$ are each independently selected from hydrogen; aryl; substituted aryl; heteroaryl; substituted heteroaryl; heterocyclic or substituted heterocyclic; and substituted or unsubstituted alkyl, alkenyl, alkynyl, cycloalkyl, or cycloalkenyl each containing 0, 1, 2, or 3 or more heteroatoms selected from O, S, or N; or alternatively, R$_a$, R$_b$ and R$_c$, taken together with the attached atom form a heterocyclic or substituted heterocyclic; Q$_a$ is absent or selected from (C=O), (SO$_2$), (C=NH), (C=S), or (CONR$_a$); and W is O, S, NOR$_a$ or NR$_a$.

In some aspects, the invention relates to a compound of formula Ia:

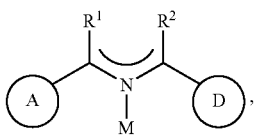

wherein M is a metal. In these instances, M may have additional substituents.

In some aspects, the invention relates to a compound of formula II

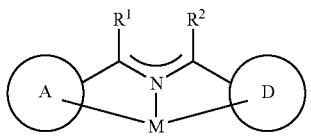

wherein M is a metal that forms additional bonds to A and D. In these instances, M may have additional substituents. In some aspects of the invention, M is lithium. In other aspects of the invention, M is sodium. In still other aspects of the invention, M is magnesium. In certain aspects of the invention, M is titanium. In yet other aspects of the invention, M is vanadium. In some aspects of the invention, M is chromium. In other aspects of the invention, M is manganese. In still other aspects of the invention, M is iron. In yet other aspects of the invention, M is cobalt. In some aspects of the invention, M is nickel. In other aspects of the invention, M is zinc. In still other aspects of the invention, M is molybdenum. In yet other aspects of the invention, M is ruthenium. In some aspects of the invention, M is rhodium. In other aspects of the invention, M is iridium.

In some instances of the invention, M has one additional substituent bond, as shown below in formula IIa:

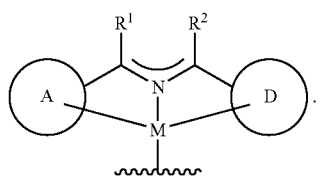

In some instances, the compounds of formula IIa may be as shown below:

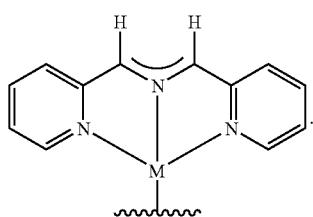

In some instances of the invention, M has three additional substituent bonds as shown below in formula III:

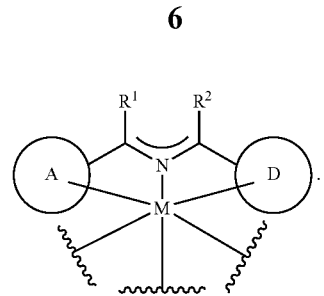

In some instances of the invention, the compounds are of formula IIIa or IIIb:

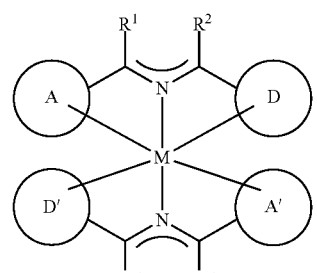

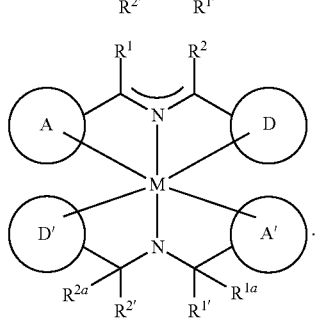

In some aspects of the invention, $R^{1'}$ is hydrogen. In some aspects of the invention, $R^{1'}$ is halogen. In other aspects of the invention, $R^{1'}$ is an optionally substituted ($C_1$-$C_{20}$) hydrocarbon. In some of these aspects, $R^{1'}$ is ($C_1$-$C_6$)alkyl. In still other aspects of the invention, $R^{1'}$ is fluoro($C_1$-$C_6$)alkyl. In some aspects of the invention, $R^{1'}$ is —C(=O)—$R^{10}$. In other aspects of the invention, $R^{1'}$ is —C(=O)N$R^{10}R^{11}$. In other aspects of the invention, $R^{1'}$ is —C(=O)O$R^{10}$. In other aspects of the invention, $R^{1'}$ is —C(=S)N$R^{10}R^{11}$. In some aspects of the invention, $R^{1'}$ is —C(=S)—$R^{10}$. In other aspects of the invention, $R^{1'}$ is —C(=S)O$R^{10}$.

In some aspects of the invention, $R^{2'}$ is hydrogen. In some aspects of the invention, $R^{2'}$ is halogen. In other aspects of the invention, $R^{2'}$ is an optionally substituted ($C_1$-$C_{20}$) hydrocarbon. In some of these aspects, $R^{2'}$ is ($C_1$-$C_6$)alkyl. In still other aspects of the invention, $R^{2'}$ is fluoro($C_1$-$C_6$)alkyl. In some aspects of the invention, $R^{2'}$ is —C(=O)—$R^{10}$. In other aspects of the invention, $R^{2'}$ is —C(=O)N$R^{10}R^{11}$. In other aspects of the invention, $R^{2'}$ is —C(=O)O$R^{10}$. In other aspects of the invention, $R^{2'}$ is —C(=S)N$R^{10}R^{11}$. In some aspects of the invention, $R^{2'}$ is —C(=S)—$R^{10}$. In other aspects of the invention, $R^{2'}$ is C(=S)O$R^{10}$.

In still other aspects of the invention, $R^{1'}$ and $R^{2'}$, together with the carbons to which they are attached, may be an optionally substituted non-aromatic ring.

In some aspects of the invention, $R^{1a}$ is hydrogen. In other aspects of the invention, $R^{1a}$ is $(C_1-C_6)$alkyl. In some aspects of the invention, $R^{2a}$ is hydrogen. In other aspects of the invention, $R^{2a}$ is $(C_1-C_6)$alkyl.

In one aspect of the invention, A' is an optionally substituted aryl. In some aspects, A' is an optionally substituted monocyclic aryl. In some of these aspects, A' is optionally substituted phenyl. In another aspect, A' is an optionally substituted heteroaryl. In other aspects, A' is an optionally substituted monocyclic heteroaryl group. In some of these aspects, A' is optionally substituted pyridinyl. In one aspect of the invention, D' is an optionally substituted aryl. In some aspects, D' is an optionally substituted monocyclic aryl. In some of these aspects, D' is optionally substituted phenyl. In another aspect, D' is an optionally substituted heteroaryl. In other aspects, D' is an optionally substituted monocyclic heteroaryl group. In some of these aspects, D' is optionally substituted pyridinyl. In further aspects of the invention, A' is optionally substituted with one or more substituents selected from hydrogen, $(C_1-C_6)$alkyl, halogen, alkoxy, nitro, nitroso, haloalkyl, haloalkoxy, oxaalkyl, acyl and cyano. In other aspects of the invention, D' is optionally substituted with one or more substituents selected from hydrogen, $(C_1-C_6)$alkyl, halogen, alkoxy, nitro, nitroso, haloalkyl, haloalkoxy, oxaalkyl, acyl and cyano.

In some aspects of the invention, $R^2$ is selected from hydrogen and $(C_1-C_6)$alkyl and, when $R^1$ is —C(=O)—$R^{10}$ or C(=O)NR$^{10}$R$^{10}$ is selected from hydrogen and $(C_1-C_6)$alkyl, and $R^{11}$ is $(C_1-C_{20})$ hydrocarbon optionally substituted with fluorine.

In some instances of formula IIIa or formula IIIb, M is chosen from lithium, sodium, magnesium, titanium, vanadium, chromium, manganese, iron, cobalt, nickel, zinc, molybdenum, ruthenium, rhodium and iridium; A, D, A' and D' are each independently selected from a monocyclic aryl and a monocyclic heteroaryl group; each optionally substituted with one or more substituents selected from hydrogen, $(C_1-C_6)$alkyl, halogen, alkoxy, nitro, nitroso, haloalkyl, haloalkoxy, oxaalkyl, acyl and cyano; $R^1$ and $R^2$ are each independently selected from hydrogen, $(C_1-C_6)$alkyl, —C(=O)—$R^{10}$ and —C(=O)NR$^{10}$R$^{11}$; and $R^{1a}$ and $R^{2a}$ are each independently selected from hydrogen and $(C_1-C_6)$ alkyl.

Figure 1:
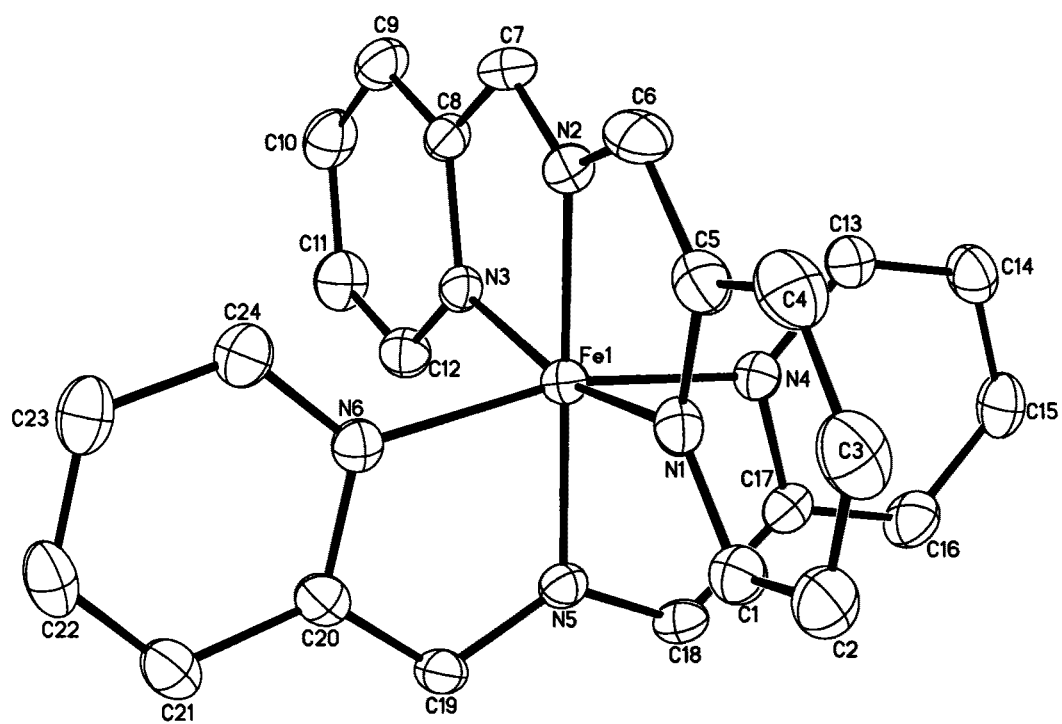
FIG. 1 is a molecular view of $(smif)_2Fe$.
Figure 2:
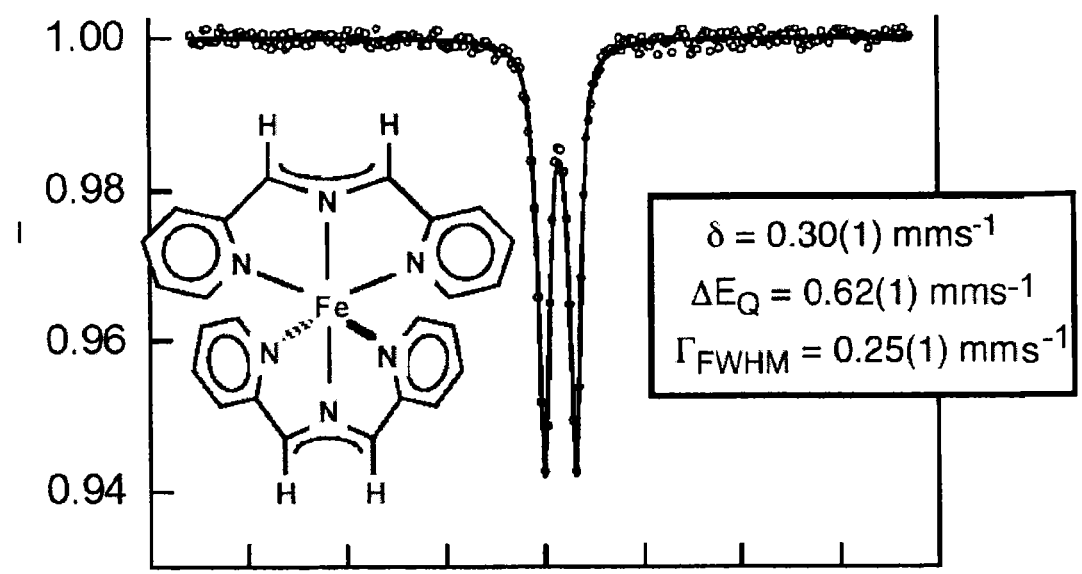
FIG. 2 is a Zero-field Mössbauer spectrum of $(smif)_2Fe$.

One such example of formula IIIa can be found in FIGS. 1 and 2. In this case, A, D, A' and D' are all unsubstituted pyridinyl; $R^1$, $R^2$, $R^{1'}$ and $R^{2'}$ are all hydrogen, and the metal is iron. FIG. 1 shows a molecular view of this combination of substituents [(smif)$_2$Fe]. FIG. 2 illustrates the Zero-field Mössbauer spectrum of (smif)$_2$Fe.

In some instances of formula IIIa or formula IIIb, A, D, A' and D' are each independently chosen from optionally substituted phenyl and optionally substituted pyridinyl; $R^1$ is —C(=O)NR$^{10}$R$^{11}$; $R^2$ is hydrogen or $(C_1-C_6)$alkyl; $R^{10}$ is selected from H and $(C_1-C_6)$alkyl; and $R^{11}$ is $(C_1-C_{20})$ hydrocarbon optionally substituted with fluorine.

In one aspect of the invention, the compounds are of formula

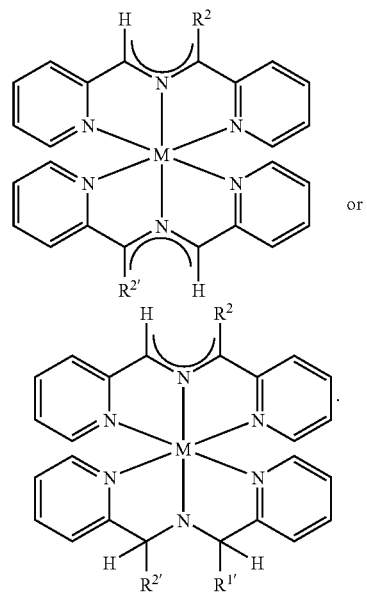

More specifically, the compounds may be of formula

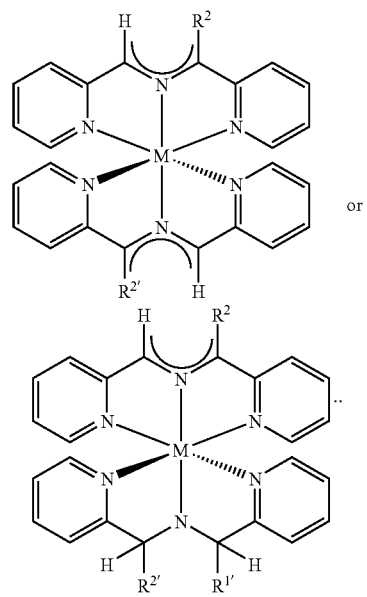

In one aspect, the invention relates to a photovoltaic cell including at least one of the compounds above. In another aspect, the photovoltaic cell includes a metal.

Figure 3:
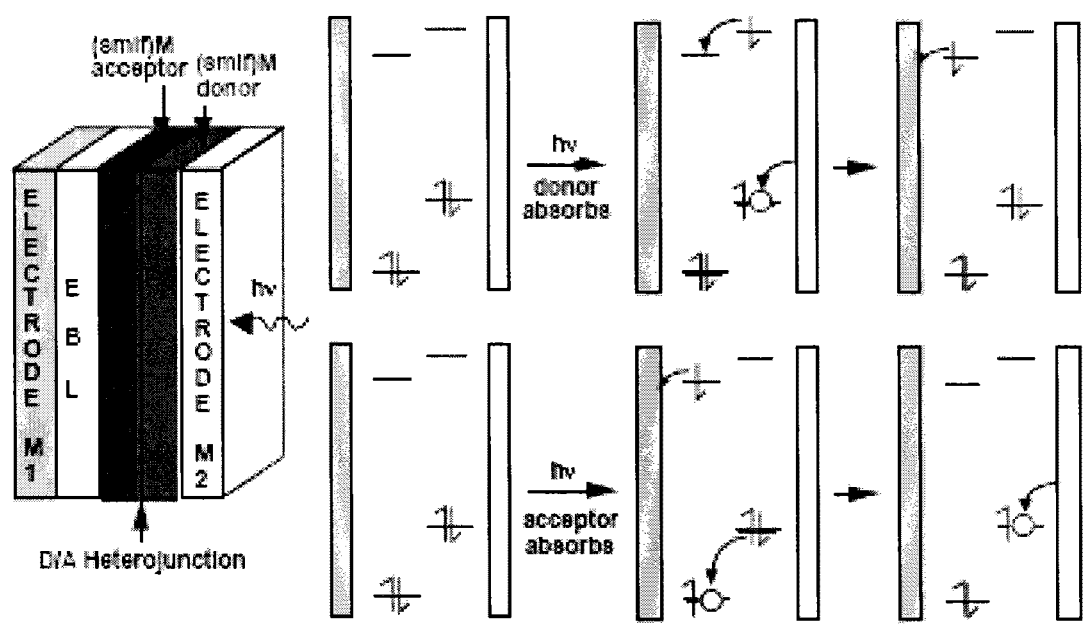
FIG. 3 is a representative Organic Photovoltaic Cell configuration.

FIG. 3 illustrates one configuration of an organic photovoltaic (OPV) device that can be generated using the compounds described herein. As can be seen, two electrodes (an anode and a cathode) flank inner layers containing compounds of the invention ["(smif)M" compounds]: one of these layers acts as a donor, and one acts as an acceptor. There are two potential charge transport mechanisms shown. The first (shaded) shows the absorption of a photon by a donor (D). The exciton (electron/hole pair) thus formed must separate such that the hole is reduced at the anode M2 and the electron must traverse the D/A Heterojunction to eventually reach the cathode M1 (the convention is one of a power source so the electrode that accumulates (+) charge is defined as the anode (M2) and the one accumulating (−) charge is the cathode (M1)). In the second mechanism, penetration of a photon to the acceptor (A) level leads to absorption of a photon and electron transfer from the donor level "seals the hole" in the acceptor, permitting electron transport to the cathode, M1. Several recent cells have used Exciton Blocking Layers (EBL) that help prevent electron/hole recombination by facilitating the separation of charge presumably via the interpenetration of EBL and A layers in the actual device. (Rand, B. P.; Li, J.; Xue, J.; Holmes, R. J.; Thompson, M. E.; Forrest, S. R. *Adv. Mater.* 2005, 17, 2714-2718.) This EBL may or may not be present in OPV configurations of the current invention.

The excitons generated via photon absorption must dissociate into electrons and holes sufficiently close to the D/A heterojunction so that charge separation can be achieved in preference to recombination. Thinner Donor (D) or Acceptor (A) layers permit a higher probability for charge separation closer to the heterojunction, and materials with high optical density, such as the compounds of the current invention, allow for thinner layers. As described, these OPV systems are of the layered type; however, the unique electronic aspects of the complexes herein will also be amenable to a bulk heterojunction approach.

In one aspect, the invention relates to an organic light emitting diode including at least one of the compounds above. In another aspect, the organic light emitting diode includes a metal. As in the OPVs described above, two electrodes (an anode and a cathode) flank an inner layer or layers containing compounds of the invention ["(smif)M" compounds], which can act as electron donors or acceptors. These layers are often referred to as emissive and conductive layers.

In one aspect, the invention relates to a compound having an extinction coefficient of at least 10,000 ($M^{-1}$ $cm^{-1}$) at a wavelength between 400 and 700 nm and containing the element of structure: (aryl or heteroaryl)-C=N—C-(aryl or heteroaryl).

FIG. 4 illustrates optical properties of compounds in accordance with an aspect of the invention. Uv-vis spectra of two exemplary azaallyl complexes, Fe(II) 8 and Fe(III) 10, relative to precursor imines, Fe(II) 7 and Fe(III) 9, are shown that highlight the intensity differences and vibrational progressions associated with the intraligand bands that transfer charge from the $CNC^{nb}$ backbone to the pyridine $\pi^*$ orbitals.

Definitions

Throughout this specification the terms and substituents retain their definitions.

Alkyl is intended to include linear, branched, or cyclic hydrocarbon structures and combinations thereof. A combination would be, for example, cyclopropylmethyl. Hydrocarbon refers to any substituent comprised of hydrogen and carbon as the only elemental constituents. Lower alkyl refers to alkyl groups of from 1 to 6 carbon atoms. Examples of lower alkyl groups include methyl, ethyl, propyl, isopropyl, cyclopropyl, butyl, s- and t-butyl, cyclobutyl and the like. Preferred alkyl groups are those of $C_{20}$ or below. Cycloalkyl is a subset of alkyl and includes cyclic hydrocarbon groups of from 3 to 8 or more carbon atoms. Examples of cycloalkyl groups include c-propyl, c-butyl, c-pentyl, norbornyl and the like.

Alkenyl refers to an unsaturated acyclic hydrocarbon radical in so much as it contains at least one double bond. Such radicals contain from 2 to 10 or more carbon atoms, preferably from 2 to 8 carbon atoms and more preferably 2 to 6 carbon atoms. Examples of suitable alkenyl radicals include propylenyl, buten-1-yl, isobutenyl, penten-1-yl, 2-methyl-buten-1-yl, 3-methylbuten-1-yl, hexen-1-yl, hepten-1-yl, and octen-1-yl, alkadienes and the like.

Alkynyl refers to an unsaturated acyclic hydrocarbon radical in so much as it contains at least one triple bond. Such radicals contain from 2 to 10 or more carbon atoms, preferably from 2 to 8 carbon atoms and more preferably 2 to 6 carbon atoms. Examples of suitable alkynyl radicals include propynyl, butyn-1-yl, pentyn-1-yl, butyn-2-yl, 3-methylbutyn-1-yl, hexyn-1-yl, heptyn-1-yl, and octyn-1-yl and the like.

Cycloalkyl or cycloalkenyl means an alicyclic radical in a ring (or fused ring system) with 3 to 10 carbon atoms, and preferably from 3 to 6 or more carbon atoms. Examples of suitable alicyclic radicals include cyclopropyl, cyclopropenyl, cyclobutyl, cyclopentyl, cyclohexyl, cyclohexenyl and the like.

Oxaalkyl refers to alkyl residues in which one or more carbons has been replaced by oxygen. Examples include methoxypropoxy, 3,6,9-trioxadecyl and the like.

Alkoxy or alkoxyl refers to groups of from 1 to 8 or more carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to four carbons.

Acyl refers to formyl and to groups of 1, 2, 3, 4, 5, 6, 7 and 8 or more carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur, or two hydrogens may be replaced or interrupted by oxygen, as long as the point of attachment to the parent remains at the carbonyl. Examples include acetyl, benzoyl, propionyl, isobutyryl, t-butoxycarbonyl, benzyloxycarbonyl and the like. Lower-acyl refers to groups containing one to six or more, e.g., four carbons.

Aryl and heteroaryl mean a 5- or 6-membered aromatic or heteroaromatic ring containing 0-3 heteroatoms selected from O, N, or S; a bicyclic 9- or 10-membered aromatic or heteroaromatic ring system containing 0-3 heteroatoms selected from O, N, or S; or a tricyclic 13- or 14-membered aromatic or heteroaromatic ring system containing 0-3 heteroatoms selected from O, N, or S. The aromatic 6- to 14-membered carbocyclic rings include, e.g., benzene, naphthalene, indane, tetralin, and fluorene and the 5- to 10-membered aromatic heterocyclic rings include, e.g., imidazole, pyridine, indole, thiophene, thiazole, furan, benzimidazole, quinoline, isoquinoline, quinoxaline, pyrimidine, pyrazine, tetrazole and pyrazole. As used herein aryl and heteroaryl refer to residues in which one or more rings are aromatic, but not all need be.

Arylalkyl or aralkyl means an alkyl residue attached to an aryl ring. Examples are benzyl, phenethyl and the like. Heteroarylalkyl means an alkyl residue attached to a heteroaryl ring. Examples include, e.g., pyridinylmethyl, pyrimidinylethyl and the like.

Heterocycle means a cycloalkyl or aryl carbocycle residue in which from one to three carbons is replaced by a heteroatom selected from the group consisting of N, O and S. The nitrogen and sulfur heteroatoms may optionally be oxidized, and the nitrogen heteroatom may optionally be quaternized. Unless otherwise specified, a heterocycle may be non-aromatic or aromatic. Examples of heterocycles that fall within the scope of the invention include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like. It is to be noted that heteroaryl is a subset of heterocycle in which the heterocycle is aromatic. Examples of heterocyclyl residues additionally include piperazinyl, 2-oxopiperazinyl, 2-oxopiperidinyl, 2-oxo-pyrrolidinyl, 2-oxoazepinyl, azepinyl, 4-piperidinyl, pyrazolidinyl, imidazolyl, imidazolinyl, imidazolidinyl, pyrazinyl, oxazolidinyl, isoxazolidinyl, thiazolidinyl, isothiazolyl, quinuclidinyl, isothiazolidinyl, benzimidazolyl, thiadiazolyl, benzopyranyl, benzothiazolyl, tetrahydrofuryl, tetrahydropyranyl, thienyl, benzothienyl, thiamorpholinyl, thiamorpholinylsulfoxide, thiamorpholinylsulfone, oxadiazolyl, triazolyl and tetrahydroquinolinyl.

As used herein, the term "optionally substituted" may be used interchangeably with "unsubstituted or substituted". The term "substituted" refers to the replacement of one or more hydrogen atoms in a specified group with a specified radical. For example, substituted alkyl, aryl, cycloalkyl, heterocyclyl etc. refer to alkyl, aryl, cycloalkyl, or heterocyclyl wherein one or more H atoms in each residue are replaced with halogen, haloalkyl, alkyl, acyl, alkoxyalkyl, hydroxyloweralkyl, carbonyl, phenyl, heteroaryl, benzenesulfonyl, hydroxy, loweralkoxy, haloalkoxy, oxaalkyl, carboxy, alkoxycarbonyl [—C(=O)O-alkyl], alkoxycarbonylamino [HNC(=O)O-alkyl], carboxamido [—C(=O)NH$_2$], alkylaminocarbonyl [—C(=O)NH-alkyl], cyano, acetoxy, nitro, amino, alkylamino, dialkylamino, (alkyl)(aryl)aminoalkyl, alkylaminoalkyl (including cycloalkylaminoalkyl), dialkylaminoalkyl, dialkylaminoalkoxy, heterocyclylalkoxy, mercapto, alkylthio, sulfoxide, sulfone, sulfonylamino, alkylsulfinyl, alkyl sulfonyl, acylaminoalkyl, acylaminoalkoxy, acylamino, amidino, aryl, benzyl, heterocyclyl, heterocyclylalkyl, phenoxy, benzyloxy, heteroaryloxy, hydroxyimino, alkoxyimino, oxaalkyl, aminosulfonyl, trityl, amidino, guanidino, ureido, benzyloxyphenyl, and benzyloxy. "Oxo" is also included among the substituents referred to in "optionally substituted"; it will be appreciated by persons of skill in the art that, because oxo is a divalent radical, there are circumstances in which it will not be appropriate as a substituent (e.g. on phenyl). In one embodiment, 1, 2 or 3 hydrogen atoms are replaced with a specified radical. In the case of substituted hydrocarbon, more than three hydrogen atoms can be replaced by fluorine; indeed, all available hydrogen atoms could be replaced by fluorine.

The language, "optionally substituted with one or more substituents selected from . . . " implies that a group could be substituted with one or more of one type of substituent or more than one type of substituent. For instance, the language, "aryl optionally substituted with one or more substituents selected from hydrogen, halogen and alkyl," indicates that the aryl could be substituted with, for instance (but not limited to) one hydrogen; three hydrogens; two hydrogens and an ethyl; or one hydrogen, two methyl groups and a fluorine.

The terms "haloalkyl" and "haloalkoxy" mean alkyl or alkoxy, respectively, substituted with one or more halogen atoms. The terms "alkylcarbonyl" and "alkoxycarbonyl" mean —C(=O)alkyl or —C(O)alkoxy, respectively.

The term "halogen" means fluorine, chlorine, bromine or iodine. In one embodiment, halogen may be fluorine or chlorine.

"Metal" refers to any alkali metal, alkaline earth metal, transition metal (including lanthanide or actinide) or semimetal, for the purposes of this application. To be absolutely clear, "metal" can be any Group IA (IUPAC Group 1) element except hydrogen; any Group IIA (IUPAC Group 2) or IIIA (IUPAC Group 13) element, any Group IVA (IUPAC Group 14) element except carbon, any Group VA (IUPAC Group 15) element except nitrogen or phosphorus; any Group VIA (IUPAC Group 16) element except oxygen, sulfur or selenium; or any element in Groups IB-VIIIB (IUPAC Groups 3-12). Representative metals include, but are not limited to, lithium, boron, magnesium, titanium, gallium, germanium, strontium, molybdenum, tin, antimony, lanthanum, iridium, mercury, lead and thorium. It is important to note that the designation of "M" in this application can represent neutral or cationic forms of a given metal atom. Obviously, if the M is cationic, there is a counterion, the nature of which is not critical to the function of the complex. For instance, O-triflate and tetraphenylborate are non-limiting examples of a suitable counterion for a cationic M.

A delocalized bond (designated by ⊖ ) is one in which the electron density is spread over several atoms. The electrons of a delocalized bond (delocalized electrons) are contained within an orbital that may extend over several atoms, and are not solely associated with one atom covalent bond. For instance, the pictorial rendering shown below would represent such a bond:

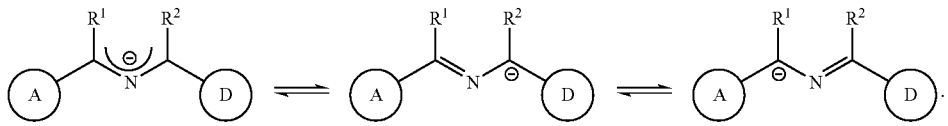

The azaallyl ligands of the invention have an A-CR$^1$—N—CR$^2$-A arrangement, which results in a formal negative charge. This is to be distinguished from imine compounds, which have an A-CRR$^1$—N=CR$^2$-A arrangement, resulting in no charge. The carbons contained in the azaallyl backbone of the invention both demonstrate sp$^2$ hybridization. In an imine, however, one of the carbons is sp$^3$ hybridized.

Many bonds in the compounds of this invention may be considered coordinate covalent bonds. In these cases, both shared-pair electrons are provided by one atom (the donor). This serves to form a coordination complex. As can be seen in many of the compounds of this invention, often the acceptor is a metal atom. Once the coordinate covalent bond has formed, the strength of the bond is the same as that of a covalent bond; therefore, for purposes of this application, there is not always a special demarcation for a coordinate covalent bond. However, in some cases, a coordinate covalent bond will be represented by ------ .

Substituents R″ are generally defined when introduced and retain that definition throughout the specification and in all independent claims.

Abbreviations

A comprehensive list of abbreviations utilized by organic chemists (i.e. persons of ordinary skill in the art) appears in the first issue of each volume of the *Journal of Organic Chemistry*. The list, which is typically presented in a table entitled "Standard List of Abbreviations", is incorporated herein by reference. The following abbreviations and terms have the indicated meanings throughout:

DME=ethylene glycol dimethyl ether
dpma=N,N-di(pyridinyl-α-methyl)-N-methylamine
Et=ethyl
LiHMDS=Lithium bis(trimethylsilyl)amide ($[(CH_3)_3Si]_2NLi$)
Me=methyl
py=pyridine
smif=(2-py)CHNCH(2-py) [or dipyridylazaallyl]
Tf=triflate
THF=tetrahydrofuran
TMS=trimethylsilyl "smif" refers to the following moiety:

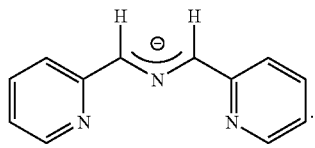 [SMILES: c1ccc(CNCc2ccccn2)nc1]

The following schemes describe the syntheses of exemplary compounds of the invention. The imine-containing compounds shown in the schemes are precursors to the claimed azaallyl-containing compounds.

Certain compounds of the invention were prepared by synthesizing two smif moieties with various transition metals (designated "(smif)$_2$" and the metal name):

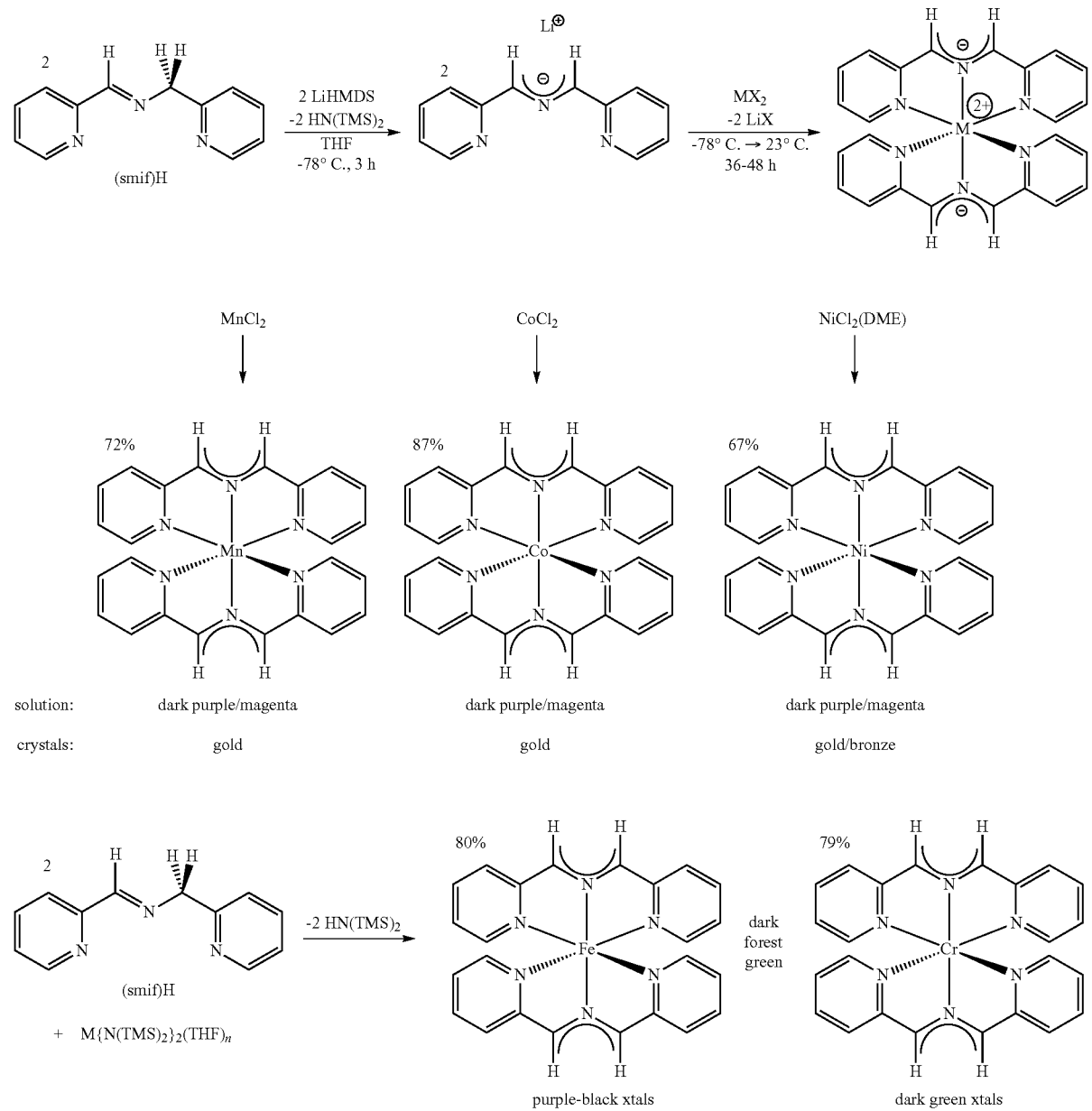

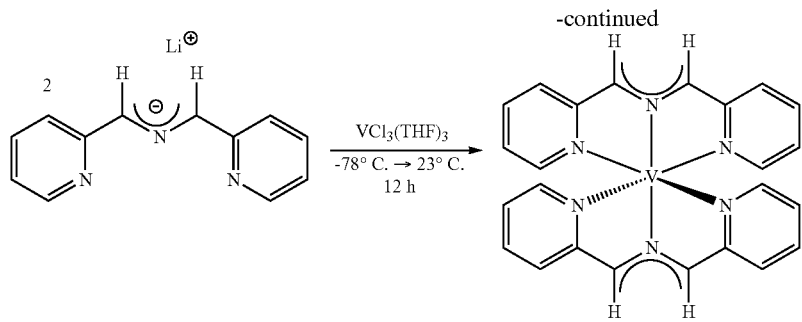
The preparation of various substituted pyridines are shown in Scheme 2:
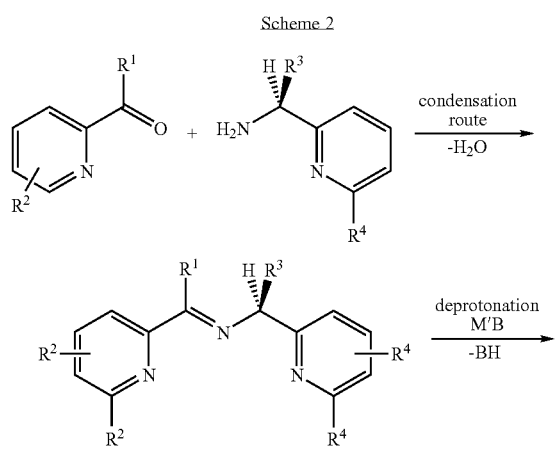
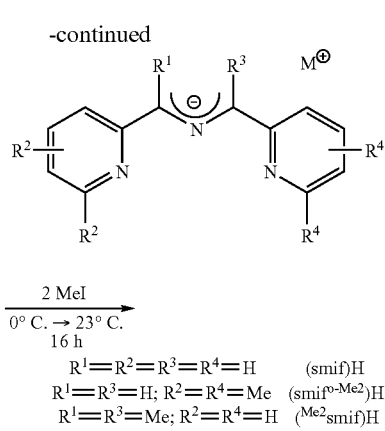
The preparation of various substituted phenyls are shown below in Scheme 3:
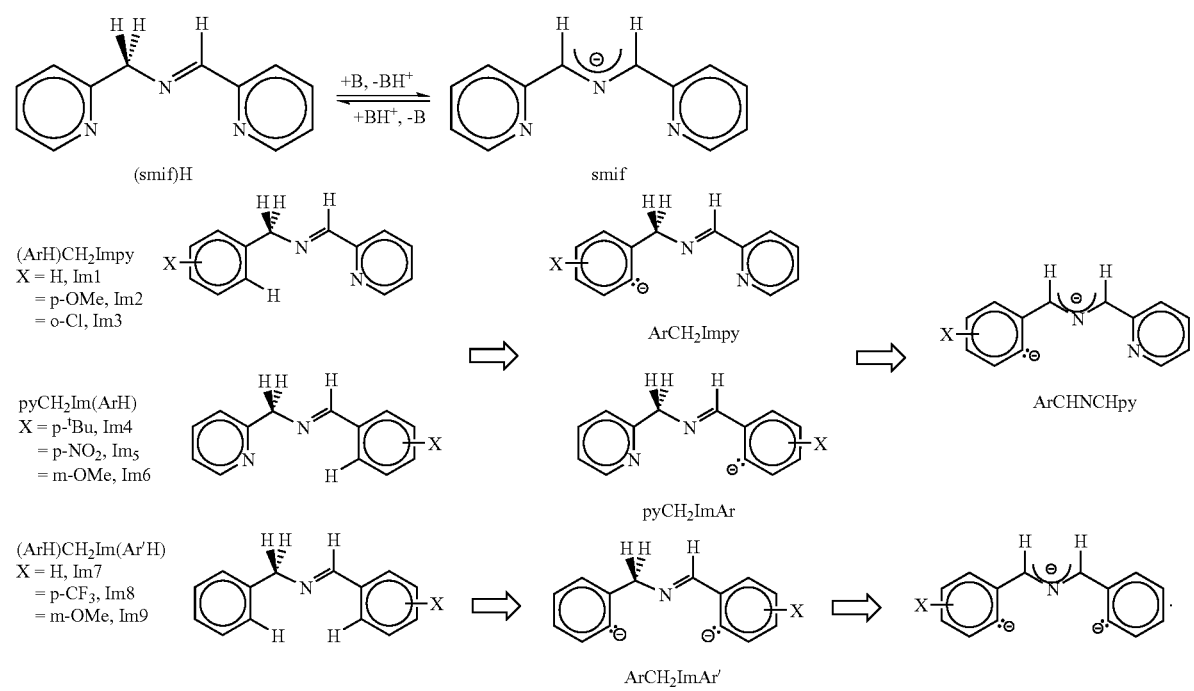

The parent imine is shown on the left, while the representative claimed azaallyl compounds are on the right.

Tables N1 and N2 (shown below) show NMR spectral assignments for imine and imine-derived complexes:

TABLE N1

$^1$H and $^{31}$P{$^1$H} NMR spectral assignments ($\delta$ (J (Hz), assnm't)$^{a,b}$ for imine and imine-derived complexes.

| | |
|---|---|
| 1 | 9.01 (s, a), 7.04 (m, c), 7.00 (t, 5, d), 6.87 (m, e), 8.63 (d, 5, f), 7.21 (d, 5, i), 7.04 (m, j), 7.10 (t, 8, k), 6.92 (d, 5, l), 4.91 (s, n), 0.38 (s, o), 1.52 (t, 12, p); 6.37 (s, PMe$_3$, o) |
| 2 | 9.00 (s, a), 7.01 (m, c), 6.66 (d, 8, d), 6.58 (dd, 3, 6, e), 8.62 (d, 5, f), 7.01 (m, i), 7.13 (d, 8, k), 6.93 (d, 7, l), 4.94 (t, 4, n), 0.39 (t, 4, o), 1.47 (t, 14, p), 3.59 (s, OMe, q); 6.68 (s, PMe$_3$, o) |
| 3 | 8.93 (s, a), 7.04 (t, 5, c), 6.80 (t, 8, d), 6.72 (m, e), 8.46 (d, 5, f), 6.96 (m, i), 6.87 (m, j), 6.96 (m, k), 5.24 (t, 5, n), 0.33 (t, 5, o), 1.36 (t, 15, p); 8.44 (s, PMe$_3$, o) |
| 4 | 4.42 (s, a), 6.14 (m, c), 6.59 (t, 8, d), 6.14 (m, e), 8.05 (d, 5, f), 8.75 (s, i), 7.11 (d, 10, k), 7.57 (d, 10, l), 7.90 (s, n), 0.69 (s, o), −0.23 (t, 10, p), 1.52 (s, q); 22.84 (s, PMe$_3$, o) |
| 5-Et | 9.18 (s, a), 7.05 (d, 8, c), 7.12 (t, 7, d), 7.20 (t, 6, e), 9.23 (d, 6, f), 0.49 (s, o), 1.29 (t, 13, p), −0.01 (t, 11, s), 3.96 (t, 7 t), 2.16 ("sx", 8, u(CH$_2$)), 1.11 (t, 7, u(CH$_3$)), −0.59 (s, PMe$_3$, o) |
| 5-$^{neo}$Pe$^c$ | 9.31 (a), 7.03 (c), 7.13 (d), 7.20 (e), 9.46 (f), 0.51 (s, o), 1.12 (p), 0.13 (s), 3.80 (t), 1.28 (u); −1.43 (s, PMe$_3$, o) |
| 6 | 5.03 (br s, a), 8.40 (d, 2, d), 6.86 (dd, 8, 2, e), 7.91 (d, 8, f), 8.09 (s, i), 7.03 (d, 8, k), 7.34 (d, 8, l), 7.86 (br s, n), 0.55 (t, 4, o), 1.32 (d, 8, p), 1.43 (s, q); 24.77 ("t",$^d$ 61, PMe$_3$, p), 19.60 (d, 61, PMe$_3$, o) |
| 7$^e$ | 5.47 (s, a), 7.87 (d, 6, d), 7.01 (t, 7, e), 8.34 (d, 7, f), 8.02 (s, i), 6.92 (d, 8, k), 7.40 (d, 8, l), 8.68 (br s, n), 0.80 (t, 3, o), 1.58 (d, 5, p), 1.33 (s, q), 4.14 (s, r); 23.02 ("t",$^d$ 61, PMe$_3$, p), 18.82 (d, 61, PMe$_3$, o) |
| 8 | 5.84 (s, a), 6.73 (d, 6, d), 5.51 (t, 6, e), 5.80 (d, 6, f), 8.06 (s, i), 7.03 (d, 8, k), 7.18 (d, 8, l), 7.37 (s, n), 0.99 (s, o), 1.33 (d, 6, p), 1.50 (s, q), 2.38 (s, r); 27.33 ("t",$^d$ 59, PMe$_3$, p), 20.74 (d, 59, PMe$_3$, o) |
| 9$^{e,f}$ | 40.80 (1H), 28.75 (1H), 19.88 (1H), 16.92 (1H), 13.35 (2H, a), 1.29 (1H), 1.16 (9H, q), −0.46 (1H), −5.22 (3H), −15.30 (18H, o), −55.30 (1H) |
| 10$^{e,f}$ | 30.12 (1H), 22.03 (1H), 13.76 (1H), 12.73 (1H), 1.91 (9H, q), 1.77 (3H), −1.71 (1H), −1.97 (1H), −12.36 (1H), −14.39 (18H, o), −27.00 (1H), −47.97 (1H) |
| 11$^g$ | 4.79 (s, a), 7.03 (d, 8, c), 7.11 (t, 7, d), 7.12 (t, 7, e), 7.81 (d, 7 f), 8.13 (d, 8, i), 7.18 (m, j), 7.18 (m, k), 7.46 (d, 8 l), 8.02 (br s, n), 0.59 (s, o), 1.33 (d, 6, p); 23.73 ("t",$^d$ 61, PMe$_3$, p), 19.43 (d, 61, PMe$_3$, o) |
| 12 | 4.74 (br s, a), 7.00 (d, c), 7.11 (t, d), 7.14 (m, e), 7.73 (d, f), 8.51 (s, i), 7.28 (m, k), 7.28 (m, l), 7.94 (br s, n), 0.47 (t, o), 1.30 (d, p); 22.28 ("t",$^d$ 63, PMe$_3$, p), 18.01 (d, 63, PMe$_3$, o) |
| 13 | 4.84 (br s, a), 6.99 (d, 8, c), 7.09 (t, 7, d), 7.13 (m, e), 7.77 (d, 8, f), 7.93 (d, 8, j), 7.18 (m, k), 7.02 (d, 8, l), 8.03 (br s, n), 0.61 (t, 3, o), 1.36 (d, 6, p); 24.16 ("t",$^d$ 62, PMe$_3$, p), 19.51 (d, 62, PMe$_3$, o) |
| 14$^h$ | 143.78 (2H, n), 37.27 (1H), 28.61 (1H), 17.42 (1H), 17.36 (1H), −14.21 (18H, o), −15.99 (9H, p), −22.59 (1H), −34.30 (1H), −36.32 (1H), −39.96 (1H), −56.33 (1H) |

$^a$Benzene-d$_6$ unless otherwise noted.
$^b$Assignments for 7 were made based on HMBC and NOESY; assignments for the remaining compounds were made analogously, by comparison to literature species, or via COSY (12).
$^c$Signals broad; coupling not resolved.
$^d$Actually appears as a non-first order dd in A$_2$B spin system; shifts and J$_{PP}$ determined from simulation.
$^e$THF-d$_8$.
$^f$Paramagnetic spectra were assigned only on the basis of integrated intensity.
$^g$Assignments are for structure with N=C(a).
$^h$CD$_2$Cl$_2$.

TABLE 2

$^{13}$C{$^1$H} NMR spectral assignments ($\delta$, J$_{PC}$ (Hz), assnm't)$^{a,b,c}$ for imine and imine-derived complexes.

| | |
|---|---|
| 1 | 153.23 (a), 161.93 (b), 124.21 (t, 4, c), 126.93 (d), 120.61 (t, 1, e), 152.99 (f), 178.48 (t, 37, h), 140.31 (t, 4, i), 120.83 (t, 3, j), 121.49 (k), 117.94 (t, 3, l), 152.17 (m), 70.26 (n), 10.77 (t, 10, o), −4.61 (t, 33, p) |
| 2 | 157.15 (a), 161.89 (b), 125.39 (t, 3, c), 126.98 (d), 120.52 (t, 3, e), 152.98 (f), 181.67 (t, 37, h), 145.58 (t, 1, i), 106.42 (j), 121.51 (k), 117.76 (t, 3, l), 152.12 (m), 69.67 (n), 10.84 (t, 11, o), −4.34 (t, 33, p), 54.83 (q) |
| 3 | 149.43 (a), 161.70 (b), 125.54 (t, 4, c), 127.53 (d), 120.40 (t, 3, e), 152.61 (f), 185.33 (h), 138.52 (i), 120.77 (j), 121.65 (k), 125.22 (l), 152.60 (m), 70.25 (n), 10.68 (o), −4.38 (t, 33, p) |
| 4 | 61.08 (a), 165.02 (b), 122.05 (c), 128.78 (d), 116.36 (e), 151.59 (f), 190.17 (h), 141.76 (i), 146.88 (j), 116.60 (k), 123.46 (l), 152.04 (m), 163.51 (n), 11.35 (o), −10.00 (p), 35.41 (CMe$_3$, q), 32.37 (C(CH$_3$)$_3$, q) |
| 6 | 66.23 (a), 172.55 (b), 141.97 (d), 120.57 (e), 150.09 (f), 178.00 (g), 201.77 (h), 142.78 (i), 148.34 (j), 117.12 (k), 126.22 (l), 151.51 (m), 170.09 (n), 17.59 (o), 23.84 (p), 35.12 (CMe$_3$, q), 32.42 (C(CH$_3$)$_3$, q) |
| 7$^d$ | 62.62 (a), 166.37 (b), 155.57 (d), 122.11 (e), 135.28 (f), 182.50 (g), 196.53 (h), 143.00 (i), 149.91 (j), 118.40 (k), 127.05 (l), 152.07 (m), 173.66 (n), 17.42 (t, 11, o), 23.26 (d, 16, p), 35.48 (CMe$_3$, q), 32.27 (C(CH$_3$)$_3$, q), 46.60 (r) |
| 8 | 108.95 (a), 160.77 (b), 145.20 (d), 121.20 (e), 135.80 (t, 3, f), 190.15 (td, 13, 19, g), 195.10 (td, 10, 25 h), 142.26 (i), 148.24 (d, 3, j), 117.56 (k), 127.31 (l), 154.22 (d, 5, m), 106.78 (n), 17.44 (td, 2, 10, o), 23.73 (d, 15, p), 34.88 (CMe$_3$, q), 32.59 (C(CH$_3$)$_3$, q), 41.39 (r) |
| 11$^e$ | 168.70 (t, 4, a), 151.86 (b), 125.87 (c), 116.13 (t, 4, d), 140.17 (e), 143.99 (f), 206.41 (m, g), 183.21 (m, h), 118.57 (i), 120.98 (t, 3, j), 141.44 (k), 124.71 (t, 3, l), 157.37 (m), 66.48 (n), 23.76 (d, 15, o), 17.63 (t, 10, p) |
| 12$^f$ | 66.48 (a), 157.37 (b), 124.71 (t, 3, c), 141.44 (d), 120.98 (t, 3, e), 118.57 (t, 2, f), 183.21 (m, g), 206.41 (m, h), 143.99 (i), 140.17 (j), 116.13 (t, 4, k), 125.87 (l), 151,86 (m), 168.70 (t, 4, n), 23.34 (td, 3, 16, o), 17.30 (td, 3, 11, p) |

$^a$Benzene-d$_6$ unless otherwise noted.
$^b$Assignments for 7 were made based on HMBC and NOESY; assignments for the remaining compounds were made analogously or by comparison to literature species.
$^c$J$_{PC}$ are given when the resolution and signal-to-noise permitted an unambiguous assessment.
$^d$THF-d$_8$.
$^e$Assignments are for structure with N=C(a).
$^f$Signal for CF$_3$ (q) not located.

Schemes 4 and 5 below illustrate intermediates that may be generated while making the compounds of the invention. None of the compounds of Schemes 4 and 5 are intended to fall within the claims.

Scheme 4

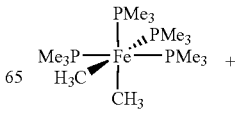 +

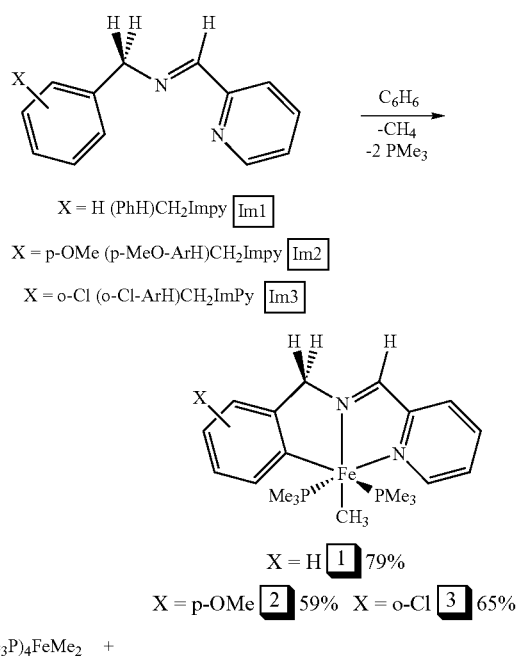
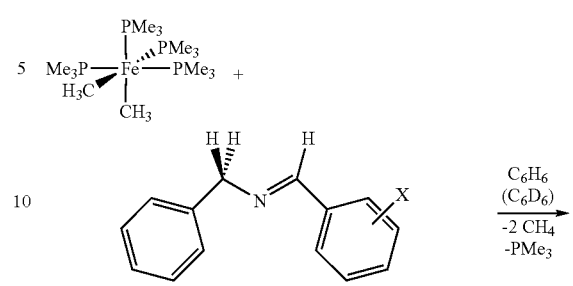
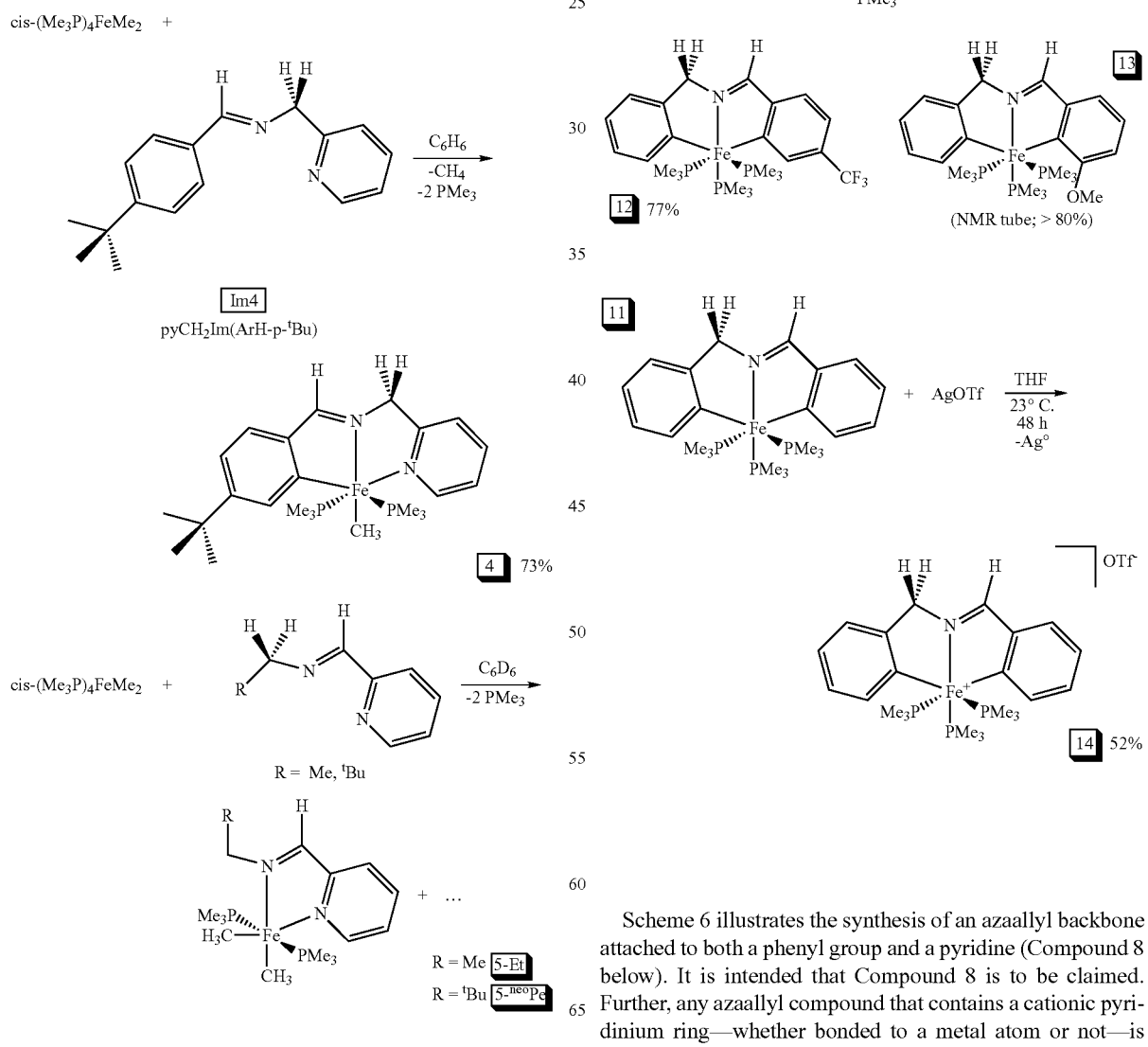
Scheme 6 illustrates the synthesis of an azaallyl backbone attached to both a phenyl group and a pyridine (Compound 8 below). It is intended that Compound 8 is to be claimed. Further, any azaallyl compound that contains a cationic pyridinium ring—whether bonded to a metal atom or not—is intended to be claimed.

Scheme 6
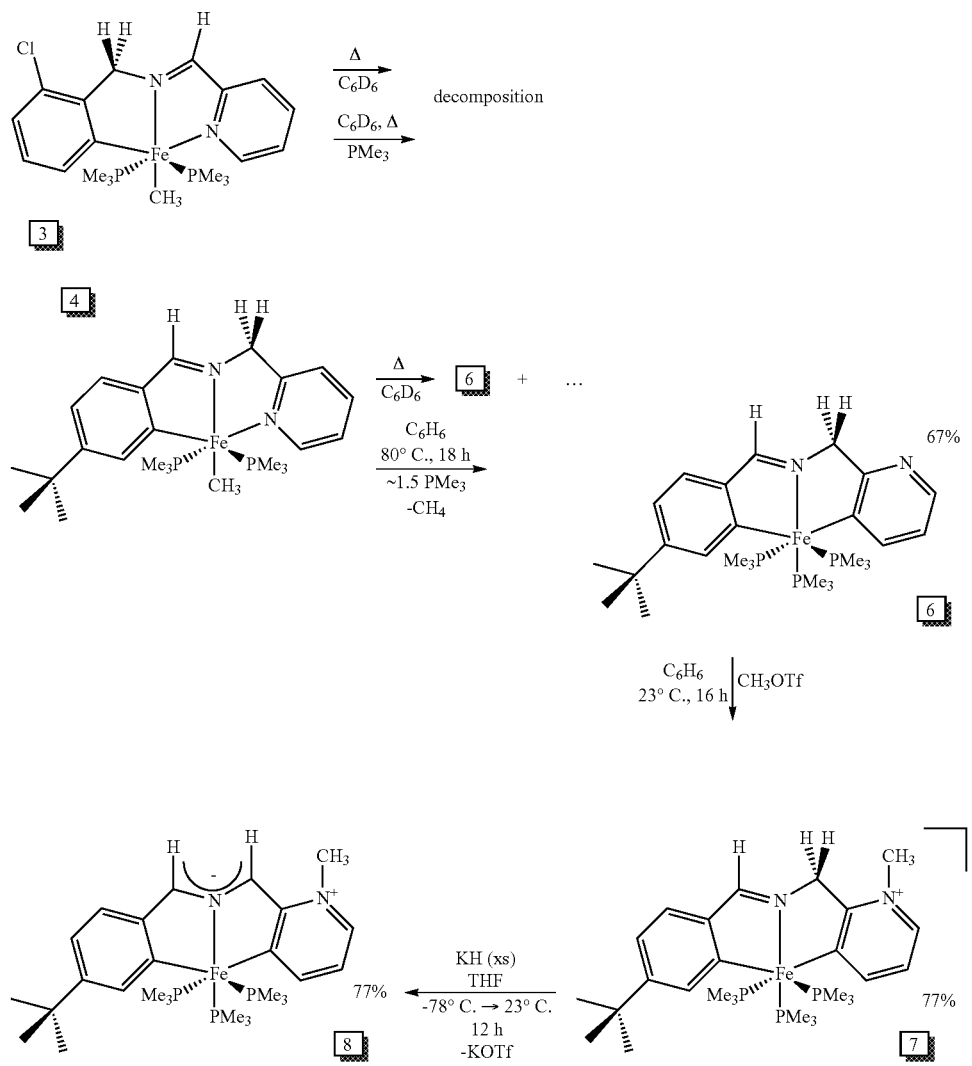
Scheme 7 shows an example of the synthesis of the azaallyl backbone attached to both a phenyl group and a pyridine. Compound 10 in this Scheme falls within the claims of this invention:
Scheme 7
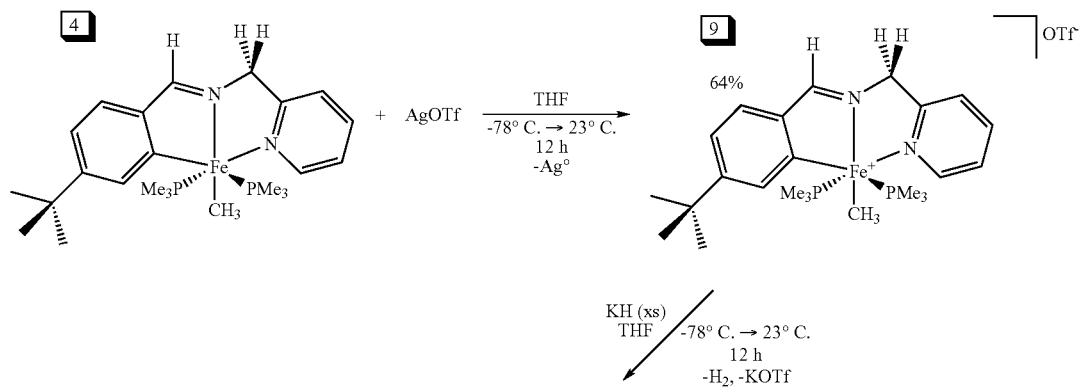

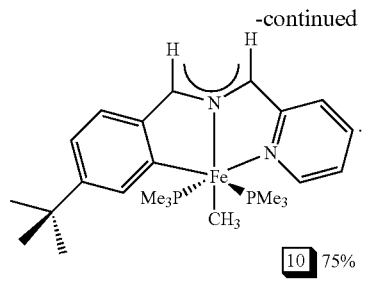

[10] 75%

General Procedure for Synthesis of Imines Im1-Im9. To a suspension of MgSO$_4$ (5-8 equiv) in CH$_2$Cl$_2$ were added 1.5 mmol aldehyde and 1.5 mmol amine. After stirring for 2 h, the mixture was filtered and concentrated to yield a clear to pale yellow oil in >98% purity (by $^1$H NMR). Spectra and syntheses the starting materials can be found in literature references Im1, Im2, Im5, and Im7. Im3: $^1$H NMR (C$_6$D$_6$, 300 MHz): 8.53 (s, a), 8.10 (d, 8, c), 7.02 (t, 8, d), 6.62 (dd, 5, 8, e), 8.47 (d, 5, f), 7.18 (d, 8, h), 6.91 (t, 8, i), 6.79 (t, 8, j), 7.29 (d, 8, k), 4.71 (s, n). $^{13}$C NMR (C$_6$D$_6$, 300 MHz): 164.65 (a), 155.82 (b), 124.96 (c), 136.35 (d), 127.32 (e), 149.96 (f), 130.46 (h), 129.86 (j), 121.34 (k), 134.16 (l), 137.84 (m), 62.21 (n). *One signal obscured by solvent peak. Im4: $^1$H NMR (C$_6$D$_6$, 300 MHz): 5.00 (s, a), 7.39 (d, 8, c), 7.12 (d, 6, d), 6.65 (t, 6, e), 8.53 (d, 5, J), 7.78 (d, 8, h, l), 7.28 (d, 8, i, k), 8.10 (s, n), 1.17 (s, r). $^{13}$C NMR (C$_6$D$_6$, 300 MHz): 67.55 (a), 160.97 (b), 122.50 (c), 134.90 (d), 122.13 (e), 149.86 (f), 126.09 (i), 154.30 (j), 126.09 (k), 136.45 (m), 162.86 (n), 35.15 (q), 31.58 (r). *Two signals obscured by solvent peak. Im6: $^1$H NMR (C$_6$D$_6$, 300 MHz): 5.00 (s, a), 7.34 (d, 8, c), 7.08 (t, 8, d), 6.64 (dd, 6, 8, e), 8.52 (d, 5, f), 7.55 (s, h), 6.86 (dd, 3, 8, j), 7.12 (t, 8, k), 7.26 (d, 8, l), 8.03 (s, n), 3.28 (s, q). $^{13}$C NMR (C$_6$D$_6$, 300 MHz): 67.42 (a), 160.77 (b), 122.59 (c), 136.51 (d), 122.22 (e), 149.87 (f), 112.59 (h), 160.59 (i), 118.08 (j), 130.08 (k), 122.29 (l), 138.75 (m), 163.02 (n), 55.14 (q). Im8: $^1$H NMR (C$_6$D$_6$, 300 MHz): 4.57 (s, a), 7.28-7.21 (m, c, d, f, g), 7.14 (m, e), 7.32 (d, 8, h, l), 7.52 (d, 8, i, k), 7.80 (s, n). $^{13}$C NMR(C$_6$D$_6$, 300 MHz): 65.48 (a), 140.18 (b), 128.61 (c), 129.04 (d), 127.69 (e), 129.04 (f), 128.61 (g), 129.13 (h, l), 125.96 (q, 6, l, k), 139.95 (m), 160.21 (n). *Two signals not observed. Im9: $^1$H NMR (C$_6$D$_6$, 300 MHz): 4.61 (s, a), 7.32 (d, 8, c,g), 7.20 (t, 7, d,f), 7.11 (t, 8, e), 7.59 (s, h), 6.87 (d, 8, j), 7.08 (t, 7, k), 7.27 (d, 7, l), 8.01 (s, n), 3.27 (s, q). $^{13}$C NMR (C$_6$D$_6$, 300 MHz): 65.54 (a), 140.51 (b), 128.69 (c, g), 129.05 (d, f), 127.47 (e), 112.42 (h), 140.51 (i), 118.13 (j), 130.08 (k), 122.30 (l), 138.83 (m), 161.77 (n), 55.12 (q).

Synthesis of the Imine Complexes. A 100 mL bomb reactor was charged with Fe(PMe$_3$)$_4$Me$_2$ (100-300 mg, 0.256-0.641 mmol) and imine (1 equiv). 15 mL benzene were transferred at −78° C., and the solution was allowed to warm 23° C. and stir for 24 h. Upon removal of solvent, the crude mixture was dissolved in Et$_2$O, filtered and washed (4×10 mL Et$_2$O). Crystallization from hexanes at −78° C. afforded product. a. trans-{κ-C,N,N'-(Ph-2-yl)CH$_2$N=CH-2-py}(PMe$_3$)$_2$FeCH$_3$ (1). Dark green microcrystals (85 mg) were obtained in 79% yield. Anal. Calcd. for C$_{20}$H$_{32}$N$_2$P$_2$Fe: C, 57.43; H, 7.71; N, 6.70. Found: C, 56.45; H, 7.36; N: 6.37. b. trans-{κ-C,N,N'-(p-MeO—Ar-2-yl)CH$_2$N=CH-2-py}(PMe$_3$)$_2$FeCH$_3$ (2). Dark green microcrystals (102 mg from 0.383 mmol) were obtained in 59% yield. Anal. Calcd. for C$_{21}$H$_{34}$N$_2$OP$_2$Fe: C, 56.26; H, 7.64; N, 6.25. Found: C, 55.98; H, 7.71; N, 5.96. c. trans-{κ-C,N,N'-(o-Cl—Ar-2-yl) CH$_2$N=CH-2-py}(PMe$_3$)$_2$FeCH$_3$ (3). Dark green crystals (150 mg from 0.512 mmol) were obtained in 65% yield. Anal.

Calcd. for C$_{20}$H$_{31}$N$_2$P$_2$ClFe: C, 53.06; H, 6.90; N, 6.19. Found: C, 52.84; H, 6.62; N, 6.04. d. trans-{κ-C,N,N'-(p-$^t$Bu—Ar-2-yl)CH=NCH$_2$-2-py}(PMe$_3$)$_2$FeCH$_3$ (4). Midnight blue crystals (222 mg 0.641 mmol) were obtained in 73% yield. Anal. Calcd. for C$_{24}$H$_{40}$N$_2$P$_2$Fe: C, 60.76; H, 8.50; N, 5.91. Found: C, 60.48; H, 8.23; N, 5.68. Uv-vis: 266 nm (12,100 M$^{-1}$ cm$^{-1}$), 417 (4,900), 506 (4,600), 613 (8,900). e. {mer-κ-C,N,C'—(Ph-2-yl)CH$_2$N=CH(Ph-2-yl)}Fe (PMe$_3$)$_3$ (11). The brick-red microcrystalline solid (342 mg from 1.02 mmol) was obtained in 70% yield. Anal. Calcd. for C$_{23}$H$_{38}$NP$_3$Fe: C, 57.87; H, 8.02; N, 2.93. Found: C, 57.82; H, 8.09; N, 2.81. Uv-vis: 239 nm (2,100 M$^{-1}$ cm$^{-1}$), 332 (3,900), 375 (1,700), 445 (2,400), 501 (1,000). f. {mer-κ-C,N,C'—(Ph-2-yl)CH$_2$N=CH(Ar-2-yl-4-CF$_3$)}Fe (PMe$_3$)$_3$ (12). The dark pink microcrystalline solid (107 mg from 0.256 mmol) was obtained in 77% yield. Anal. Calcd. for C$_{24}$H$_{37}$NP$_3$F$_3$Fe: C, 52.86; H, 6.84; N, 2.57. Found: C, 54.30; H, 7.03; N, 2.69.

Oxidation to Give the Iron(III) Triflate Complexes. A 25 mL round bottom flask was charged with either trans-{κ-C,N,N'-(p-$^t$Bu—Ar-2-yl)CH=NCH$_2$-2-py}(PMe$_3$)$_2$FeCH$_3$ (4) or {κ-C,N,C'—(Ph-2-yl)CH$_2$N=CH(Ph-2-yl)}Fe(PMe$_3$)$_3$ (11) (typically ~100 mg) and AgOTf (1 equiv). 10 mL THF were vacuum transferred onto the solids at −78° C. The solution was allowed to warm to 23° C. and stir for 12 h (9) or 48 h (14). The solvent was stripped and the resulting residue dissolved in 5 mL THF. After filtration through celite, the solution was layered with Et$_2$—O and cooled to −30° C. to yield a crystalline solid. a. [trans-{κ-C,N,N'-(p-$^t$Bu—Ar-2-yl)CH=NCH$_2$-2-py}(PMe$_3$)$_2$FeCH$_3$]OTf (9). Red-orange crystals (116 mg from 0.291 mmol) were obtained in 64% yield. Anal. Calcd. for C$_{25}$H$_{40}$N$_2$O$_3$P$_2$F$_3$SFe: C, 48.16; H, 6.47; N, 4.49. Found: C, 47.92; H, 6.27; N, 4.34. Uv-vis: 270 nm (18,500 M$^{-1}$cm$^{-1}$), 396 (4,300), 419 (5,300), 490 (2,100), 565 (1,000), 607 (1,100), 646 (1,000). b. [mer-κ-C,N,C'—{(Ph-2-yl)CH$_2$N=CH(Ph-2-yl)}Fe(PMe$_3$)$_3$]OTf (14). Purple crystals (136 mg from 0.418 mmol) were obtained in 52% yield. Anal. Calcd. for C$_{24}$H$_{38}$NO$_3$P$_3$F$_3$SFe: C, 46.02; H, 6.11; N, 2.24. Found: C, 45.94; H, 6.00; N, 2.11.

Synthesis of Iron Aza-allyl Complexes. Iron complex of [mer-{κ-C,N,C'-(p-$^t$Bu—Ar-2-yl)CH=NCH$_2$(2-py-NCH$_3$-3-yl)}(PMe$_3$)$_3$Fe]OTf (7) or [trans-{κ-C,N,N'-(p-$^t$Bu—Ar-2-yl)CH=NCH$_2$-2-py} (PMe$_3$)$_2$FeCH$_3$]OTf (9) (typically 0.160 mmol) and excess KH (26 mg, 0.642 mmol) were weighed into a 25 mL round bottom flask. THF (10 mL) was vacuum transferred at −78° C. The emerald green solution was placed under argon and allowed to warm slowly to room temperature overnight. The solvent was removed and the mixture filtered and washed with Et$_2$O, Subsequent recrystallization from cold hexanes afforded clean product. a. mer-{κ-C,N,C'-(p-$^t$Bu—Ar-2-yl)CHNCH(2-py-NCH$_3$-3-yl)} (PMe$_3$)$_3$Fe (8). Dark green microcrystals (62 mg from 0.215 mmol) were obtained in 61% yield. Anal. Calcd. for C$_{27}$H$_{47}$N$_2$P$_3$Fe: C, 59.13; H, 8.64; N, 5.11. Found: C, 58.88;

H, 8.38; N, 4.89. Uv-vis: 358 nm (13,400 M$^{-1}$cm$^{-1}$), 417 (21,100), 570 (6,000), 613 (7,900). b. trans-{κ-C,N,N'-(p-$^t$Bu—Ar-2-yl)CHNCH-2-py}(PMe$_3$)$_2$FeCH$_3$ (10). Dark blue-green crystals (60 mg) were obtained in 75% yield. Anal. Calcd. for C$_{24}$H$_{39}$N$_2$P$_2$Fe: C, 60.89; H, 8.30; N, 5.92. Found: C, 58.85; H, 8.27; N, 5.53. Uv-vis: 338 nm (5,800 M$^{-1}$cm$^{-1}$), 377 (10,000), 417 (29,200), 485 (4,500), 566 (5,600), 606 (8,600), 646 (8,300).

mer-{κ-C,N,C'-(p-$^t$Bu—Ar-2-yl)CH=NCH$_2$(2-py-3-yl)}(PMe$_3$)$_3$Fe (6). To a 200 mL bomb charged with trans-{κ-C,N,N'-(p-MeO—Ar-2-yl)CH$_2$N=CH-2-py}(PMe$_3$)$_2$FeCH$_3$ (2, 600 mg, 1.26 mmol) were vacuum transferred 30 mL benzene. 1.5 equiv PMe$_3$ (0.20 mL, 1.90 mmol) were transferred via gas bulb. The reaction mixture was heated at 80° C. for 18 h. After cooling, the solvent was stripped and the remainder dissolved in Et$_2$O. The solution was filtered through a fit, washed three times with Et$_2$O, and concentrated. The crude solid was recrystallized from cold pentane/PMe$_3$ (5 mL/0.5 mL) to yield 453 mg golden brown solid (67%). Anal. Calcd. for C$_{26}$H$_{45}$N$_2$P$_3$Fe: C, 58.43; H, 8.49; N, 5.24. Found: C, 58.17; H, 8.21; N, 5.13. Uv-vis: 333 nm (5,300 M$^{-1}$cm$^{-1}$), 369 (3,400), 417 (3,800), 430 (3,500), 496 (1,100), 604 (500), 671(300), 738 (100).

[mer-{κ-C,N,C'-(p-$^t$Bu—Ar-2-yl)CH=NCH$_2$(2-py-NCH$_3$-3-yl)}(PMe$_3$)$_3$Fe]OTf (7). Into a solution of (3) (200 mg, 0.374 mmol) in benzene (20 mL) was syringed methyl triflate (42 μL, 0.374 mmol) under argon. The solution was stirred for 4 h, then allowed to sit for 12 h. The resulting mixture was filtered to yield brown crystals, which were subsequently washed with hexanes (200 mg, 77%). Anal. Calcd. for C$_{28}$H$_{48}$N$_2$O$_3$P$_3$F$_3$SFe: C, 48.14; H, 6.93; N, 4.01. Found: C, 48.01; H, 7.08; N, 3.88. Uv-vis: 336 nm (6,900 M$^{-1}$cm$^{-1}$), 375 (5,300), 437 (4,000), 495 (2,300), 569 (1,000).

NMR Tube Reactions. 20 mg Fe(PMe$_3$)$_4$Me$_2$ (0.051 mmol) were placed into a flame-dried NMR tube which was sealed to a $^{14}/_{20}$ joint and attached to a needle valve. A solution of imine (0.051 mmol) in benzene (0.7 mL) was added to the tube, at which point a color change was observed. The tube was degassed via freeze-pump-thaw and sealed under active vacuum. Loss of starting material was typically complete after 24 h. a. trans,cis-(PMe$_3$)$_2$(CH$_3$)$_2$Fe{κ-N,N'-EtCH$_2$N=CH-2-py} (5-Et). Purple solution. b. trans,cis-(PMe$_3$)$_2$(CH$_3$)$_2$Fe{κ-N,N'-$^{neo}$PeCH$_2$N=CH-2-py} (5-$^{neo}$Pe). Purple solution. c. {mer-κ-C,N,C'-(Ph-2-yl)CH$_2$N=CH(Ar-2-yl-3-OMe)}Fe(PMe$_3$)$_3$ (13). Red solution.

In certain cases, direct alkylation of the smif backbone can be effected. The condensation route can also be used to place substituents on the backbone, and this simple route can lead to a smif-ligand that is totally desymmetrized, i.e., R$^1$≠R$^2$≠R$^3$≠R$^4$. Clearly, a judicious choice of substituted components can permit a wide range of options, especially those desired to change the optical (absorption) properties, increase the solubility and limit the crystallinity of some of these complexes. For instance, the solubility of the species will increase by utilizing long alkyl chains on the aryls/heteroaryls, and—perhaps in combination with desymmetrization—it is expected that liquid or liquid crystalline versions of these compounds will be prepared. Solubility of the species will also be affected by the positions of the substituents on the aryl/heteroaryl components. The person of skill in the art will recognize that the methyl iodide reactions described herein could be replaced by any optionally substituted alkyl halide or sulfate to provide analogous compounds.

General Considerations. Because the products generally tend to be oxygen-sensitive, all manipulations were performed using either glovebox or high vacuum line techniques. Hydrocarbon solvents containing 1-2 mL of added tetraglyme, and ethereal solvents were distilled under nitrogen from purple sodium benzophenone ketyl and vacuum transferred from same prior to use. Benzene-d$_6$ was dried over sodium, vacuum transferred and stored under N$_2$; THF-d$_8$ was dried over sodium benzophenone ketyl. All glassware was oven dried, and NMR tubes for sealed tube experiments were additionally flame-dried under dynamic vacuum.

NMR spectra were obtained using an INOVA-400 spectrometer, and chemical shifts are reported relative to benzene-d$_6$ ($^1$H, δ 7.16; $^{13}$C{$^1$H}, δ 128.39) and THF-d$_8$ ($^1$H, δ 3.58; $^{13}$C, 67.57). Infrared spectra were recorded on a Nicolet Avatar 370 DTGX spectrophotometer interfaced to a IBM PC(OMNIC software). Uv-vis spectra were obtained on a Shimadzu UV-2101 PC interfaced to an IBM PC (UV Probe software). The nature of the compounds makes elemental analyses problematic.

Procedures.

1. (smif)$_2$V: To a 50 mL 3-neck flask charged with lithium bis(trimethylsilyl)amide (0.170 g, 1.02 mmol) and 0.95% Na/Hg (1.288 g, 0.53 mmol) was vacuum transferred 10 mL THF at −78° C. A solution of smifH (0.200 g, 1.01 mmol) in THF (8 mL) was slowly added to the 3-neck flask via a dropping funnel under argon. The solution immediately turned magenta and stirred at −78° C. for 3 h prior to the addition of VCl$_3$(THF)$_3$ (0.189 g, 0.51 mmol). The reaction mixture, which turned cherry red after slowly warming to 23° C. and stirring for 12 h, was degassed and filtered. The volatiles were removed in vacuo, and the microcrystalline solid was triturated and filtered in Et$_2$O to yield 0.185 g of (smif)$_2$V (81%). Anal. Calcd. H$_{20}$C$_{24}$N$_6$V: C, 65.01; H, 4.55; N, 18.95. Found: C, 65.01; H, 4.55; N, 18.95. μ$_{eff}$ (SQUID, 293K)= 3.6μ$_B$.

2. [(smif)$_2$Cr](OTf): To a 25 mL round bottom flask charged with (smif)$_2$Cr (0.300 g, 0.67 mmol) and AgOTf (0.173 g, 0.67 mmol) was vacuum transferred 8 mL Et$_2$O at −78° C., and the reaction mixture became jester green within 5 min. The flask warmed slowly to 23° C. and was stirred for 2 d while a dark green solid precipitated from the pale blue solution. The volatiles were removed in vacuo. Recrystallization of the dark green solid in THF at 80° C. under a blanket of argon for 16 h led to the formation of metallic red crystals of [(smif)$_2$Cr](OTf) (0.309 g, 75%). $^1$H NMR (C$_6$D$_6$, 400 MHz): δ−12.19 (υ$_{1/2}$≈600 Hz, py-CH, 1 H), −3.95 (υ$_{1/2}$≈600 Hz, py-CH, 1 H). μ$_{eff}$(Gouy balance, 295K)=3.56μ$_B$.

3. (smif)$_2$Cr: To a solution of Cr{N(SiMe$_3$)$_2$}$_2$(THF)$_2$ (0.425 g, 0.82 mmol) in 8 mL Et$_2$O was slowly added a solution of smifH (0.325 g, 1.65 mmol) in 10 mL Et$_2$O at 23° C. The solution immediately became dark emerald green. The reaction was degassed, warmed to 23° C., and stirred for 12 h while dark green crystals precipitated from solution. The reaction was concentrated, and the green suspension was filtered to yield 0.288 g of crystalline (smif)$_2$Cr (79%). $^1$H NMR (C$_6$D$_6$, 400 MHz): δ−103.60 (υ$_{1/2}$≈1700 Hz, py-CH, 1 H), −22.67 (υ$_{1/2}$≈1900 Hz, py-CH, 1 H), −19.83 (υ$_{1/2}$≈200 Hz, py-CH, 1 H), 19.35 (υ$_{1/2}$≈130 Hz, CH, 1 H), 22.08 (υ$_{1/2}$≈100 Hz, py-CH, 1 H). Anal. Calcd. H$_{20}$C$_{24}$N$_6$Cr: C, 64.86; H, 4.54; N, 18.91. Found: C, 64.86; H, 4.54; N, 18.91. μ$_{eff}$(SQUID, 293K)=2.8μ$_B$.

4. [(smif)2Mn](OTf): To a 100 mL round bottom flask charged with (smif)2Mn (0.700 g, 1.56 mmol) and AgOTf (0.402 g, 1.56 mmol) was vacuum transferred 50 mL THF at −78° C. The dark magenta-purple solution slowly warmed to 23° C. and darkened to a deeper purple. After stirring at 23° C. for 1.5 d, the volatiles were removed in vacuo resulting in a red-bronze metallic solid which was filtered in toluene and THF. Filtrates were concentrated, cooled to 23° C., and filtered to yield metallic red-bronze microcrystals of [(smif)$_2$Mn](OTf) (0.728 g, 78%). Anal. Calcd. H$_{20}$C$_{25}$N$_6$O$_3$F$_3$SMn: C, 50.34; H, 3.38; N, 16.66; S, 5.38. Found: C, 50.18; H, 5.50; N, 12.75; S, 5.56. $\mu_{eff}$ (Gouy balance, 295K)=4.45

5. (smif)$_2$Mn: To a solution of lithium bis(trimethylsilyl)amide (0.425 g, 2.54 mmol) in 15 mL THF at −78° C. was added dropwise a solution of smifH (0.500 g, 2.53 mmol) in 10 mL THF under argon. The solution immediately turned magenta and stirred at −78° C. for 2 h prior to the addition of MnCl$_2$ (0.160 g, 1.27 mmol). The reaction mixture became deep purple after stirring at 23° C. for 36 h. The volatiles were removed in vacuo, and the solid was dissolved and filtered in toluene. Toluene was removed, and the solid was triturated and filtered in Et$_2$O to isolate metallic gold crystals of (smif)$_2$Mn (0.410 g, 72%). $^1$H NMR (C$_6$D$_6$, 400 MHz): δ−13.52 ($\upsilon_{1/2}$≈1200 Hz, py-CH, 1 H), 48.08 ($\upsilon_{1/2}$≈4100 Hz, py-CH, 1 H). Anal. Calcd. H$_{20}$C$_{24}$N$_6$Mn: C, 64.43; H, 4.51; N, 18.78. Found: C, 64.21; H, 4.40; N, 18.52. $\mu_{eff}$ (SQUID, 293K)=5.8$\mu_B$.

6. (smif)$_2$Fe: A) To a solution of Fe{N(SiMe$_3$)$_2$}$_2$(THF) (0.284 g, 0.63 mmol) in 15 mL Et$_2$O was slowly added a solution of smifH (0.250 g, 1.27 mmol) in Et$_2$O (15 mL) at 23° C. The solution immediately changed from pale green to deep forest green. The reaction was degassed and warmed to 23° C. Black-metallic purple crystals began to precipitate from solution after stirring for 30 minutes. The reaction mixture was stirred for an addition 9.5 h. The volatiles were removed, and the solid was triturated and filtered in Et$_2$O to yield black-metallic purple crystals of (smif)$_2$Fe (0.229 g, 80%). B) A solution of smifH (5.00 g, 25.35 mmol) in 100 mL THF was added dropwise to a solution of lithium bis(trimethylsilyl)amide (4.242 g, 25.35 mmol) in 50 mL THF at −78° C. under argon. The solution turned magenta and was stirred at −78° C. for 3 h prior to the addition of FeBr$_2$(THF)$_2$ (4.561 g, 12.67 mmol). After stirring at 23° C. for 16 h, a purple crystalline solid precipitated from the forest green solution. The volatiles were removed in vacuo, and the residue was dissolved in toluene and filtered. Toluene was removed, and the solid was triturated with Et$_2$O and filtered to yield black-metallic purple crystals of (smif)$_2$Fe (2.980 g, 52%). $^1$H NMR (C$_6$D$_6$, 400 MHz): δ 5.73 (t, py-C$^5$H, 1 H, J=5.9 Hz), 6.11 (d, py-C$^3$H, 1 H, J=7.9 Hz), 6.38 (t, py-C$^4$H, 1 H, J=7.8 Hz), 7.59 (s, CH, 1 H), 7.66 (d, py-C$^6$H, 1 H, J=5.2 Hz). $^{13}$C{$^1$H} NMR(C$_6$D$_6$, 100 MHz): δ 112.19 (CH), 115.64 (py-C$^3$H), 118.34 (py-C$^5$H), 134.68 (py-C$^4$H), 151.81 (py-C$^6$H), 165.65 (py-C$^2$). Anal. Calcd. H$_{20}$C$_{24}$N$_6$Fe: C, 64.30; H, 4.50; N, 18.75. Found: C, 63.76; H, 4.64; N, 17.69.

7. [(smif)$_2$Co](OTf): To a 10 mL round bottom flask charged with 0.200 g (0.44 mmol) (smif)$_2$Co and 0.114 g (0.44 mmol) AgOTf was vacuum transferred 8 mL THF at −78° C. The reaction mixture changed from deep purple to cobalt blue within 5 minutes and slowly warmed to 23° C. After stirring at 23° C. for 12 h, a magenta solid precipitated from solution. The volatiles were removed in vacuo. Recrystallization of the magenta solid in THF at 80° C. under a blanket of argon for 16 h led to the formation of metallic red crystals of [(smif)$_2$Co](OTf) (0.215 g, 81%). $^1$H NMR (THF-d$_8$, 400 MHz): δ 6.55 (t, py-C$^5$H, 1 H, J=6.4 Hz), 6.85 (d, py-C$^3$H, 1 H, J=8 Hz), 7.24 (s, CH, 1 H), 7.28 (t, py-C$^4$H, 1 H, J=7.2 Hz), 7.59 (d, py-C$^6$H, 1 H, J=6.0 Hz). $^{13}$C{$^1$H} NMR (THF-d$_8$, 100 MHz): δ 117.47 (CH), 118.23 (py-C$^3$H), 119.54 (py-C$^5$H), 120.36 (py-C$^4$H), 139.24 (py-C$^6$H), 148.56 (py-C$^2$).

8. (smif)$_2$Co: To a solution of lithium bis(trimethylsilyl)amide (0.425 g, 2.54 mmol) in 15 mL THF at −78° C. was added dropwise a solution of smifH (0.500 g, 2.53 mmol) in 10 mL THF under argon. The reaction solution immediately turned magenta and was stirred at −78° C. for an additional 2 h prior to the addition of CoCl$_2$ (0.165 g, 1.27 mmol). After stirring at 23° C. for 36 h, the solution had darkened to a deep purple-magenta. The volatiles were removed, and the residue was dissolved and filtered in toluene. Toluene was removed in vacuo, and the solid was triturated with Et$_2$O and filtered to yield metallic gold crystals of (smif)$_2$Co (0.501 g, 87%). $^1$H NMR(C$_6$D$_6$, 400 MHz): δ 10.06 ($\upsilon_{1/2}$≈50 Hz, CH, 1 H), 37.63 ($\upsilon_{1/2}$≈70 Hz, py-CH, 1 H), 39.90 ($\upsilon_{1/2}$≈80 Hz, py-CH, 1 H), 85.19 ($\upsilon_{1/2}$≈140 Hz, py-CH, 1 H), 108.94 ($\upsilon_{1/2}$≈480 Hz, py-CH, 1 H). Anal. Calcd. (for (smif)$_2$Co.(C$_7$H$_8$)$_{0.5}$) H$_{24}$C$_{27.5}$N$_6$CO: C, 66.40; H, 4.86; N, 16.89. Found: C, 65.92, 64.99; H, 4.68, 4.47; N, 17.23, 16.92. $\mu_{eff}$ (SQUID, 10K)=1.7$\mu_B$ and $\mu_{eff}$ (SQUID, 293K)=2.8$\mu_B$.

9. (smif)$_2$Ni: A solution of lithium bis(trimethylsilyl)amide (0.425 g, 2.54 mmol) in 15 mL THF under argon at −78° C. was slowly treated with a solution of smifH (0.500 g, 2.53 mmol) in THF (10 mL). The solution instantly turned magenta and was stirred at −78° C. for 2 h prior to the addition of NiCl$_2$(dme) (0.278 g, 1.27 mmol). After stirring at 23° C. for 36 h, the volatiles were removed in vacuo from the magenta reaction mixture. The solid was dissolved and filtered in toluene. Toluene was removed, and the solid was triturated and filtered in Et$_2$O to yield metallic gold crystals of (smif)$_2$Ni (0.385 g, 67%). $^1$H NMR (C$_6$D$_6$, 400 MHz): δ 9.40 ($\upsilon_{1/2}$170 Hz, CH, 1 H), 51.75 ($\upsilon_{1/2}$≈400 Hz, py-CH, 1 H), 57.01 ($\upsilon_{1/2}$≈470 Hz, py-CH, 1 H), 140.85 ($\upsilon_{1/2}$≈3300 Hz, py-CH, 1 H), 248.32 ($\upsilon_{1/2}$≈6200 Hz, py-CH, 1 H). Anal. Calcd. (for (smif)$_2$Ni.(C$_6$H$_6$)$_{0.5}$) H$_{23}$C$_{27}$N$_6$Ni: C, 66.15; H, 4.73; N, 17.14. Found: C, 65.52; H, 4.61; N, 17.13. $\mu_{eff}$ (SQUID, 293K)=2.8$\mu_B$.

10. (smif)$_2$Mg:

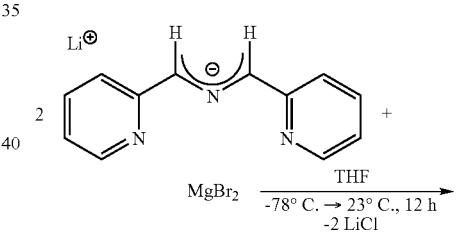

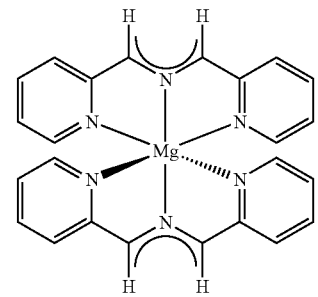

To a 25 mL round bottom flask charged with MgBr$_2$ (0.091 g, 0.49 mmol) and Lismif (0.200 g, 0.98 mmol) was vacuum transferred 10 mL THF at −78° C. resulting in a deep magenta solution which was slowly warmed to 23° C. After the solution stirred for 12 h, the volatiles were removed in vacuo. The solid was triturated with Et$_2$O (3×5 mL) and filtered to yield (smif)$_2$Mg as a microcrystalline gold solid (0.140 g, 68%). $^1$H NMR (C$_6$D$_6$, 400 MHz): δ 5.82 (dd, py-C$^5$H, 1 H, J=6.3, 1.0 Hz), 6.46 (d, py-C$^3$H, 1 H, J=8.3 Hz), 6.72 (dd, py-C$^4$H, 1 H, J=7.7, 1.8 Hz), 7.07 (s, CH, 1 H), 7.76 (d, py-C$^6$H, 1 H, J=5.1 Hz). $^{13}$C{$^1$H} NMR (C$_6$D$_6$, 100 MHz): δ 112.20 (CH), 114.14 (py-C$^3$H), 117.61 (py-C$^5$H), 137.04 (py-C$^4$H), 147.90 (py-C$^6$H), 158.46 (py-C$^2$).

11. (smif)CrN(SiMe$_3$)$_2$: A solution of smifH (0.153 g, 0.78 mmol) in 10 mL Et$_2$O was added dropwise to a stirring solution of Cr{N(SiMe$_3$)$_2$}$_2$(THF)$_2$ (0.400 g, 0.77 mmol) in Et$_2$O (10 mL) at 23° C. The solution became emerald green. The reaction was degassed and allowed to stir for 12 h at 23° C. while green crystals precipitated from solution. The suspension was concentrated, filtered, and washed with cold Et$_2$O to isolate 0.237 g (smif)CrN(SiMe$_3$)$_2$ as green crystals (74%). $^1$H NMR(C$_6$D$_6$, 400 MHz): δ −78.71 ($υ_{1/2}$≈2000 Hz, py-CH, 1 H), −74.23 ($υ_{1/2}$≈300 Hz, CH, 1 H), −37.81 ($υ_{1/2}$≈520 Hz, py-CH, 1 H), −18.60 ($υ_{1/2}$≈580 Hz, py-CH, 1 H), 23.28 ($υ_{1/2}$≈500 Hz, py-CH, 1 H), 57.60 ($υ_{1/2}$≈5800 Hz, Si(CH$_3$)$_3$, 9 H). Anal. Calcd. H$_{28}$C$_{18}$N$_4$Si$_2$Cr: C, 52.91; H, 6.91; N, 13.71. Found: C, 51.90; H, 6.78; N, 14.02. $μ_{eff}$ (SQUID, 293K)=4.9$μ_B$.

12. (smif)FeN(SiMe$_3$)$_2$ (in solution) and [{(Me$_3$Si)$_2$N}Fe]$_2$(μ-N$_2^{am}$,N$_4^{py}$-2,3,5,6-tetrakis(pyridin-2-yl)piperazyl) (solid state)

A solution of smifH (0.700 g, 3.55 mmol) in 10 mL Et$_2$O was added dropwise to a stirring solution of Fe{N(SiMe$_3$)$_2$}$_2$(THF) (1.592 g, 3.55 mmol) in Et$_2$O (10 mL) at 23° C. The solution immediately became dark green. The reaction was degassed, allowed to stir at 23° C. for 3 h, and volatiles were removed. The orange crystalline solid was triturated with pentane, stripped, and filtered in Et$_2$O to produce 1.090 g of [{(Me$_3$Si)$_2$N}Fe]$_2$(μ-N$_2^{am}$,N$_4^{py}$-2,3,5,6-tetrakis(pyridin-2-yl)piperazyl) (74%). $^1$H NMR (THF-d$_8$, 400 MHz): δ−0.01 ($υ_{1/2}$≈9 Hz, CH, 1 H), 34.57 ($υ_{1/2}$≈380 Hz, Si(CH$_3$)$_3$, 9 H), 46.70 ($υ_{1/2}$≈35 Hz, py-CH, 1 H), 46.99 ($υ_{1/2}$≈110 Hz, py-CH, 1 H), 86.21 ($υ_{1/2}$≈790 Hz, py-CH, 1 H), 165.40 ($υ_{1/2}$≈620 Hz, py-CH, 1 H). $^1$H NMR (C$_6$D$_6$, 400 MHz): δ−14.34 ($υ_{1/2}$≈270 Hz, Si(CH$_3$)$_3$, 9 H), −10.83 ($υ_{1/2}$≈100 Hz, CH, 1 H), 71.49 ($υ_{1/2}$≈130 Hz, py-CH, 1 H), 79.24 ($υ_{1/2}$≈200 Hz, py-CH, 1 H), 136.99 ($υ_{1/2}$≈500 Hz, py-CH, 1 H), 203.24 ($υ_{1/2}$≈430 Hz, py-CH, 1 H). $μ_{eff}$ dimer (SQUID, 300K)=7.34$μ_B$.

13. (Me$_4$smif)FeN(SiMe$_3$)$_2$ (in solution) and [(μ-C,N$^{am}$, N$_2^{py}$-2-(6-methylpyridin-2-yl)-2-(1-(6-methylpyridin-2-yl)ethylamino)ethan-1-ido)Fe{N(SiMe$_3$)$_2$}]$_2$ (solid state, see picture below)

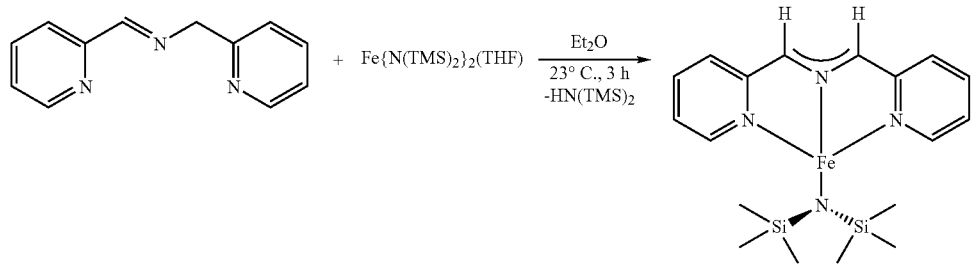

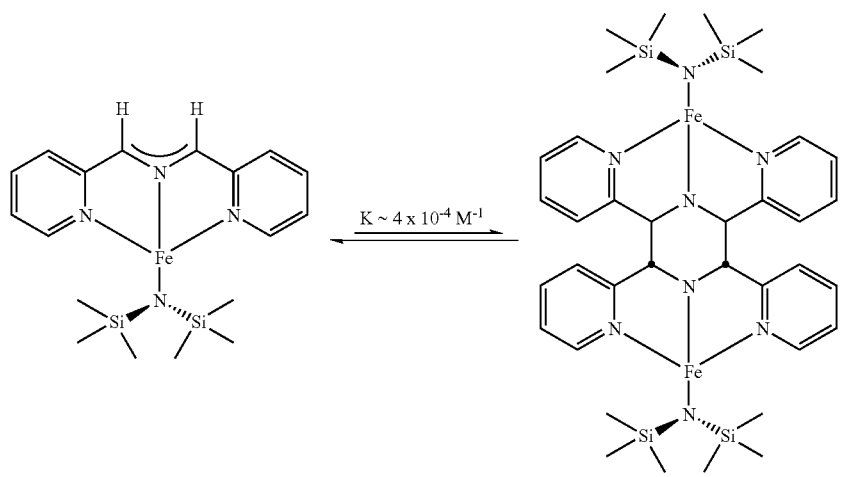

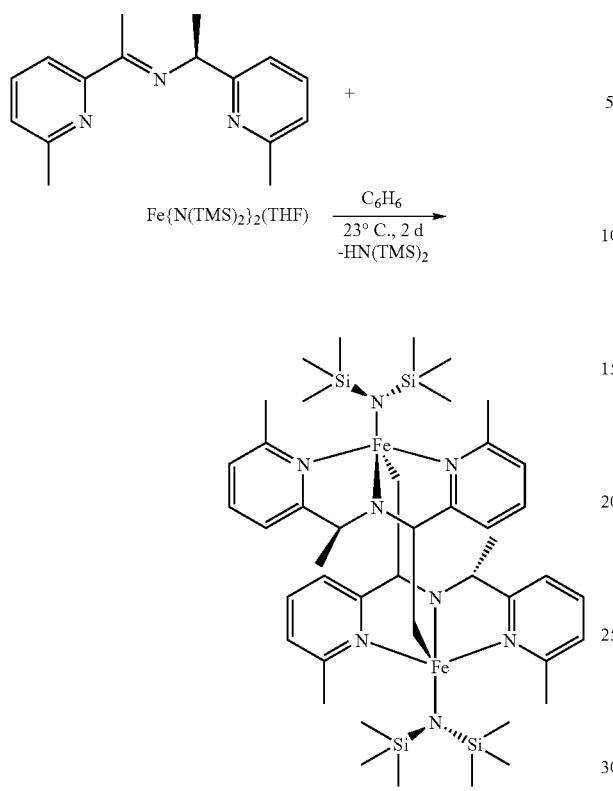

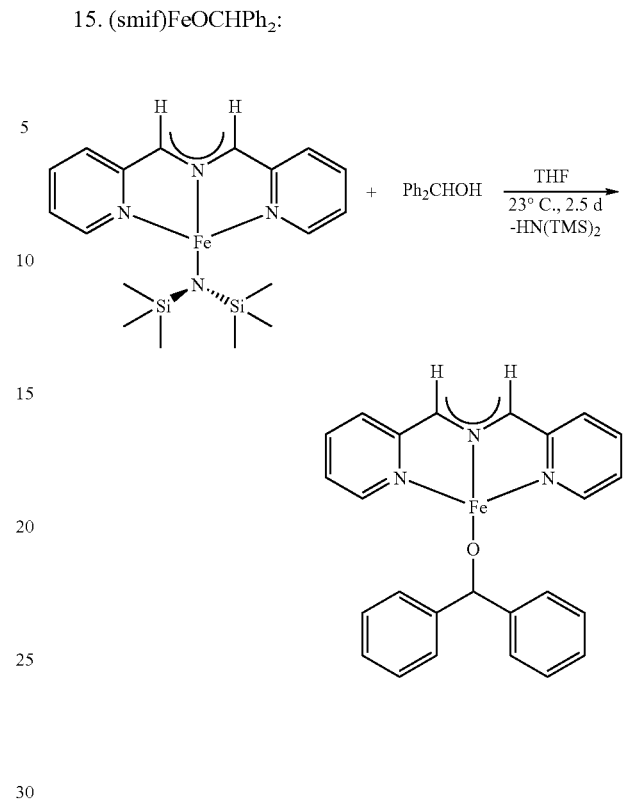

A small tube fitted to a 180° needle valve was charged with Fe{N(SiMe$_3$)$_2$}$_2$(THF) (0.105 g, 0.23 mmol) and Me$_4$smifH (0.025 g, 0.30 mmol). A bell pepper green solution appeared immediately upon addition of benzene. The reaction was degassed, sealed under vacuum, and allowed to sit for 2 d at 23° C. The tube was opened, and benzene was decanted. Red-orange crystals of [μ-N$^{am}$,N$_2^{py}$-2-(6-methylpyridin-2-yl)-2-(1-(6-methylpyridin-2-yl)ethylamino)ethan-1-ido) Fe{N(SiMe$_3$)$_2$}]$_2$ were washed with Et$_2$O. (0.069 g, 63%). $^1$H NMR (C$_6$D$_6$, 400 MHz): δ−50.62 (υ$_{1/2}$≈370 Hz, CH$_3$, 3 H), 18.23 (υ$_{1/2}$≈600 Hz, Si(CH$_3$)$_3$, 9 H), 21.94 (υ$_{1/2}$≈350 Hz, py-CH, 1 H), 48.25 (υ$_{1/2}$≈44 Hz, py-CH, 1 H), 57.31 (υ$_{1/2}$≈310 Hz, py-CH, 1 H), 69.57 (υ$_{1/2}$≈440 Hz, CH$_3$, 3 H). Anal. Calcd. H$_{22}$C$_{36}$N$_4$Si$_2$Fe: C, 56.39; H, 7.74; N, 11.96. Found: C, 56.62; H, 7.84; N, 12.04. μ$_{eff}$ (SQUID, 293K)= 4.3μ$_B$.

14. ($^o$-Me$_2$smif)FeN(SiMe$_3$)$_2$: To a stirring solution of Fe{N(SiMe$_3$)$_2$}$_2$(THF) (0.398 g, 0.89 mmol) in 8 mL Et$_2$O was slowly added a solution of $^o$-Me$_2$smifH (0.200 g, 0.89 mmol) in Et$_2$O (8 mL) at 23° C. The reaction mixture became teal blue. The reaction was degassed, warmed to 23° C., and stirred for 12 h while gold crystals precipitated from solution. The suspension was concentrated, and gold crystals were isolated by filtration to yield 0.152 g ($^o$-Me$_2$smif)FeN (SiMe$_3$)$_2$ (39%). $^1$H NMR (C$_6$D$_6$, 400 MHz): δ−25.33 (υ$_{1/2}$≈812 Hz, CH$_3$, 3 H), −2.12 (υ$_{1/2}$≈53 Hz, CH, 1 H), 22.30 (υ$_{1/2}$≈507 Hz, Si(CH$_3$)$_3$, 9 H), 32.55 (υ$_{1/2}$≈154 Hz, py-CH, 1 H), 37.80 (υ$_{1/2}$≈57 Hz, py-CH, 1 H), 150.52 (υ$_{1/2}$≈974 Hz, py-CH, 1 H). μ$_{eff}$(SQUID, 293K)=5.09μ$_B$.

15. (smif)FeOCHPh$_2$:

To a 25 mL round bottom flask charged with [(smif)FeN (TMS)$_2$]$_2$ (0.200 g, 0.24 mmol) and diphenylmethanol (0.089 g, 0.48 mmol) was vacuum transferred 15 mL THF at −78° C. resulting in an emerald green solution. After stirring at 23° C. for 2.5 d, volatiles were removed in vacuo from the dark kelly green solution. The solid was washed with pentane to remove excess diphenylmethanol before filtering and crystallizing [(smif)FeOCHPh$_2$]$_2$ from Et$_2$O (0.125 g, 59%). $^1$H NMR (C$_6$D$_6$, 400 MHz): δ−29.46 (υ$_{1/2}$≈365 Hz, Ar—CH, 4 H), −0.77 (υ$_{1/2}$≈61 Hz, Ar—CH, 4 H), 1.49 (υ$_{1/2}$≈20 Hz, CH, 1 H), 3.40 (υ$_{1/2}$≈38 Hz, Ar—CH, 2 H), 3.74 (υ$_{1/2}$≈30 Hz, CH, 1 H), 35.55 (υ$_{1/2}$≈47 Hz, py-CH, 1 H), 66.47 (υ$_{1/2}$≈73 Hz, py-CH, 1 H), 125.50 (υ$_{1/2}$≈861 Hz, py-CH, 1 H), 254.92 (υ$_{1/2}$≈554 Hz, py-CH, 1 H).

16. (smif)(dpma)Fe:

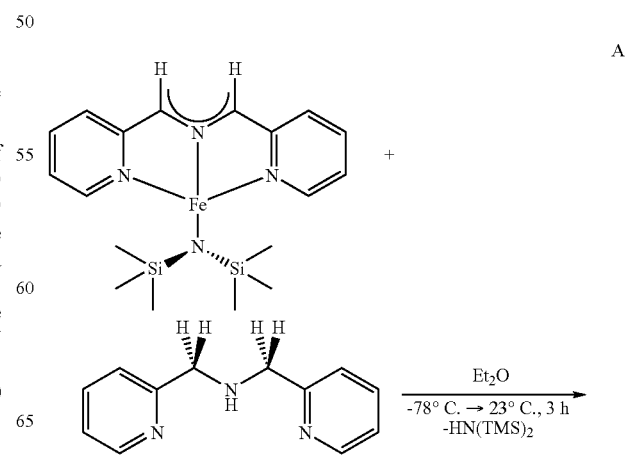

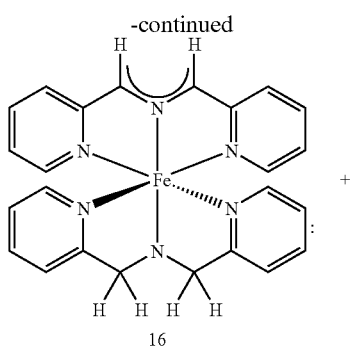

16

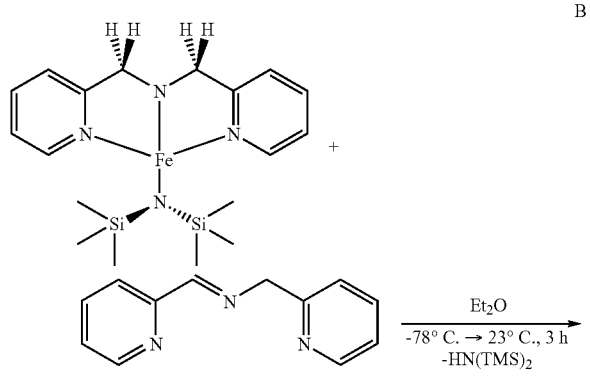

A. To a stirring suspension of [(smif)FeN(TMS)$_2$]$_2$ (0.300 g, 0.36 mmol) in 20 mL Et$_2$O at −78° C. was slowly added a solution of di-(2-picolyl)amine (0.145 g, 0.73 mmol) in Et$_2$O (10 mL) under argon. The suspension immediately changed from emerald green to red. The reaction was degassed and allowed to stir at 23° C. for 3 h while dark red crystals precipitated from solution. The reaction mixture was concentrated, filtered cold, and washed with cold Et$_2$O to yield a mixture of (smif)(dpma)Fe and (smif)$_2$Fe (16:1, 0.225 g, representing 63% of (smif)(dpma)Fe).

B. To a stirring solution of (dpma)FeN(TMS)$_2$ (0.300 g, 0.72 mmol) in 20 mL Et$_2$O at −78° C. was slowly added a solution of smifH (0.143 g, 0.72 mmol) in Et$_2$O (10 mL) under argon. The reaction was degassed. The reaction mixture changed color from cherry red to dark blue to purple to dark red as the solution warmed to 23° C. Dark red crystals precipitated from solution while it stirred at 23° C. for 3 h. The reaction mixture was concentrated, filtered cold, and washed with cold Et$_2$O to yield a mixture of (smif)(dpma)Fe and (smif)$_2$Fe (2:1, 0.260 g, representing 51% (smif)(dpma)Fe). $^1$H NMR (C$_6$D$_6$, 400 MHz): δ 8.70 (υ$_{1/2}$≈19 Hz, CH$_2$, 2 H), 14.98 (υ$_{1/2}$≈40 Hz, py-CH, 1 H), 16.95 (υ$_{1/2}$≈40 Hz, py-CH, 1 H), 19.48 (υ$_{1/2}$≈60 Hz, py-CH, 1 H), 21.80 (υ$_{1/2}$≈80 Hz, py-CH, 1 H), 30.37 (υ$_{1/2}$≈187 Hz, py-CH, 1 H), 32.02 (υ$_{1/2}$≈234 Hz, py-CH, 1 H), 47.34 (υ$_{1/2}$≈388 Hz, CH, 1 H), 81.73 (υ$_{1/2}$≈1900 Hz, py-CH, 1 H), 183.55 (υ$_{1/2}$≈3500 Hz, py-CH, 1 H).

17. $^o$-Me$_2$smifH:

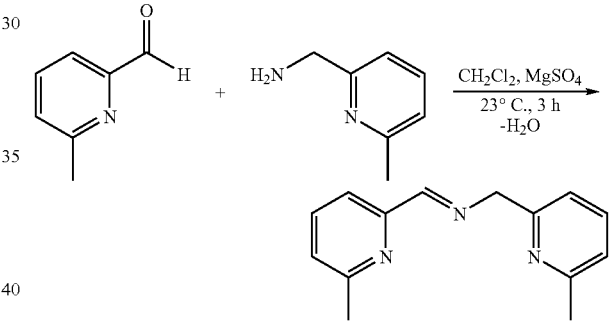

To a suspension of anhydrous MgSO$_4$ (5.036 g, 41.82 mmol) in 16 mL of CH$_2$Cl$_2$ was added 6-methyl-2-pyridinecarboxaldehyde (1.014 g, 8.37 mmol) followed by the slow addition of 6-methyl-2-pyridylmethylamine (1.022 g, 8.37 mmol). The yellow suspension stirred at 23° C. for 3 h. The reaction mixture was filtered and washed with CH$_2$Cl$_2$. The solvent was removed under vacuum to yield a pale yellow solid (1.73 g, 92%). $^1$H NMR (C$_6$D$_6$, 500 MHz): δ 2.38 (s, py-CH$_3$, 3 H), 2.39 (s, py$^{im}$-CH$_3$, 3 H), 4.93 (s, CH$_2$, 2 H), 6.61 (d, py-C$^3$H, py-C$^4$H, 2 H, J=6.5 Hz), 7.06 (t, py$^{im}$-C$^4$H, 1 H, J=7.5 Hz), 7.10 (d, py-C$^5$H, py$^{im}$-C$^5$H, 2 H, J=7 Hz), 8.02 (d, py$^{im}$-C$^3$H, 1 H, J=8 Hz), 8.62 (s, CH, 1 H). $^{13}$C{$^1$H} NMR (C$_6$D$_6$, 125 MHz): δ 24.62 (py-CH$_3$), 24.84 (py$^{im}$-CH$_3$), 67.45 (CH$_2$), 118.47 (py-C$^3$H), 119.56 (py$^{im}$-C$^3$H), 121.60 (py-C$^5$H), 124.36 (py$^{im}$-C$^5$H), 136.70 (py-C$^4$H), 136.78 (py$^{im}$-C$^4$H), 155.38 (py$^{im}$-C$^2$), 158.46 (py-C$^6$), 158.50 (py$^{im}$-C$^6$), 159.46 (py-C$^2$), 164.79 (im-CH).

18. $^b$Me$_2$smifH:

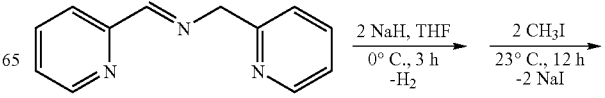

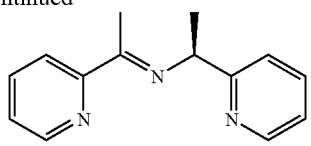

A solution of smifH (1.000 g, 5.07 mmol) in 20 mL THF was slowly added to a suspension of NaH (0.243 g, 10.13 mmol) in 15 mL THF at 0° C. The reaction mixture turned magenta and was stirred at 0° C. for 3 h prior to the addition of $CH_3I$ (0.63 mL, 10.11 mmol). After stirring at 23° C. for 12 h, the solution appeared orange-red. The volatiles were removed in vacuo, and the residue was filtered in $CH_2Cl_2$. Methylene chloride was removed, and the solid was triturated with $Et_2O$ and filtered to yield an orange solid (1.138 g, 99%). $^1H$ NMR ($C_6D_6$, 500 MHz): δ 1.67 (d, $CH_3$, 3 H, J=7 Hz), 2.37 (s, im-$CH_3$, 3 H), 5.19 (q, CH, 1 H, J=6.5 Hz), 6.67 (t, py-$C^5H$, 1 H, J=5.5 Hz), 6.68 (t, $py^{im}$-$C^5H$, 1 H, J=5.5 Hz), 7.17 (t, py-$C^4H$, 1 H, J=7.5 Hz), 7.19 (t, $py^{im}$-$C^4H$, 1 H, J=7.5 Hz), 7.63 (d, py-$C^3H$, 1 H, J=8 Hz), 8.39 (d, $py^{im}$-$C^3H$, 1 H, J=8 Hz), 8.44 (d, py-$C^6H$, 1 H, J=3.5 Hz), 8.54 (d, $py^{im}$-$C^6H$, 1 H, J=4 Hz). $^{13}C\{^1H\}$ NMR ($C_6D_6$, 125 MHz): δ 13.97 ($CH_3$), 23.52 (im-$CH_3$), 62.94 (im-CH), 121.37 (py-$C^3H$), 121.49 ($py^{im}$-$C^3H$), 122.05 (py-$C^5H$), 124.38 ($py^{im}$-$C^5H$), 136.08 (py-$C^4H$), 136.50 ($py^{im}$-$C^4H$), 148.81 (py-$C^6H$), 149.66 ($py^{im}$-$C^6H$), 158.60 (im-CH), 165.95 ($py^{im}$-$C^2$), 166.23 (py-$C^2$). [NOTE: The person of skill in the art will recognize that the methyl iodide reactions described herein could be replaced by any optionally substituted alkyl halide or sulfate to provide analogous compounds.]

19. $Me_4smifH$:

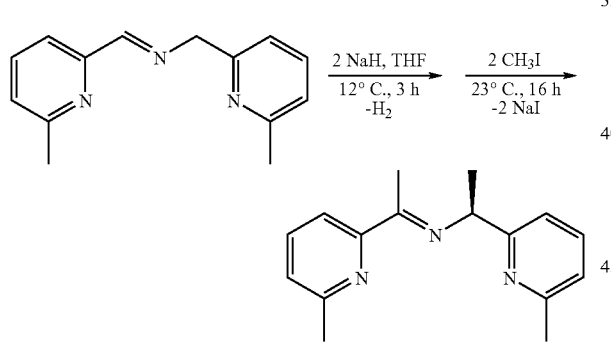

A solution of smifH (2.500 g, 11.10 mmol) in 20 mL THF was slowly added to a suspension of NaH (0.533 g, 22.21 mmol) in 15 mL THF at 12° C. The reaction mixture turned magenta and was stirred at 12° C. for 3 h prior to the addition of $CH_3I$ (1.40 mL, 22.49 mmol). After stirring at 23° C. for 16 h, the volatiles from the orange solution were removed in vacuo. The residue was triturated, filtered, and washed with $CH_2Cl_2$. Methylene chloride was removed, and the solid was triturated with $Et_2O$ and filtered to yield a pale orange solid (1.138 g, 99%). $^1H$ NMR ($C_6D_6$, 500 MHz): δ 1.71 (d, $CH_3$, 3 H, J=6.5 Hz), 2.39 (s, py-$CH_3$, 3 H), 2.40 (s, $py^{im}$-$CH_3$, 3 H), 2.47 (s, im-$CH_3$, 3 H), 5.20 (q, CH, 1 H, J=6.5 Hz), 6.66 (t, py-$C^5H$, $py^{im}$-$C^5H$, 2 H, J=7.5 Hz), 7.18 (t, py-$C^4H$, 1 H, J=7.5 Hz), 7.20 (t, $py^{im}$-$C^4H$, 1 H, J=7.5 Hz), 7.54 (d, py-$C^3H$, 1 H, J=7.5 Hz), 8.31 (d, $py^{im}$-$C^3H$, 1 H, J=8 Hz). $^{13}C\{^1H\}$ NMR ($C_6D_6$, 125 MHz): δ 14.02 ($CH_3$), 23.74 (im-$CH_3$), 24.80 (py-$CH_3$), 24.98 ($py^{im}$-$CH_3$), 63.12 (im-CH), 118.34 (py-$C^3H$), 118.66 ($py^{im}$-$C^3H$), 121.41 (py-$C^5H$), 123.72 ($py^{im}$-$C^5H$), 136.48 (py-$C^4H$), 136.93 ($py^{im}$-$C^4H$), 157.26 (im-CH), 158.02 (py-$C^6$), 158.23 ($py^{im}$-$C^6$), 165.44 ($py^{im}$-$C^2$), 166.24 (py-$C^2$).

20. Li(smif): To a solution of lithium bis(trimethylsilyl) amide (1.273 g, 7.60 mmol) in 50 mL THF was slowly added a solution of smifH (1.500 g, 7.60 mmol) in 50 mL THF at −78° C. under argon. The solution immediately turned magenta and was stirred at −78° C. for 2 h. After stirring at 23° C. for 2 h, the volatiles were removed in vacuo. The solid was triturated with $Et_2O$ and filtered. Li(smif) was isolated as a metallic gold solid (1.389 g, 90%). $^1H$ NMR ($C_6D_6$, 400 MHz): δ 5.98 (t, py-$C^5H$, 1 H, J=8 Hz), 6.50 (d, py-$C^3H$, 1 H, J=8 Hz), 6.84 (t, py-$C^4H$, 1 H, J=8 Hz), 7.16 (s, CH, 1 H), 7.66 (d, py-$C^6H$, 1 H, J=4 Hz). $^{13}C\{^1H\}$ NMR ($C_6D_6$, 100 MHz): δ 113.20 (CH), 117.95 (py-$C^3H$), 118.65 (py-$C^5H$), 136.18 (py-$C^4H$), 148.90 (py-$C^6H$), 159.44 (py-$C^2$).

21. Na(smif): To a solution of sodium bis(trimethylsilyl) amide (1.395 g, 7.60 mmol) in 50 mL THF was slowly added a solution of smifH (1.500 g, 7.60 mmol) in 50 mL THF at −78° C. under argon. The solution immediately turned magenta and was stirred at −78° C. for 2 h. After stirring at 23° C. for 2 h, the volatiles were removed in vacuo. The solid was triturated with $Et_2O$ (3×15 mL) prior to filtering. Na(smif) was isolated as a metallic gold solid (1.602 g, 96%). $^1H$ NMR ($C_6D_6$, 400 MHz): δ 6.19 (t, py-$C^5H$, 1 H, J=5.6 Hz), 6.55 (d, py-$C^3H$, 1 H, J=8 Hz), 6.97 (t, py-$C^4H$, 1 H, J=7.2 Hz), 7.04 (s, CH, 1 H), 7.72 (d, py-$C^6H$, 1 H, J=4 Hz). $^{13}C\{^1H\}$ NMR ($C_6D_6$, 100 MHz): δ 112.19 (CH), 115.70 (py-$C^3H$), 119.05 (py-$C^5H$), 135.62 (py-$C^4H$), 149.81 (py-$C^6H$), 160.23 (py-C2).

22. $Na^tBuNCOsmif$:

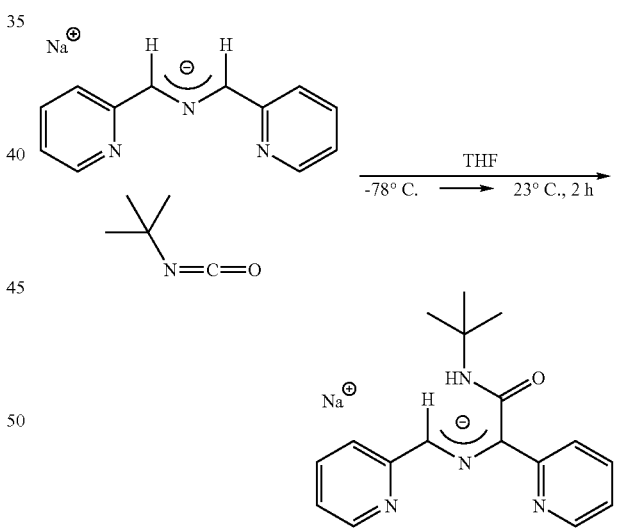

To a solution of Nasmif (0.300 g, 1.37 mmol) in 20 mL THF was added tert-butylisocyanate (156 μL, 1.37 mmol) via syringe at −78° C. under argon. The solution was warmed to 23° C. and turned red. Volatiles were removed in vacuo after 2 h, and the resulting film was triturated with $Et_2O$ to remove residual THF. $Na^tBuNCOsmif$ was isolated as a metallic green solid (0.396 g, 91%). $^1H$ NMR ($C_6D_6$, 500 MHz): δ 1.39 (s, $C(CH_3)_3$, 9 H), 6.33 (t, py-$C^5H$, 1 H, J=5.8 Hz), 6.43

(t, py'-C⁵H, 1 H, J=5.8 Hz), 6.55 (d, py-C³H, 1 H, J=8.1 Hz), 6.94 (t, py-C⁴H, 1 H, J=7.0 Hz), 7.17 (t, py'-C⁴H, 1 H, J=7.7 Hz), 7.81 (d, py'-C³H, 1 H, J=8.1 Hz), 8.18 (s, NH, 1 H), 8.20 (d, py-C⁶H, 1 H, J=5.4 Hz), 8.44 (d, py'-C⁶H, 1 H, J=3.9 Hz), 10.58 (s, CH, 1 H). $^{13}C\{^1H\}$ NMR (C₆D₆, 125 MHz): δ 30.58 (C(CH₃)₃), 50.26 (C(CH₃)₃), 111.02 (py'-C³H), 116.24 (py'-C⁵H), 116.94 (py-C³H), 118.74 (py-C⁵H), 121.24 (C(C=O)), 123.58 (CH), 135.18 (py-C⁴H), 136.52 (py'-C⁴H), 148.28 (py-C⁶H), 150.40 (py'-C⁶H), 157.79 (C=O), 160.47 (py'-C²), 169.93 (py-C²).

23. (ᵗBuNCOsmif)₂Fe:

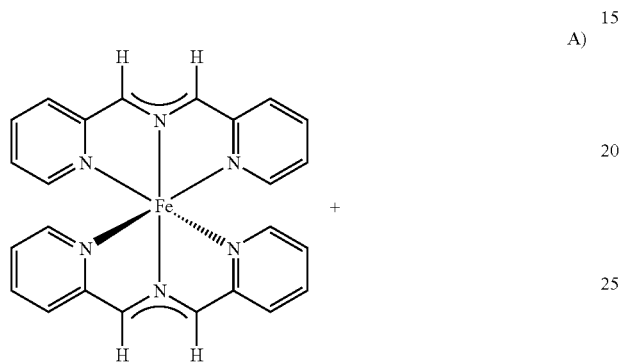

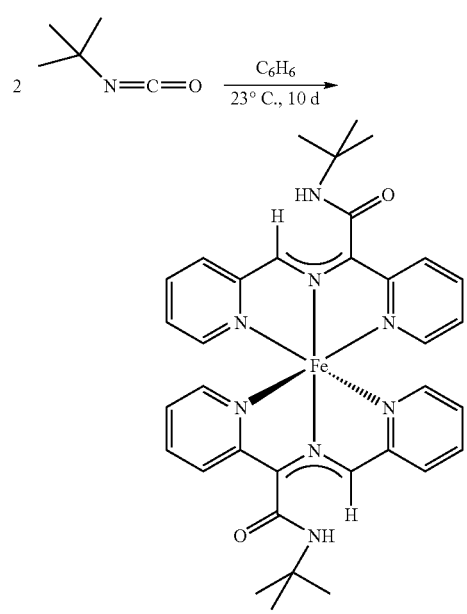

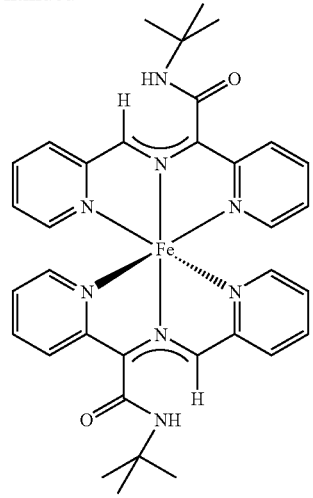

A) To a small glass bomb reactor charged with (smif)₂Fe (0.150 g, 0.33 mmol) was added 10 mL C₆H₆. The bomb was cooled to −78° C. and tert-butylisocyanate (76 μL, 0.66 mmol) was added via GC syringe under argon purge. The solution turned deep red-orange after stirring at 23° C. for 18 h. The reaction was stirred at 23° C. for 10 d. Volatiles were removed in vacuo, and the reaction mixture was triturated with pentane (3×5 mL). After filtering and washing with pentane, (ᵗBuNCOsmif)₂Fe was isolated as a dark red solid (0.102 g, 47%). B) To a 25 mL flask charged with FeBr₂(THF)₂ (0.141 g, 0.39 mmol) and NaᵗBuNCOsmif (0.250 g, 0.79 mmol) was vacuum transferred 20 mL THF at −78° C. The solution turned red-orange upon warming to 23° C. and was stirred for 18 h. Volatiles were removed in vacuo, and the resulting solid was triturated with Et₂O prior to filtering in toluene. A dark red microcrystalline solid, (ᵗBuNCOsmif)₂Fe, was obtained (0.154 g, 61%). ¹H NMR (C₆D₆, 500 MHz) δ: 1.53 (s, C(CH₃)₃, 9 H), 5.37 (s, NH, 1 H), 5.71 (t, py-C⁵H, 1 H, J=6.2 Hz), 5.76 (t, py'-C⁵H, 1 H, J=6.3 Hz), 6.32 (t, py-C⁴H, 1 H, J=7.3 Hz), 6.36 (d, py-C³H, 1 H, J=7.9 Hz), 6.48 (t, py'-C⁴H, 1 H, J=6.3 Hz), 7.03 (d, py'-C³H, 1 H, J=8.5 Hz), 7.75 (d, py-C⁶H, 1 H, J=5.3 Hz), 7.98 (d, py'-C⁶H, 1 H, J=5.1 Hz), 9.91 (s, CH, 1 H). $^{13}C\{^1H\}$ NMR (C₆D₆, 125 MHz) δ: 30.08 (C(CH₃)₃), 51.35 (C(CH₃)₃), 113.33 (py'-C³H), 116.31 (py'-C⁵H), 116.79 (py-C³H), 119.27 (py-C⁵H), 119.95 (C(C=O)), 130.04 (CH), 135.01 (py-C⁴H), 135.42 (py'-C⁴H), 151.70 (py-C⁶H), 152.06 (py'-C⁶H), 164.40 (py'-C²), 164.47 (C=O), 165.62 (py-C²). Anal. Calcd. H₃₈C₃₄N₈O₂Cr: C, 63.16; H, 5.92; N, 17.33. Found: C, 63.16; H, 5.92; N, 17.33.

24. (2,6-ⁱPrPhNCOsmif)₂Fe:

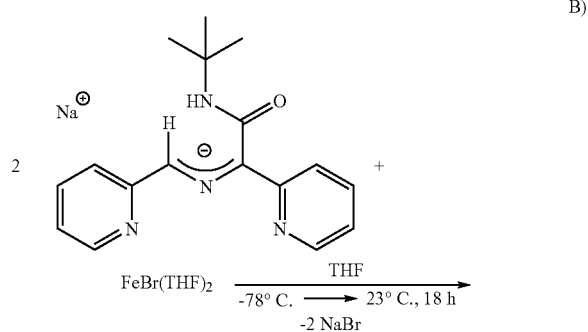

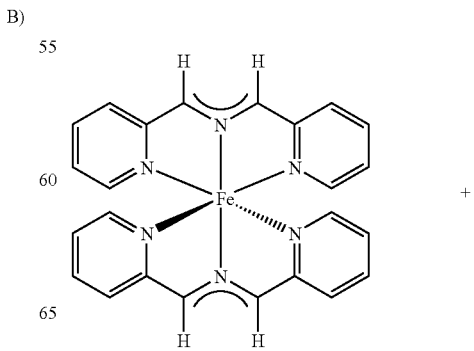

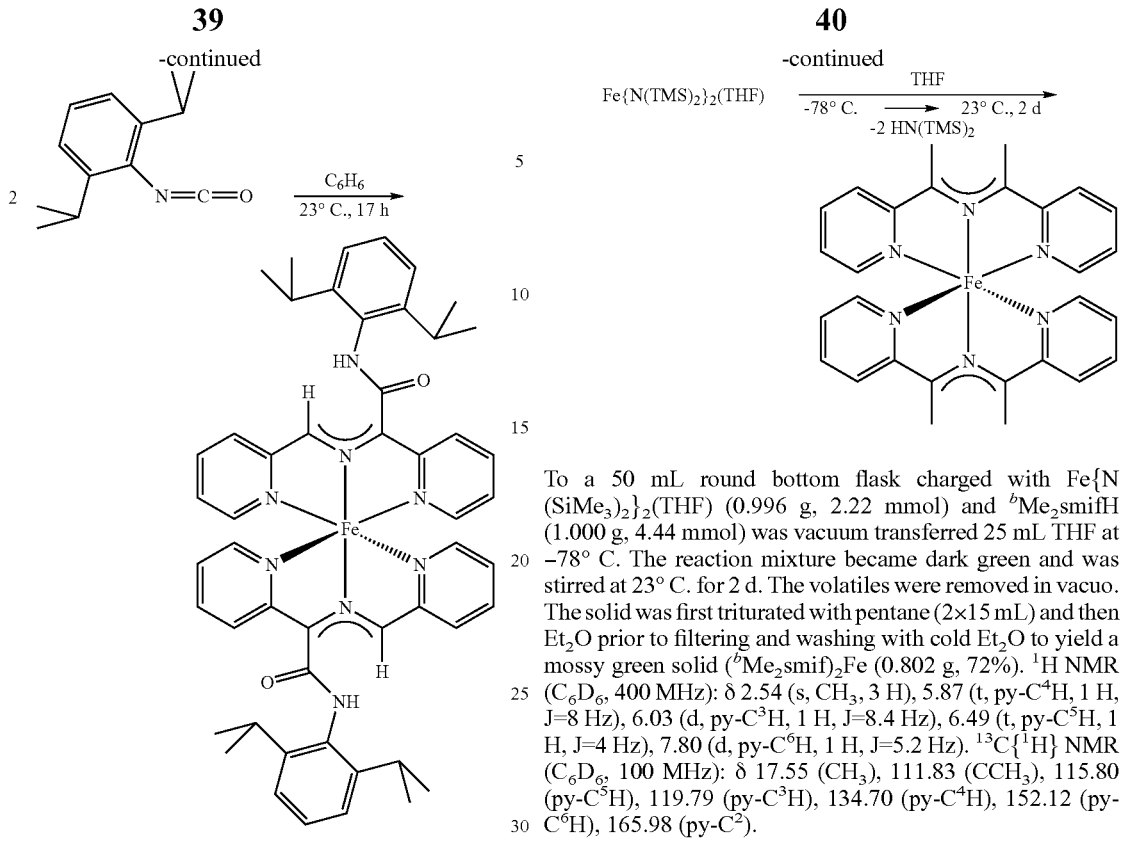

To a 25 mL round bottom flask charged with (smif)₂Fe (0.500 g, 1.12 mmol) was added 20 mL C₆H₆. The flask was cooled to −78° C. and 2,6-diisopropylphenylisocyanate (0.48 mL, 2.24 mmol) were added via syringe under argon purge. Upon warming to 23° C., the solution turned deep red-orange. The reaction stirred at 23° C. for 17 h. Volatiles were removed in vacuo, and the reaction mixture was triturated with pentane (3×5 mL). After filtering and washing with pentane, (2,6-$^i$PrPhNCOsmif)₂Fe was isolated as a dark red solid (0.719 g, 75%). $^1$H NMR (C₆D₆, 400 MHz) δ: 1.38 (s, CH(CH₃)₂, 12 H), 3.56 (sept, CH(CH₃)₂, 2 H, J=6.9 Hz), 5.84 (t, py-C⁵H, py'-C⁵H, 2 H, J=5.3 Hz), 6.33 (d, Ar—C³H, 2 H, J=3.8 Hz), 6.54 (t, Ar—C⁴H, 1 H, J=7.3 Hz), 6.98 (s, NH, 1 H), 7.31 (m, py-C³H, py-C⁴H, py'-C⁴H, 3 H), 7.44 (d, py'-C³H, 1 H, J=8.4 Hz), 7.77 (d, py-C⁶H, 1 H, J=5.4 Hz), 7.99 (d, py'-C⁶H, 1 H, J=5.2 Hz), 10.15 (s, CH, 1 H). $^{13}$C{$^1$H} NMR (C₆D₆, 100 MHz) δ: 24.36 (CH(CH₃)₂), 24.38 (CH(CH₃)₂), 30.07 (CH(CH₃)₂), 114.11 (py'-C³H), 117.00 (py'-C⁵H), 117.98 (py-C³H), 118.34 (py-C⁵H), 119.89 (C(C=O)), 124.07 (CH), 127.92 (Ar—C³H), 133.02 (Ar—C⁴H), 134.18 (py-C⁴H), 135.24 (py'-C⁴H), 136.08 (Ar—C¹), 145.41 (Ar—C²), 151.42 (py-C⁶H), 151.88 (py'-C⁶H), 163.97 (py'-C²), 164.55 (C=O), 165.51 (py-C²). Anal. Calcd. H₅₄C₅₀N₈O₂Fe: C, 70.25; H, 6.37; N, 13.11. Found: C, 70.25; H, 6.37; N, 13.11.

25. ($^b$Me₂smif)₂Fe:

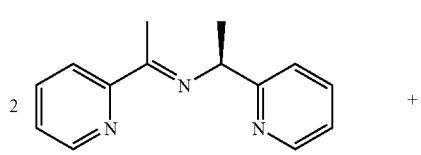

To a 50 mL round bottom flask charged with Fe{N(SiMe₃)₂}₂(THF) (0.996 g, 2.22 mmol) and $^b$Me₂smifH (1.000 g, 4.44 mmol) was vacuum transferred 25 mL THF at −78° C. The reaction mixture became dark green and was stirred at 23° C. for 2 d. The volatiles were removed in vacuo. The solid was first triturated with pentane (2×15 mL) and then Et₂O prior to filtering and washing with cold Et₂O to yield a mossy green solid ($^b$Me₂smif)₂Fe (0.802 g, 72%). $^1$H NMR (C₆D₆, 400 MHz): δ 2.54 (s, CH₃, 3 H), 5.87 (t, py-C⁴H, 1 H, J=8 Hz), 6.03 (d, py-C³H, 1 H, J=8.4 Hz), 6.49 (t, py-C⁵H, 1 H, J=4 Hz), 7.80 (d, py-C⁶H, 1 H, J=5.2 Hz). $^{13}$C{$^1$H} NMR (C₆D₆, 100 MHz): δ 17.55 (CH₃), 111.83 (CCH₃), 115.80 (py-C⁵H), 119.79 (py-C³H), 134.70 (py-C⁴H), 152.12 (py-C⁶H), 165.98 (py-C²).

26. ($^o$Me₂smif)₂Fe:

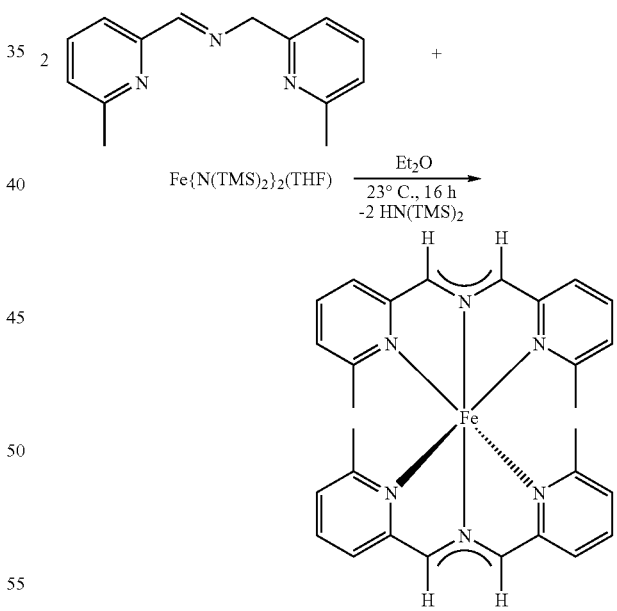

To a solution of Fe{N(SiMe₃)₂}₂(THF) (0.747 g, 1.66 mmol) in 12 mL Et₂O was slowly added a solution of $^o$Me₂smifH (0.750 g, 3.33 mmol) in Et₂O (10 mL) at 23° C. The solution immediately changed from pale green to deep forest green. The reaction was degassed and warmed to 23° C. Gold-bronze crystals began to precipitate from the deep cobalt blue solution after stirring for 30 minutes. The reaction mixture was stirred for an addition 15.5 h. The volatiles were removed, and the solid was triturated and filtered in Et₂O to yield gold-bronze crystals of ($^o$Me₂smif)₂Fe (0.712 g, 85%).

$^1$H NMR (C$_6$D$_6$, 400 MHz): δ −9.64 (υ$_{1/2}$≈110 Hz, CH, 1 H), 7.44 (υ$_{1/2}$≈17 Hz, CH$_3$, 3 H), 36.73 (υ$_{1/2}$≈20 Hz, py-CH, 1 H), 52.87 (υ$_{1/2}$≈15 Hz, py-CH, 1 H), 167.44 (υ$_{1/2}$≈53 Hz, py-CH, 1 H). Anal. Calcd. H$_{28}$C$_{28}$N$_6$Fe: C, 66.67; H, 5.60; N, 16.66. Found: C, 66.54; H, 5.47; N, 16.19. μ$_{eff}$ (SQUID, 293 K)=5.47μ$_B$.

27. (°Mesmif)$_2$Fe:

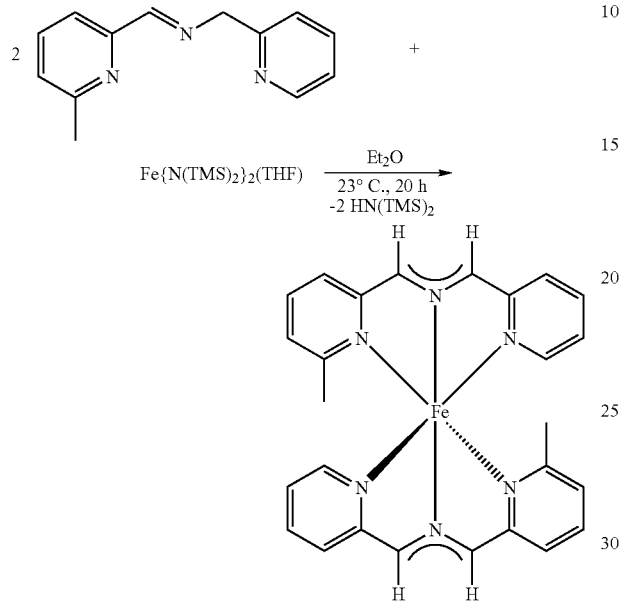

To a solution of Fe{N(SiMe$_3$)$_2$}$_2$(THF) (0.500 g, 1.11 mmol) in 15 mL Et$_2$O was slowly added a solution of °MesmifH (0.471 g, 2.22 mmol) in Et$_2$O (10 mL) at 23° C. The solution immediately changed from pale green to a brilliant blue. The reaction was degassed and warmed to 23° C. Purple-mauve crystals began to precipitate from the deep blue solution while stirring for 20 h. The volatiles were removed, and the solid was triturated and filtered in Et$_2$O to yield purple-mauve crystals of (°Mesmif)$_2$Fe (0.311 g, 59%). $^1$H NMR (C$_6$D$_6$, 400 MHz): δ 2.04 (s, py$^{Me}$-CH$_3$, 3 H), 6.44 (t, py$^{Me}$-C$^4$H, 1 H, J=6.8 Hz), 6.51 (t, py-C$^5$H, 1 H, J=6.8 Hz), 6.83 (d, py$^{Me}$-C$^5$H, 1 H, J=6.8 Hz), 6.97 (br s, py$^{Me}$-C$^3$H, py-C$^4$H, 2 H), 7.59 (d, py-C$^6$H, 1 H, J=6 Hz), 11.43 (υ$_{1/2}$≈29 Hz, CH, 1 H), 12.04 (υ$_{1/2}$≈46 Hz, CH, 1 H), 13.31 (υ$_{1/2}$≈52 Hz, py-C$^3$H, 1 H). $^{13}$C{$^1$H} NMR (C$_6$D$_6$, 100 MHz): δ 25.93 (py$^{Me}$-CH$_3$), 100.75 (py$^{Me}$-C$^3$H), 103.26 (py$^{Me}$-C$^5$H), 107.54 (py-C$^3$H), 112.22 (py-C$^5$H), 114.11 (py$^{Me}$-C$^4$H), 119.50 (CH), 123.66 (py-C$^4$H), 132.93 (CH), 136.73 (py-C$^6$H), 149.10 (py$^{Me}$-C$^6$H), 160.93 (py$^{Me}$-C$^2$), 170.83 (py-C$^2$). Anal. Calcd. H$_{24}$C$_{26}$N$_6$Fe: C, 65.56; H, 5.08; N, 17.64. Found: C, 65.58; H, 5.25; N, 17.17. μ$_{eff}$ (SQUID, 5K)=0.5μ$_B$ to μ$_{eff}$ (SQUID, 293K)=1.22μ$_B$.

28. (°Mesmif)FeN(TMS)$_2$ (in solution) and [{(Me$_3$Si)$_2$N}Fe]$_2$(μ-N$_2^{am}$,N$_4^{PY}$-2,5-bis(6-methylpyridin-2-yl)-3,6-bis(pyridin-2-yl)piperazyl) (solid state)

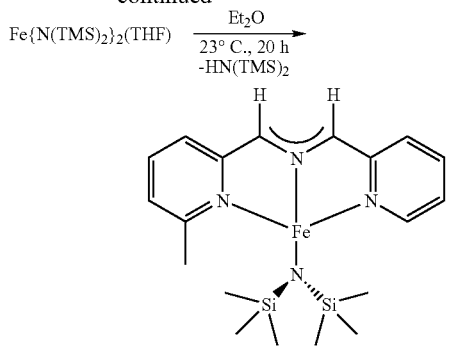

To a stirring solution of Fe{N(SiMe$_3$)$_2$}$_2$(THF) (0.500 g, 1.11 mmol) in 10 mL Et$_2$O was slowly added a solution of °$^−$MesmifH (0.235 g, 1.11 mmol) in Et$_2$O (8 mL) at 23° C. The reaction mixture became emerald-teal green. The reaction was degassed, warmed to 23° C., and stirred for 20 h while yellow-orange crystals precipitated from solution. The suspension was concentrated, and yellow-orange crystals were isolated by filtration to yield [{(Me$_3$Si)$_2$N}Fe]$_2$(μ-N$_2^{am}$, N$_4^{PY}$-2,5-bis(6-methylpyridin-2-yl)-3,6-bis(pyridin-2-yl) piperazyl) (0.225, 47%). $^1$H NMR (C$_6$D$_6$, 400 MHz): δ −21.82 (υ$_{1/2}$≈38 Hz, CH, 1 H), −26.10 (υ$_{1/2}$≈38 Hz, CH, 1 H), −13.23 (υ$_{1/2}$≈413 Hz, CH$_3$, 3 H), 0.75 (υ$_{1/2}$≈300 Hz, Si(CH$_3$)$_3$, 18 H), 14.26 (υ$_{1/2}$≈131 Hz, py-CH, 1 H), 40.95 (υ$_{1/2}$≈23 Hz, py-CH, 1 H), 46.13 (υ$_{1/2}$≈374 Hz, py-CH, 1 H), 47.74 (υ$_{1/2}$≈23 Hz, py-CH, 1 H), 59.84 (υ$_{1/2}$≈96 Hz, py-CH, 1 H), 64.39 (υ$_{1/2}$≈96 Hz, py-CH, 1 H), 252.29 (υ$_{1/2}$≈1000 Hz, py-CH, 1 H).

29. °MesmifH:

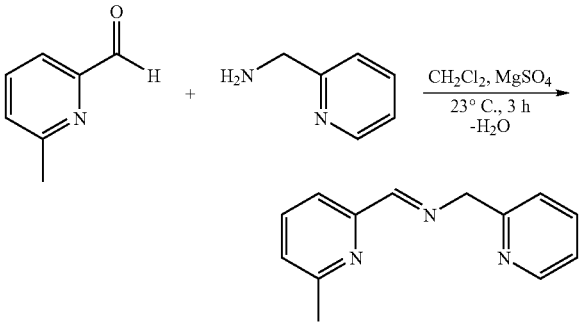

To a suspension of anhydrous MgSO$_4$ (12.421 g, 103.19 mmol) in 40 mL of CH$_2$Cl$_2$ was added 6-methyl-2-pyridinecarboxaldehyde (2.500 g, 20.64 mmol) followed by the slow addition of 2-(aminomethyl)pyridine (2.232 g, 20.64 mmol). The suspension stirred at 23° C. for 3 h. The reaction mixture was filtered and washed with CH$_2$Cl$_2$. The solvent was removed under vacuum to yield a pale yellow liquid (4.25 g, 97%). $^1$H NMR (C$_6$D$_6$, 400 MHz): δ 2.39 (s, CH$_3$, 3 H), 4.92 (s, CH$_2$, 2 H), 6.60 (d, py$^{Me}$-C$^5$H, 1 H, J=7.6 Hz), 6.61 (t, py-C$^5$H, 1 H, J=5.3 Hz), 7.04 (t, py$^{Me}$-C$^4$H, 1 H, J=7.6 Hz), 7.08 (td, py-C$^4$H, 1 H, J=7.5, 1.6 Hz), 7.20 (d, py-C$^3$H, 1 H, J=7.8 Hz), 8.02 (d, py$^{Me}$-C$^3$H, 1 H, J=7.8 Hz), 8.48 (d, py-C$^6$H, 1 H, J=4.8 Hz), 8.61 (s, im-CH, 1 H). $^{13}$C{$^1$H} NMR (C$_6$D$_6$, 100 MHz): δ 24.62 (CH$_3$), 67.24 (CH$_2$), 118.48 (py$^{im}$-C$^3$H), 122.16 (py-C$^3$H), 122.53 (py-C$^5$H), 124.39 (py-C$^5$H), 136.36 (py-C$^4$H), 137.70 (py$^{im}$-C$^4$H), 149.95 (py-C$^6$H), 154.25 (py$^{im}$-C$^6$), 158.54 (py$^{im}$-C$^2$), 160.22 (py-C$^2$), 164.97 (im-CH).

30. d$_2$-smifH: To a suspension of anhydrous MgSO$_4$ (1.341 g, 11.95 mmol) in 4 mL of CH$_2$Cl$_2$ was added 2-pyridinecarboxaldehyde (0.238 g, 2.22 mmol) followed by the slow addition of 2-(amino-d$_2$-methyl-d$_2$)pyridine (0.250 g, 2.22 mmol). The suspension stirred at 23° C. for 3 h. The reaction mixture was filtered and washed with CH$_2$Cl$_2$. The solvent was removed under vacuum to yield a pale yellow liquid (0.426 g, 96%). $^1$H NMR (C$_6$D$_6$, 500 MHz): δ 6.62 (dt, py-C$^5$H, py$^{im}$-C$^5$H, 2 H, J=4.8, 1.3 Hz), 7.03 (td, py-C$^4$H, 1 H, J=7.7 Hz), 7.09 (td, py$^{im}$-C$^4$H, 1 H, J=7 Hz), 7.17 (dt, py-C$^3$H, 1 H, J=10 Hz), 8.11 (dt, py$^{im}$-C$^3$H, 1 H, J=7.5 Hz), 8.47 (d, py-C$^6$H, 1 H, J=5 Hz), 8.48 (d, py$^{im}$-C$^6$H, 1 H, J=5 Hz), 8.60 (s, CH, 1 H). $^{13}$C{$^1$H} NMR (C$_6$D$_6$, 125 MHz): δ 121.30 (py-C$^3$H), 122.20 (py$^{im}$-C$^3$H), 122.55 (py-C$^5$H), 124.88 (py$^{im}$-C$^5$H), 136.30 (py-C$^4$H), 136.34 (py$^{im}$-C$^4$H), 149.93 (py-C$^6$H), 149.99 (py$^{im}$-C$^6$H), 155.95 (py$^{im}$-C$^2$), 160.05 (py-C$^2$), 164.75 (im-CH).

31. Titanium smif compounds: To a 50 mL 3-neck flask charged with lithium bis(trimethylsilyl)amide (0.340 g, 2.04 mmol) and 0.95% Na/Hg (2.516 g, 1.06 mmol) was vacuum transferred 15 mL THF at −78° C. A solution of smifH (0.400 g, 2.02 mmol) in THF (20 mL) was slowly added to the 3-neck flask via a dropping funnel under argon. The solution immediately turned magenta and stirred at −78° C. for 2 h prior to the addition of TiCl$_3$(THF)$_3$ (0.376 g, 2.25 mmol). The reaction mixture turned dark purple after slowly warming to 23° C. and was stirred for 16 h. The volatiles were removed in vacuo, and the resulting dark black-purple solid was filtered in toluene yielding a mixture of 4 titanium compounds (0.290 g).

(smif)(dpma)Ti:

(smif)$_2$Ti

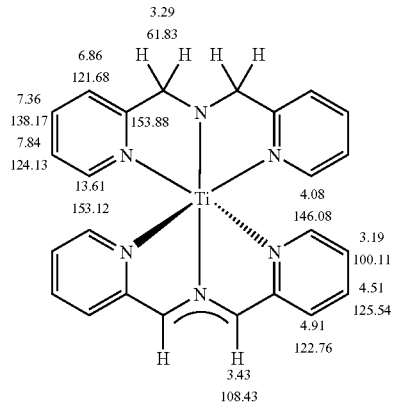

(κ-N$^{am}$,N$^{py}$$_2$-2,3,5,6-tetrakis(pyridin-2-yl)piperazin-1-yl)(smif)Ti

Lithium[(κ-C,N$^{am}$,N$^{im}$,N$^{py}$$_3$-1,2-bis(pyridin-2-yl)-2-(pyridin-2-ylmethyleneamino)ethyl)(pyridin-2-ylmethideyl)amido)Ti(smif)]

32. (smif)$_2$Ru: To a small bomb reactor charged with Nasmif (0.400 g, 1.82 mmol) and (COD)RuCl$_2$ (0.256 g, 0.946 mmol) was vacuum transferred 15 mL THF at −78° C. After warming to 23° C., the bomb was heated in a 60° C. oil bath for 2 d as the magenta solution became dark green with dark purple solids. The reaction mixture was filtered cold in THF, and all volatiles were removed in vacuo. The resulting dark purple, metallic solid was washed with pentane, and 0.276 g (smif)$_2$Ru were isolated (61%). $^1$HNMR (C$_6$D$_6$, 400 MHz): δ 5.64 (t, py-C$^5$H, 1 H, J=6.4 Hz), 6.07 (d, py-C$^3$H, 1 H, J=8.3 Hz), 6.81 (s, CH, 1 H), 6.31 (t, py-C$^4$H, 1 H, J=7.6 Hz), 7.80 (d, py-C$^6$H, 1 H, J=5.1 Hz). $^{13}$C{$^1$H} NMR (C$_6$D$_6$, 125 MHz): δ 113.66 (CH), 113.73 (py-C$^3$H), 115.03 (py-C$^5$H), 134.77 (py-C$^4$H), 151.24 (py-C$^6$H), 167.54 (py-C$^2$).

33. [(smif)$_2$Rh][OTf]: To a small bomb reactor charged with Nasmif (0.072 g, 0.328 mmol), AgOTf (0.042 g, 0.163 mmol) and Rh$_2$(TFA)$_4$ (0.054 g, 0.082 mmol) was vacuum transferred 5 mL toluene at −78° C. After warming to 23° C., the solution turned from magenta to purple and was placed in a 100° C. oil bath for 1 d. The bright blue reaction mixture was filtered and washed with toluene. All volatiles were removed in vacuo leaving a bright red metallic solid [(smif)$_2$Rh][OTf] (0.028 g, 53%). $^1$H NMR (THF-d$_8$, 400 MHz): δ 6.51 (t, py-C$^5$H, 1 H, J=6.4 Hz), 6.87 (d, py-C$^3$H, 1 H, J=8.1 Hz), 6.85 (s, CH, 1 H), 7.29 (t, py-C$^4$H, 1 H, J=7.5 Hz), 7.77 (d, py-C$^6$H, 1 H, J=5.6 Hz). $^{13}$C{$^1$H} NMR (THF-d$_8$, 125 MHz): δ 114.72 (CH), 118.20 (py-C$^3$H), 138.70 (py-C$^5$H), 148.20 (py-C$^4$H), 148.29 (py-C$^6$H), 165.22 (py-C$^2$).

34. [(smif)$_2$Ir][BPh$_4$]: To a small bomb reactor charged with Nasmif (0.195 g, 0.889 mmol), NaBPh$_4$ (0.152 g, 0.444 mmol) and IrCl$_3$(THT)$_3$ (0.250 g, 0.444 mmol) was vacuum transferred 5 mL THF at −78° C. Upon warming to 23° C., the magenta solution quickly turned navy blue. The bomb was placed in a 70° C. oil bath for 2 d after which the solution was turquoise. The reaction mixture was filtered and washed in THF. All volatiles were removed in vacuo leaving dark purple metallic solid [(smif)$_2$Ir][BPh$_4$] (0.200 g, 50%). $^1$H NMR (THF-d$_8$, 400 MHz): δ 6.36 (t, py-C$^5$H, 1 H, J=6.7 Hz), 6.53 (d, py-C$^3$H, 1 H, J=8.3 Hz), 6.30 (s, CH, H), 7.03 (t, py-C$^4$H, 1 H, J=7.7 Hz), 7.60 (d, py-C$^6$H, 1 H, J=6.0 Hz). $^{13}$C{$^1$H} NMR (THF-d$_8$, 125 MHz): δ 116.08 (CH), 138.08 (py-C$^3$H), 140.52 (py-C$^5$H), 149.47 (py-C$^4$H), 163.36 (py-C$^6$H), 169.14 (py-C$^2$).

35. ((κ-N$^{am}$,N$^{im}$,N$^{py}$-1,2-bis(pyridine-2-yl)-2-(pyridine-2-methyleneamino)ethyl)(pyridine-2-ylmethy)amido)Mo (smif): To a three-neck round bottom flask charged with Nasmif (0.235 g, 1.07 mmol) and 0.95% sodium amalgam (0.911 g, 0.376 mmol) was vacuum transferred 40 mL THF at −78° C. MoCl$_3$(THF)$_3$ (0.150 g, 0.358 mmol) was added slowly to the magenta solution via a small addition finger and stirred at −78° C. for 2 h prior to warming to 23° C. After stirring at 23° C. for 16 h, all volatiles were removed in vacuo from the plum-red solution. The resulting solid was filtered in toluene and a dark red metallic solid was isolated from the cherry red solution (0.100 g, 40%). $^1$H NMR (THF-d$_8$, 600 MHz). $^{13}$C{$^1$H} NMR (THF-d$_8$, 150 MHz).

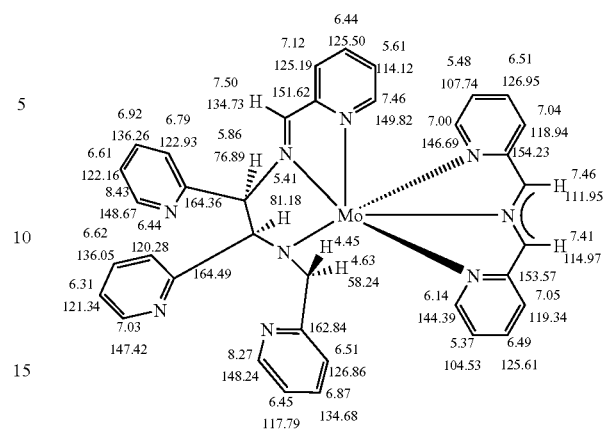

Equilibrium study: 2 (smif)FeN(SiMe$_3$)$_2$ (4)<=>[(TMS)$_2$NFe]$_2$(smif)$_2$ (4$_2$). A series of five NMR tubes were charged with known concentrations of (smif)FeN(SiMe$_3$)$_2$ (4). The solutions (3.4×10$^{-3}$ to 2.4×10$^{-2}$ M) of 4 in THF-d$_8$ were prepared in a 5 mL volumetric flask, and $^1$H NMR spectra were obtained at ambient temperature (~23° C.). The chemical shift associated with the smif 'backbone' CH was monitored as it exhibited the largest change as concentrations varied. The equilibrium constant, ~4×10$^{-4}$ M$^{-1}$, was fit using the least squares method developed by Tan (Tan, H. K. S. *J. Chem. Soc. Faraday Trans.*, 1994, 90, 3521-3525) for determining the NMR monomer shift and equilibrium constant for self-associating systems.

Computational Methods. B3LYP[1-3] geometry optimization utilized the Gaussian03$^i$ suite of programs; the 6-31G(d) basis set was employed. Tests with the larger 6-311+G(d) basis set did not reveal significant differences in the optimized geometries.

No symmetry constraints were employed in geometry optimization. Where applicable, geometry optimizations were started from both a pseudo-D2d structure (akin to crystal structure of (smif)$_2$Fe (1)) and/or a highly Jahn-Teller distorted starting geometry (e.g., (smif)$_2$Co (2)). Calculation of the energy Hessian was performed to confirm species as minima on their respective potential energy surfaces at this level of theory. All plausible spin multiplicities were investigated for the different M(smif)$_2$ complexes.

Modeling of open-shell species with density functional theory employed unrestricted Kohn-Sham methods. As can be seen in Table S-1, no evidence of significant spin contamination was evidence via the calculation of the <Ŝ$^2$> expectation value.

TABLE S-1

Calculated spin-states for (smif)$_2$M (M = Fe (1), Co (2), Ni (3)).$^a$

| cmpd | Mult | Calcd M(II) d$^n$ | M(spin) e$^-$ | G a.u. | G$_{rel}$ kcal/mol | <Ŝ$^2$> calc |
|---|---|---|---|---|---|---|
| (smif)$_2$Fe (1) | singlet | 6 | n/a | −2518.4386 | 0 | n/a |
| (smif)$_2$Fe | triplet | 6 | 0.80 | −2518.3980 | 25.5 | 2.024 |
| (smif)$_2$Fe | quintet | 6 | 0.75 | −2518.3543 | 52.9 | 6.049 |
| (smif)$_2$Co (2) | doublet | 7 | −0.01 | −2637.4373 | 0 | 0.760 |
| (smif)$_2$Co | quartet | 7 | 1.20 | −2637.4208 | 10.4 | 3.786 |
| (smif)$_2$Ni | singlet | 8 | n/a | −2762.9219 | 43.9 | n/a |
| (smif)$_2$Ni (3) | triplet | 8 | 1.70 | −2762.9919 | 0 | 2.006 |

$^a$Mult = spin multiplicity; M(II) d$^n$ = formal d-orbital count on the transition metal assuming the smif ligand has −1 charge; Calcd M(spin) = calculated spin density on metal; G = the calculated Gibb free energy in a.u.; <Ŝ$^2$> is the total spin expectation value: ideal values are 0.75 for a doublet; 2.00 for a triplet; 3.75 for a quartet; 6.00 for a quintet.

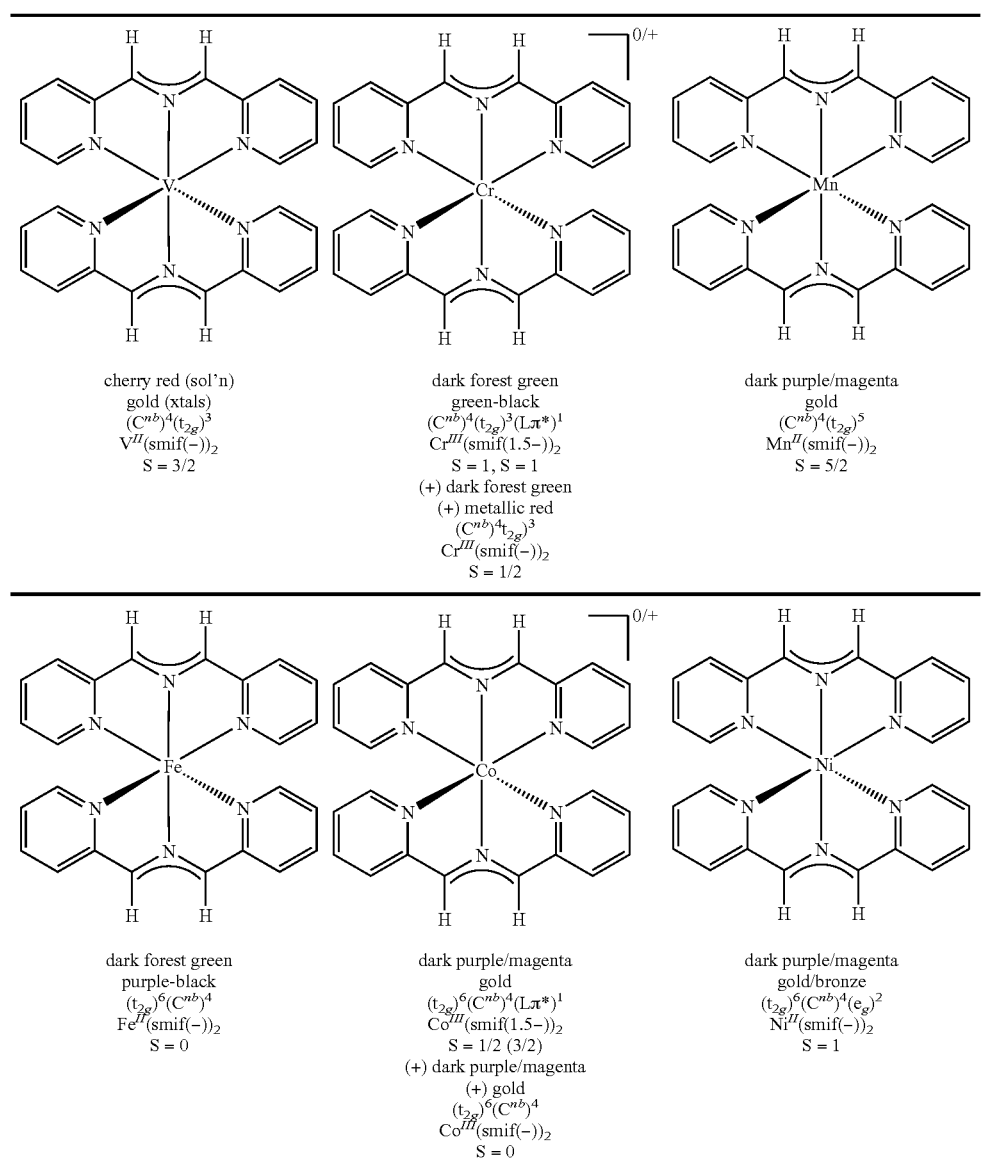

| | | |
|---|---|---|
| cherry red (sol'n) gold (xtals) $(C^{nb})^4(t_{2g})^3$ $V^{II}(smif(-))_2$ $S = 3/2$ | dark forest green green-black $(C^{nb})^4(t_{2g})^3(L\pi^*)^1$ $Cr^{III}(smif(1.5-))_2$ $S = 1, S = 1$ (+) dark forest green (+) metallic red $(C^{nb})^4(t_{2g})^3$ $Cr^{III}(smif(-))_2$ $S = 1/2$ | dark purple/magenta gold $(C^{nb})^4(t_{2g})^5$ $Mn^{II}(smif(-))_2$ $S = 5/2$ |
| dark forest green purple-black $(t_{2g})^6(C^{nb})^4$ $Fe^{II}(smif(-))_2$ $S = 0$ | dark purple/magenta gold $(t_{2g})^6(C^{nb})^4(L\pi^*)^1$ $Co^{III}(smif(1.5-))_2$ $S = 1/2\ (3/2)$ (+) dark purple/magenta (+) gold $(t_{2g})^6(C^{nb})^4$ $Co^{III}(smif(-))_2$ $S = 0$ | dark purple/magenta gold/bronze $(t_{2g})^6(C^{nb})^4(e_g)^2$ $Ni^{II}(smif(-))_2$ $S = 1$ |

TABLE 1

X-ray Crystallographic Parameters ($N_a$ = aza N; $N_p$ = py N) and Physical Data for $(smif)_2M$ (1-M) and $[(smif)_2M]OTf$ (1-M$^+$)

| cmpd | d(MN$_a$) | d(MN$_p$) | N$_a$MN$_p$ | N$_a$MN$'_a$ | $\mu_{eff}$ | S | l$_{max}$ (nm), e(M$^{-1}$cm$^{-1}$) |
|---|---|---|---|---|---|---|---|
| 1-V | 2.058(18) | 2.118(7) | 77.25(22) | 172.08(36) | 3.6 | 3/2 | 573 (10 000), 471 (12 000)[a] |
| 1-Cr | 1.940(11), 2.010(26) | 2.034(12) | 79.19(3) | 176.1(5) | 2.8 | 1 | 637 (18 000), 401 (29 000)[b] |
| [1-Cr$^+$]OTf$^-$ | 1.994(5) | 2.035(2) | 80.46(8) | 176.73(9) | 3.6 | 1/2 | 626 (22 000), 492 (13 000)[c] |
| 1-Mn | 2.197(16) | 2.236(7) | 74.0(4) | 166.50(7) | 5.8 | 5/2 | 590 (60 000), 403 (23 000) |
| 1-Fe | 1.9012(14) | 1.9634(12) | 82.3(2) | 179.11(6) | 0 | 0 | 597 (16 000), 441 (42 000) |
| 1-Co[d] | 1.888(3), 1.946(3) 1.945(3), 1.939(3) | 2.184(13), 1.971(13) 2.105(16), 2.053(5) | 82.2(2), 79.2(3) 80.3(6) | 177.30(11) 177.76(12) | 1.7[d] | 1/2 | 563 (29 000), 401 (20 000) |
| [1-Co$^+$]OTf$^{-e}$ | 1.8768(11) | 1.9252(19) | 83.9(2) | 179.05(10) | 0 | 0 | 586 (23 000), 383 (13 000) |
| 1-Ni | 2.019(5) | 2.093(9) | 79.1(3) | 176.00(12) | 2.8 | 1 | 574 (50 000), 399 (18 000) |

[a]Also 514 (11 000), 401 (10 000).
[b]Also 490 (19 000).
[c]Also 385 (13 000). [d]$\mu_{eff}$(10 K) = 1.7; $\mu_{eff}$(300 K) = 2.8; possibly one S = 1/2 and one S = 3/2 molecule in unit cell.
[e]Also 321 (11 000).

The invention claimed is:

1. A compound of formula II

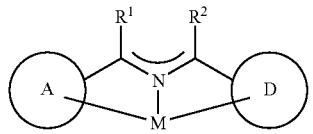

II wherein
- A is optionally substituted phenyl or optionally substituted pyridinyl;
- D is optionally substituted phenyl or optionally substituted pyridinyl;
- ⌣ is a delocalized bond;
- $R^1$ and $R^2$ are each independently selected from hydrogen, halogen, an optionally substituted $(C_1\text{-}C_{20})$ hydrocarbon, —C(=O)—$R^{10}$, —C(=O)N$R^{10}R^{11}$, —C(=O)O$R^{10}$, —C(=S)N$R^{10}R^{11}$, —C(=S)—$R^{10}$ and —C(=S)O$R^{10}$; or
- $R^1$ and $R^2$, together with the carbons to which they are attached, may be an optionally substituted non-aromatic ring;
- $R^{10}$ and $R^{11}$ are each selected independently from hydrogen, an optionally substituted $(C_1\text{-}C_{20})$ hydrocarbon and a polar, neutral moiety;
- ⌇ represents a coordinate covalent bond to a metal; and
- M is a metal that forms additional bonds to A and D;

with the proviso that, when two azaallyl moieties are present, A and D are both unsubstituted pyridinyl, and $R^1$ and $R^2$ are both hydrogen, the metal cannot be zinc, iron, cobalt, or nickel.

2. A compound of formula IIa according to claim 1 wherein M has one additional substituent bond:

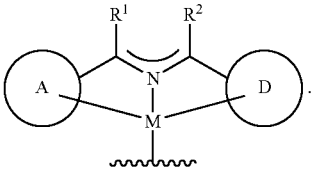

IIa

3. A compound according to claim 2 wherein the additional substituent bonded to M is selected from N$R^{20}R^{21}$ and O$R^{22}$;
- $R^{20}$ and $R^{21}$ are each selected independently in each occurrence from Si[$(C_1\text{-}C_6)$alkyl]$_3$ and $(C_1\text{-}C_{20})$ hydrocarbon; and
- $R^{22}$ is $(C_1\text{-}C_{20})$ hydrocarbon.

4. A compound according to claim 1 wherein M has three additional substituent bonds as in formula III:

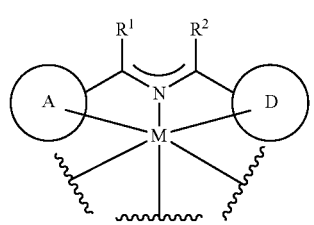

III

5. A compound according to claim 4 of formula IIIa or IIIb:

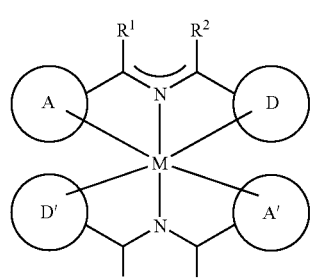

IIIa

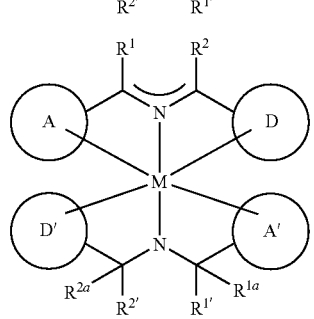

IIIb wherein
- $R^{1'}$ and $R^{2'}$ are each independently in each occurrence selected from hydrogen, halogen, an optionally substituted $(C_1\text{-}C_{20})$ hydrocarbon, —C(=O)—$R^{10}$, —C(=O)N$R^{10}R^{11}$, —C(=O)O$R^{10}$, —C(=S)N$R^{10}R^{11}$, —C(=S)—$R^{10}$ and —C(=S)O$R^{10}$; or
- $R^{1'}$ and $R^{2'}$, together with the carbons to which they are attached, may be an optionally substituted non-aromatic ring;
- $R^{1a}$ and $R^{2a}$ are each independently selected from hydrogen and $(C_1\text{-}C_6)$alkyl;
- A' is an optionally substituted phenyl or optionally substituted pyridinyl; and
- D' is an optionally substituted phenyl or optionallt substituted pyridinyl.

6. A compound according to claim 1 wherein said metal is chosen from lithium, sodium, magnesium, titanium, vanadium, chromium, manganese, iron, cobalt, nickel, zinc, molybdenum, ruthenium, rhodium and iridium.

7. A compound according to claim 1 wherein A and D are each optionally substituted with one or more substituents selected from hydrogen, $(C_1\text{-}C_6)$alkyl, halogen, alkoxy, nitro, nitroso, haloalkyl, haloalkoxy, oxaalkyl, acyl and cyano.

8. A compound according to claim 1 wherein $R^1$ and $R^2$ are each selected independently from hydrogen, $(C_1\text{-}C_6)$alkyl, fluoro$(C_1\text{-}C_6)$alkyl, —C(=O)—$R^{10}$ and —C(=O)N$R^{10}R^{11}$.

9. A compound according to claim 8 wherein $R^2$ is selected from hydrogen and $(C_1\text{-}C_6)$alkyl and, when $R^1$ is —C(=O)—$R^{10}$ or C(=O)N$R^{10}R^{11}$, $R^{10}$ is selected from hydrogen and $(C_1\text{-}C_6)$alkyl, and $R^{11}$ is $(C_1\text{-}C_{20})$ hydrocarbon optionally substituted with fluorine.

10. A compound according to claim 1 wherein A and D are each optionally substituted with one or more substituents selected from hydrogen, $(C_1\text{-}C_6)$alkyl, halogen, alkoxy, nitro, nitroso, haloalkyl, haloalkoxy, oxaalkyl, acyl and cyano.

11. A compound according to claim 5 wherein
M is chosen from lithium, sodium, magnesium, titanium, vanadium, chromium, manganese, iron, cobalt, nickel, zinc, molybdenum, ruthenium, rhodium and iridium;

A, D, A' and D' are each independently selected from optionally substituted phenyl or optionally substituted pyridinyl; each optionally substituted with one or more substituents selected from hydrogen, $(C_1-C_6)$alkyl, halogen, alkoxy, nitro, nitroso, haloalkyl, haloalkoxy, oxaalkyl, acyl and cyano;

$R^1$ and $R^2$ are each independently selected from hydrogen, $(C_1-C_6)$alkyl, —C(=O)—$R^{10}$ and —C(=O)N$R^{10}R^{11}$; and $R^{1a}$ and $R^{2a}$ are each independently selected from hydrogen and $(C_1-C_6)$alkyl.

12. A compound according to claim 11 wherein
A, D, A' and D' are each independently chosen from optionally substituted phenyl and optionally substituted pyridinyl;
$R^1$ is —C(=O)N$R^{10}R^{11}$;
$R^2$ is hydrogen or $(C_1-C_6)$alkyl;
$R^{10}$ is selected from H and $(C_1-C_6)$alkyl; and
$R^{11}$ is $(C_1-C_{20})$ hydrocarbon optionally substituted with fluorine.

13. A photovoltaic cell comprising a compound of formula II:

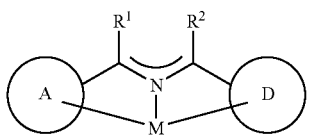

II wherein
A is optionally substituted phenyl or optionally substituted pyridinyl;
D is optionally substituted phenyl or optionally substituted pyridinyl;
⌣ is a delocalized bond;
$R^1$ and $R^2$ are each independently selected from hydrogen, halogen, an optionally substituted $(C_1-C_{20})$ hydrocarbon, —C(=O)—$R^{10}$, —C(=O)N$R^{10}R^{11}$, —C(=O)O$R^{10}$, —C(=S)N$R^{10}R^{11}$, —C(=S)—$R^{10}$ and —C(=S)O$R^{10}$; or
$R^1$ and $R^2$, together with the carbons to which they are attached, may be an optionally substituted non-aromatic ring;
$R^{10}$ and $R^{11}$ are each selected independently from hydrogen, an optionally substituted $(C_1-C_{20})$ hydrocarbon and a polar, neutral moeity;
M is a metal that forms additional bonds to A and D; and
⌿ represents a coordinate covalent bond to a metal.

14. An organic light emitting diode comprising a compound of formula II:

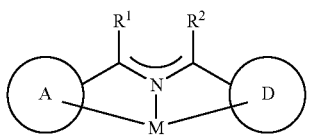

II wherein
A is optionally substituted phenyl or optionally substituted pyridinyl;
D is optionally substituted phenyl or optionally substituted pyridinyl;

⌣ is a delocalized bond;
$R^1$ and $R^2$ are each independently selected from hydrogen, halogen, an optionally substituted $(C_{1-C20})$ hydrocarbon, —C(=O)—$R^{10}$, —C(=O)N$R^{10}R^{11}$, —C(=O)O$R^{10}$, —C(=S)N$R^{10}R^{11}$, —C(=S)—$R^{10}$ and —C(=S)O$R^{10}$; or
$R^1$ and $R^2$, together with the carbons to which they are attached, may be an optionally substituted non-aromatic ring;
$R^{10}$ and $R^{11}$ are each selected independently from hydrogen, an optionally substituted $(C_1-C_{20})$ hydrocarbon, and a polar, neutral moiety;
M is a metal that forms additional bonds to A and D; and
⌿ represents a coordinate covalent bond to a metal.

15. A compound according to claim 6 of formula

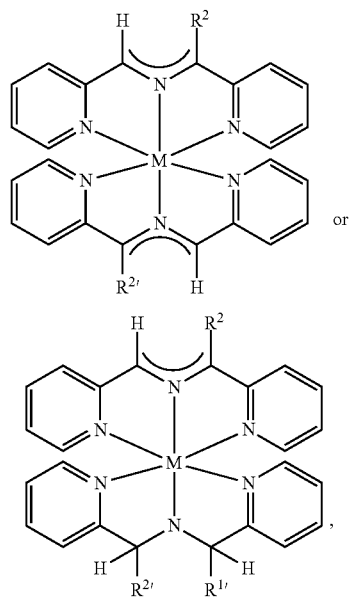

or wherein M is selected from lithium, sodium, magnesium, titanium, vanadium, chromium, manganese, iron, cobalt, nickel, zinc, molybdenum, ruthenium, rhodium and iridium.

16. A compound according to claim 15 of formula

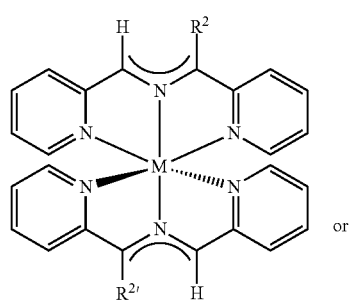

or

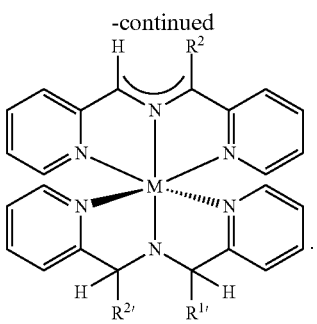

17. A compound according to claim 2 of formula

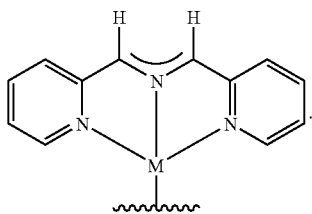

18. A compound according to claim 1 selected from:
(smif)₂V,
(smif)₂Cr,
(smif)₂Mn,
(smif)₂Mg,
(smif)CrN(SiMe₃)₂,
(smif)FeN(SiMe₃)₂,
(smif)FeOCHPh₂,
(smif)(dpma)Fe,
Li(smif),
Na(smif),
Na$^t$BuNCOsmif,
($^t$BuNCOsmif)₂Fe,
(2,6-$^i$PrPhNCOsmif)₂Fe,
(smif)(dpma)Ti,
(smif)₂Ti,
(κ-N$^{am}$,N$^{py}$₂-2,3,5,6-tetrakis(pyridin-2-yl)piperazin-1-yl)(smif)Ti,
Lithium[(k-C,N$^{am}$,N$^{im}$,N$^{py}$₃-1,2-bis(pyridin-2-yl)-2-(pyridin-2-ylmethyleneamino)ethyl)(pyridin-2-ylmethideyl)amido)Ti(smif)],
(smif)₂Ru,
((κ-N$^{am}$,N$^{im}$,N$^{py}$-1,2-bis(pyridine-2-yl)-2-(pyridine-2-methyleneamino)ethyl)(pyridine-2-ylmethyl)amido)Mo(smif),

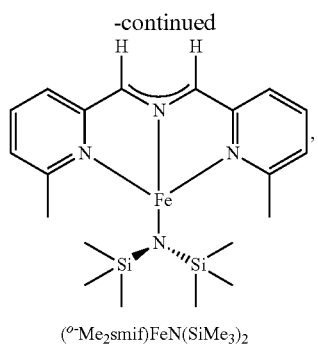

($^o$-Me₂smif)FeN(SiMe₃)₂

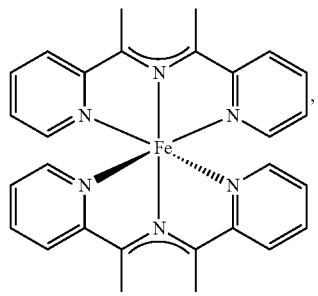

($^b$Me₂smif)₂Fe

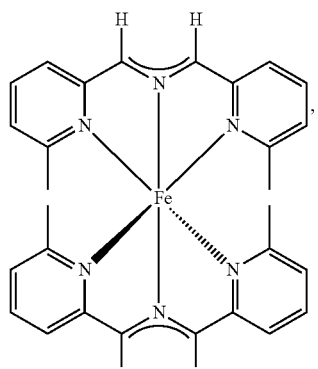

($^o$Me₂smif)₂Fe

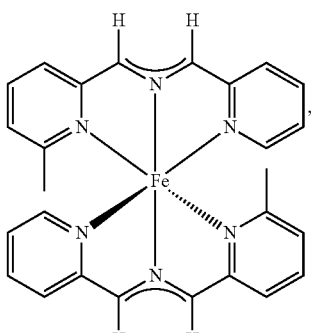

($^o$Mesmif)₂Fe and

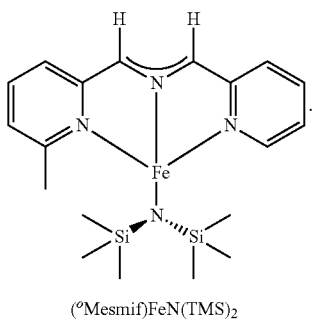

(*o*Mesmif)FeN(TMS)₂

19. A crystalline compound of formula II:

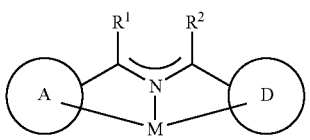

wherein
A is optionally substituted pyridinyl or optionally substituted phenyl;
D is optionally substituted pyridinyl or optionally substituted phenyl;
⌣ is delocalized bond;
R¹ and R² are each independently selected from hydrogen, halogen, an optionally substituted $(C_1-C_{20})$ hydrocarbon, —C(=O)—R¹⁰, —C(=O)NR¹⁰R¹¹, —C(=O)OR¹⁰, —C(=S)NR¹⁰R¹¹, —C(=S)—R¹⁰ and —C(=S)OR¹⁰; or
R¹ and R², together with the carbons to which they are attached, may be an optionally substituted non-aromatic ring;
R¹⁰ and R¹¹ are each selected independently from hydrogen, an optionally substituted $(C_1-C_{20})$ hydrocarbon, and a polar, neutral moiety;
M is a metal that forms additional bonds to A and D; and
⫯ represents a coordinate covalent bond to a metal.

20. The crystalline compound according to claim 19 selected from:
(smif)₂V,
(smif)₂Cr,
(smif)₂Mn,
(smif)₂Fe,
(smif)₂Co,
(smif)₂Ni,
(smif)₂Mg,
(smif)CrN(SiMe₃)₂,
(smif)FeN(SiMe₃)₂,
(smif)FeOCHPh₂,
(smif)(dpma)Fe,
Li(smif),
Na(smif),
Na$^t$BuNCOsmif,
($^t$BuNCOsmif)₂Fe,
(2,6-$^i$PrPhNCOsmif)₂Fe,
(smif)(dpma)Ti,
(smif)₂Ti,
(κ-$N^{am}$,$N^{py}$₂-2,3,5,6-tetrakis(pyridin-2-yl)piperazin-1-yl)(smif)Ti,
Lithium[(k-C,$N^{am}$,$N^{im}$,$N^{py}$₃-1,2-bis(pyridin-2-yl)-2-(pyridin-2-ylmethyleneamino)ethyl)(pyridin-2-ylmethideyl)amido)Ti(smif)],
(smif)₂Ru,
((κ-$N^{am}$,$N^{im}$,$N^{py}$-1,2-bis(pyridine-2-yl)-2-(pyridine-2-methyleneamino)ethyl)(pyridine-2-ylmethyl)amido)Mo(smif),

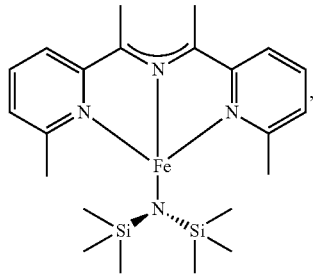

(Me₄smif)FeN(SiMe₃)₂

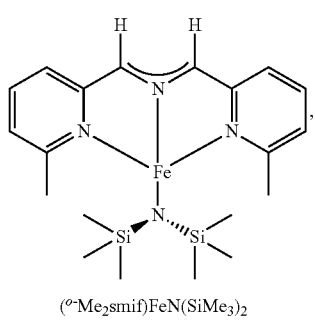

(*o*-Me₂smif)FeN(SiMe₃)₂

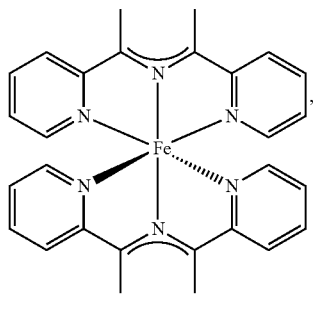

($^b$Me₂smif)₂Fe

-continued
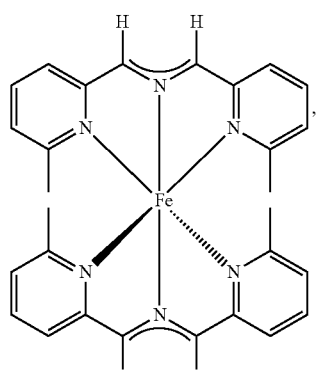
(ᴼMe₂smif)₂Fe
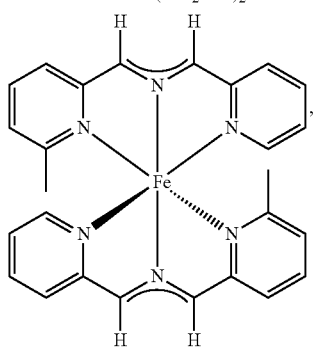
and
(ᴼMesmif)₂Fe
-continued
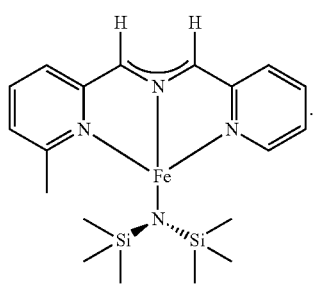
(ᴼMesmif)FeN(TMS)₂
21. A compound according to claim 1, wherein A is optionally substituted pyridinyl and D is optionally substituted pyridinyl.
22. A compound according to claim 1, wherein A is optionally substituted phenyl and D is optionally substituted phenyl.
* * * * *

UNITED STATES PATENT AND TRADEMARK OFFICE
CERTIFICATE OF CORRECTION

PATENT NO.        : 8,846,919 B2                                        Page 1 of 1
APPLICATION NO.   : 12/704170
DATED             : September 30, 2014
INVENTOR(S)       : Wolczanski et al.

It is certified that error appears in the above-identified patent and that said Letters Patent is hereby corrected as shown below:

In the Claims

Column 51, Line 43: Claim 13, Delete "$R^{1\ and\ R2}$" and insert --$R^1$ and $R^2$--

Column 52, Line 3: Claim 14, Delete "$C_{1-C20)\ hydrocarbon,\ -C(=O)-R^{10}}$," and insert --$C_1$-$C_{20}$) hydrocarbon, -C(=O)-$R^{10}$,--

Signed and Sealed this
Sixth Day of January, 2015

Michelle K. Lee
*Deputy Director of the United States Patent and Trademark Office*